US010918602B2

(12) United States Patent
Dave et al.

(10) Patent No.: US 10,918,602 B2
(45) Date of Patent: Feb. 16, 2021

(54) COMPOSITIONS AND METHODS FOR PREPARING POLYMERIC FILMS LOADED WITH UNIFORMLY DISTRIBUTED DRUG PARTICLES

(71) Applicant: New Jersey Institute of Technology, Newark, NJ (US)

(72) Inventors: Rajesh N. Dave, Princeton, NJ (US); Lu Zhang, Kearny, NJ (US); Guluzar Gorkem Buyukgoz, Saddle Brook, NJ (US); Eylul Cetindag, Piscataway, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 16/150,931

(22) Filed: Oct. 3, 2018

(65) Prior Publication Data

US 2019/0099373 A1  Apr. 4, 2019

Related U.S. Application Data

(60) Provisional application No. 62/567,517, filed on Oct. 3, 2017.

(51) Int. Cl.
| | |
|---|---|
| *A61K 9/16* | (2006.01) |
| *A61K 9/70* | (2006.01) |
| *A61K 45/06* | (2006.01) |
| *A61K 47/10* | (2017.01) |
| *A61K 47/20* | (2006.01) |
| *A61K 31/343* | (2006.01) |
| *A61K 9/00* | (2006.01) |
| *A61K 31/216* | (2006.01) |
| *A61K 47/38* | (2006.01) |
| *A61K 9/50* | (2006.01) |

(52) U.S. Cl.
CPC ............ *A61K 9/1682* (2013.01); *A61K 9/006* (2013.01); *A61K 9/7007* (2013.01); *A61K 31/216* (2013.01); *A61K 31/343* (2013.01); *A61K 45/06* (2013.01); *A61K 47/10* (2013.01); *A61K 47/20* (2013.01); *A61K 9/501* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 8,252,370 B1 | 8/2012 | Young et al. | |
| 2011/0244047 A1* | 10/2011 | Asari | A61K 9/0056 424/489 |
| 2016/0022599 A1 | 1/2016 | Dave et al. | |

FOREIGN PATENT DOCUMENTS

WO  2014/145699  9/2014

OTHER PUBLICATIONS

Lippold et al., Correlation Between Wettability and Dissolution Rate of Pharmaceutical Powders, International Journal of Pharmaceutics 28, 67-74, 1986.
Ford et al., Importance of Drug Type, Tablet Shape and Added Diluents on Drug Release Kinetics From Hydroxypropylmethylcellulose Matrix Tablets, International Journal of Pharmaceutics 40, 223-234, 1987.
Ritger et al., A Simple Equation for Description of Solute Release I. Fickian and Non-Fickian Release from Non-Swellable Devices in the Form of Slabs, Spheres, Cylinders or Discs, Journal of Controlled Release 5, 23-36, 1987.
Ritger et al., A Simple Equation for Description of Solute Release II. Fickian and Anomalous Release from Swellable Devices, Journal of Controlled Release 5, 37-42, 1987.
Conte et al., Multi-Layered Hydrophilic Matrices as Constant Release Devices (GeomatrixTM Systems), Journal of Controlled Release 26, 39-47, 1993.
Ford et al., Thermal Analysis of Gels and Matrix Tablets Containing Cellulose Ethers, Thermochimica Acta 248, 329-345, 1995.
Aitken-Nichol et al., Hot Melt Extrusion of Acrylic Films, Pharm Res 13, 804-808, 1996.
De Villiers, Influence of Agglomeration of Cohesive Particles on the Dissolution Behaviour of Furosemide Powder, International Journal of Pharmaceutics 136, 175-179, 1996.
FDA Guidance for Industry Dissolution Testing of Immediate Release Solid Oral Dosage Forms, U.S. Department of Health and Human Services, Food and Drug Administration, Center for Drug Evaluation and Research (CDER), 17 pages, Aug. 1997.
Brown et al., Surface Treatment of the Hydrophobic Drug Danazol to Improve Drug Dissolution, International Journal of Pharmaceutics 165, 227-237, 1998.
Repka et al., Physical-Mechanical, Moisture Absorption and Bioadhesive Properties of Hydroxypropylcellulose Hot-Melt Extruded Films, Biomaterials 21, 1509-1517, 2000.

(Continued)

*Primary Examiner* — Melissa L Fisher
(74) *Attorney, Agent, or Firm* — McCarter & English, LLP

(57) ABSTRACT

The present disclosure provides improved film based pharmaceutical products containing uniformly distributed drug or active agent particles (e.g., to achieve improved/excellent dissolution control including enhancing dissolution and bioavailability and/or product uniformity). More particularly, the present disclosure provides improved systems/methods for fabricating film based pharmaceutical products by utilizing higher surface modified micronized drug or active agent powders and film forming precursors and drying methods that accomplish improved/efficient drying and provide improved/excellent content uniformity of active pharmaceutical agents in the fabricated film based pharmaceutical products. In exemplary embodiments, the present disclosure provides for an easier means of directly incorporating dry micronized poorly water-soluble drugs or active agent particles (e.g., fenofibrate ("FNB")) into films. The present disclosure demonstrates some advantages of direct incorporation of surface modified-micronized poorly water-soluble drug or active agent powders in film manufacturing.

19 Claims, 58 Drawing Sheets

(56) References Cited

OTHER PUBLICATIONS

Siepmann et al., Calculation of the Required Size and Shape of Hydroxypropyl Methylcellulose Matrices to Achieve Desired Drug Release Profiles, International Journal of Pharmaceutics 201, 151-164, 2000.
Costa, An Alternative Method to the Evaluation of Similarity Factor in Dissolution Testing, International Journal of Pharmaceutics 220, 77-83, 2001.
Costa et al., Modeling and Comparison of Dissolution Profiles, European Journal of Pharmaceutical Sciences 13, 123-133, 2001.
Kendall et al., Adhesion and Aggregation of Fine Particles. Powder Technology 121, 223-229, 2001.
Costa et al., Comparison of Dissolution Profiles of Ibuprofen Pellets, Journal of Controlled Release 89, 199-212, 2003.
Perrut et al., Enhancement of Dissolution Rate of Poorly-Soluble Active Ingredients by Supercritical Fluid Processes: Part I: Micronization of Neat Particles, International Journal of Pharmaceutics 288, 3-10, 2005.
Repka et al., Characterization of Cellulosic Hot-Melt Extruded Films Containing Lidocaine, European Journal of Pharmaceutics and Biopharmaceutics 59, 189-196, 2005.
Jamzad et al., Role of Surfactant and pH on Dissolution Properties of Fenofibrate and Glipizide—A Technical Note, AAPS PharmSciTech 7, E17-E22, 2006.
Tian et al., Influence of Polymorphic Form, Morphology, and Excipient Interactions on the Dissolution of Carbamazepine Compacts, Journal of Pharmaceutical Sciences 96, 584-594, 2007.
Cilurzo et al., Fast Dissolving Films Made of Maltodextrins, European Journal Pharm Biopharm 70, 895-900, 2008.
Vogt, et al., Dissolution Enhancement of Fenofibrate by Micronization, Cogrinding and Spray-Drying: Comparison with Commercial Preparations, European Journal of Pharmaceutics and Biopharmaceutics 68, 283-288, 2008.
Averineni et al., Development of Mucoadhesive Buccal Films for the Treatment of Oral Sub-Mucous Fibrosis: A Preliminary Study, Pharmaceutical Development and Technology 14, 199-207, 2009.
Dixit et al., Oral Strip Technology: Overview and Future Potential, Journal of Controlled Release 139, 94-107, 2009.
Casas et al., Tapioca Starch Graft Copolymers and Dome Matrix® Modules Assembling Technology, I. Effect of Module Shape on Drug Release, European Journal of Pharmaceutics and Biopharmaceutics 75, 42-47, 2010.
Buch et al., Improvement of the Wettability and 600 Dissolution of Fenofibrate Compacts by Plasma Treatment, International Journal of Pharmaceutics 416, 49-54, 2011.
Davé et al., Particle Engineering Via Dry Coating: Development of a Novel Material Sparing Technology for Pharmaceutical Powders, AiChe Annual Meeting, Pittsburgh, 2011.
Han et al., Simultaneous Micronization and Surface Modification for Improvement of Flow and Dissolution of Drug Particles, International Journal of Pharmaceutics 415, 185-195, 2011.
Hoffmann et al., Advances in Orodispersible Films for Drug Delivery, Expert Opinion on Drug Delivery 8, 299-316, 2011.
Juhnke et al., Generation of Wear During the Production of Drug Nanosuspensions by Wet Media Milling, European Journal of Pharmaceutics and Biopharmaceutics 81, 214-222, 2012.
Sievens-Figueroa et al., Preparation and Characterization of Hydroxypropyl Methyl Cellulose Films Containing Stable BCS Class II Drug Nanoparticles for Pharmaceutical Applications, International Journal of Pharmaceutics 423, 496-508, 2012.
Sievens-Figueroa et al., Using USP I and USP IV for Discriminating Dissolution Rates of Nano- and Microparticle-Loaded Pharmaceutical Strip-Films, AAPS PharmSciTech 13, 1473-1482, 2012.
Beck et al., Effects of Stabilizers on Particle Redispersion and Dissolution from Polymer Strip Films Containing Liquid Antisolvent Precipitated Griseofulvin Particles, Powder Technology 236, 37-51, 2013.
Ghoroi et al., Multifaceted Characterization of Pharmaceutical Powders to Discern the Influence of Surface Modification, Powder Technology 236, 63-74, 2013.
Han et al., Dry Coating of Micronized API Powders for Improved Dissolution of Directly Compacted Tablets with High Drug Loading, International Journal of Pharmaceutics 442, 74-85, 2013.
Nair et al., In Vitro Techniques to Evaluate Buccal Films, Journal of Control Release 166, 10-21, 2013.
Susarla et al., Fast Drying of Biocompatible Polymer Films Loaded with Poorly Water-Soluble Drug Nano-Particles Via Low Temperature Forced Convection, International Journal of Pharmaceutics 455, 93-103, 2013.
Preis et al., Mechanical Strength Test for Orodispersible and Buccal Films, International Journal of Pharmaceutics 461, 22-29, 2014.
Azad et al., Enhanced Physical Stabilization of Fenofibrate Nanosuspensions Via Wet Co-Milling with a Superdisintegrant and an Adsorbing Polymer, European Journal of Pharmaceutics and Biopharmaceutics 94, 372-385, 2015.
Borges et al., Oral Films: Current Status and Future Perspectives: I Galenical Development and Quality Attributes, Journal of Controlled Release 206, 1-19, 2015.
Brniak et al., Orodispersible Films and Tablets with Prednisolone Microparticles, European Journal of Pharmaceutical Sciences 75, 81-90, 2015.
Krull et al., Polymer Strip Films for Delivery of Poorly Water-Soluble Drugs, American Pharmaceutical Review 18, 2015.
Krull et al., Polymer Strip Films as a Robust, Surfactant-Free Platform for Delivery of BCS Class II Drug Nanoparticles, International Journal of Pharmaceutics 489, 45-57, 2015.
Susarla et al., Novel Use of Superdisintegrants as Viscosity Enhancing Agents In Biocompatible Polymer Films Containing Griseofulvin Nanoparticles, Powder Technology 285, 25-33, 2015.
Bhakay et al., Incorporation of Fenofibrate Nanoparticles Prepared by Melt Emulsification into Polymeric Films. Journal of Pharmaceutical Innovation 11, 53-63, 2016.
Krull et al., Preparation and Characterization of Fast Dissolving Pullulan Films Containing BCS Class II Drug Nanoparticles for Bioavailability Enhancement, Drug Dev Ind Pharm 42, 1073-1085, 2016.
Krull et al., Critical Material Attributes (CMAs) of Strip Films Loaded with Poorly Water-Soluble Drug Nanoparticles: I. Impact of Plasticizer on Film Properties and Dissolution, Eur J Pharm Sci 92, 146-155, 2016.
Krull et al., Critical Material Attributes of Strip Films Loaded with Poorly Water-Soluble Drug Nanoparticles: II, Impact of Polymer Molecular Weight, J Pharm Sci 106, 619-628, 2017.
Krull et al., Crtical Material Attributes (CMAs) of Strip Films Loaded with Poorly Water-Soluble Drug Nanoparticles: III Impact of Drug Nanoparticle Loading, International Journal of Pharmaceutics, 523, 33-41, 2017.
U.S. Appl. No. 62/567,517, filed Oct. 3, 2017.

* cited by examiner

FIGURE 2A
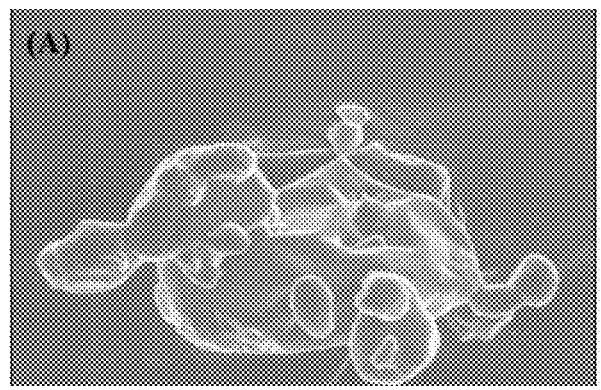
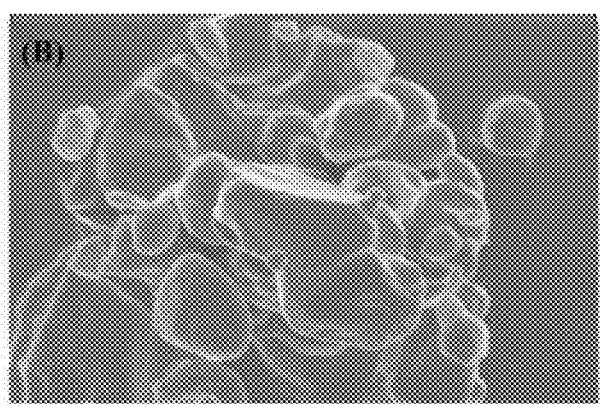
FIGURE 2B
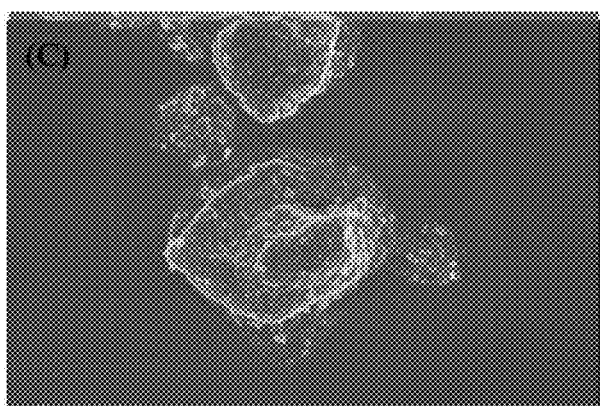
FIGURE 2C

FIGURE 3A 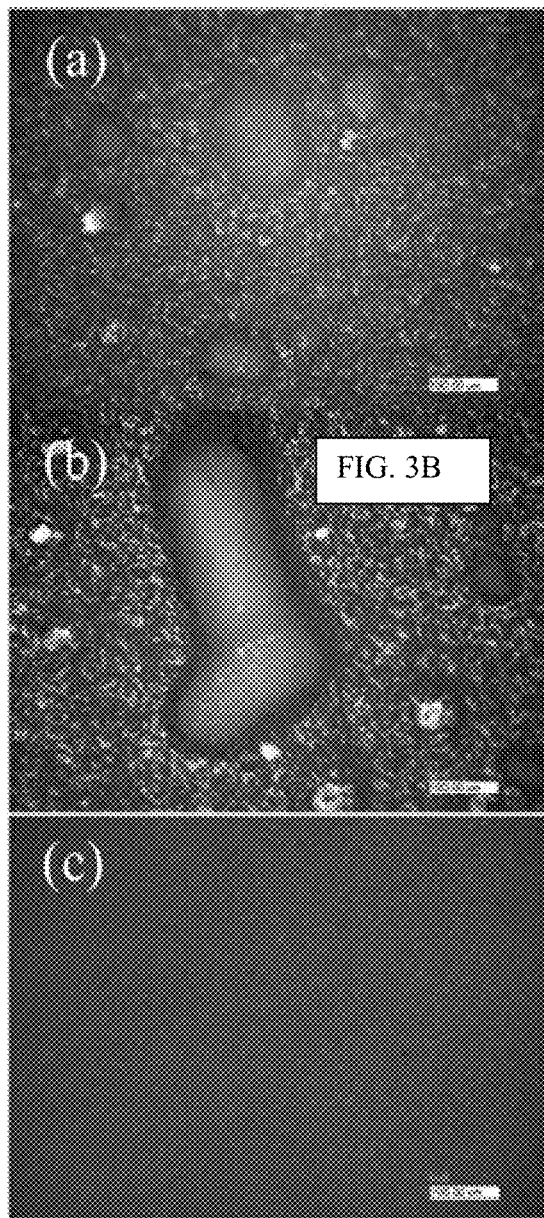 FIGURE 3D 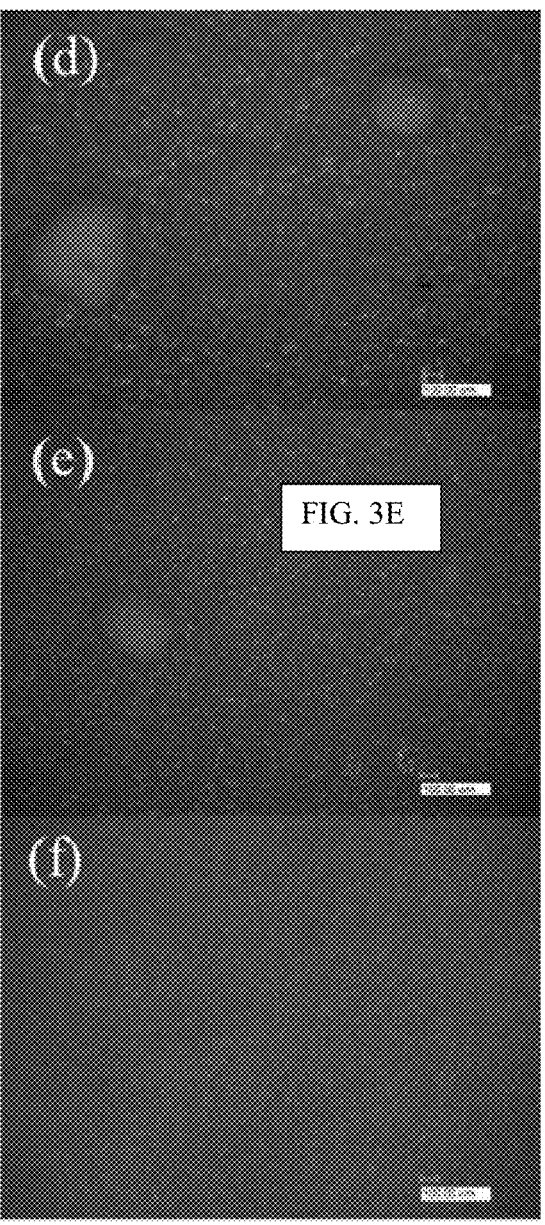
FIG. 3B
FIG. 3E
FIGURE 3C 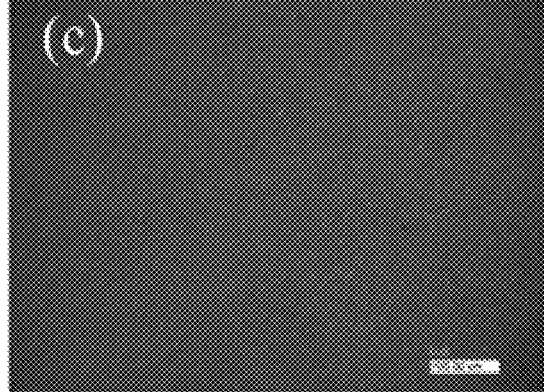 FIGURE 3F 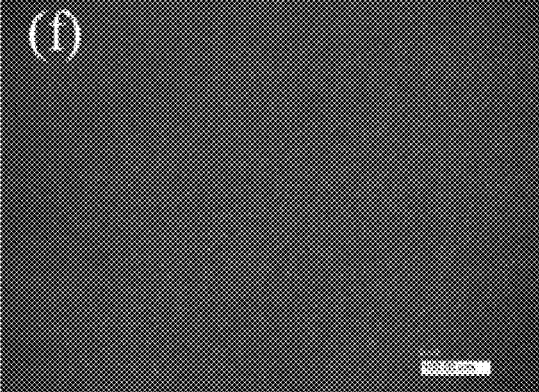

FIGURE 9A FIGURE 9C
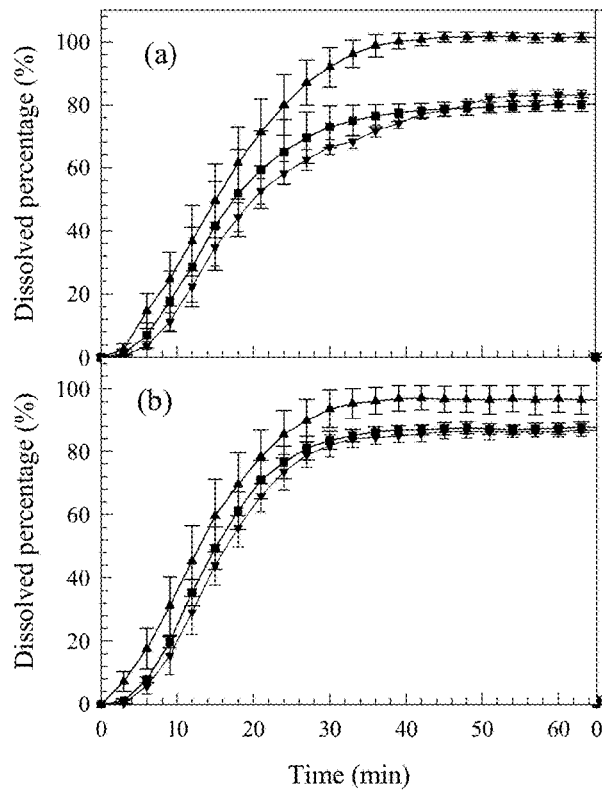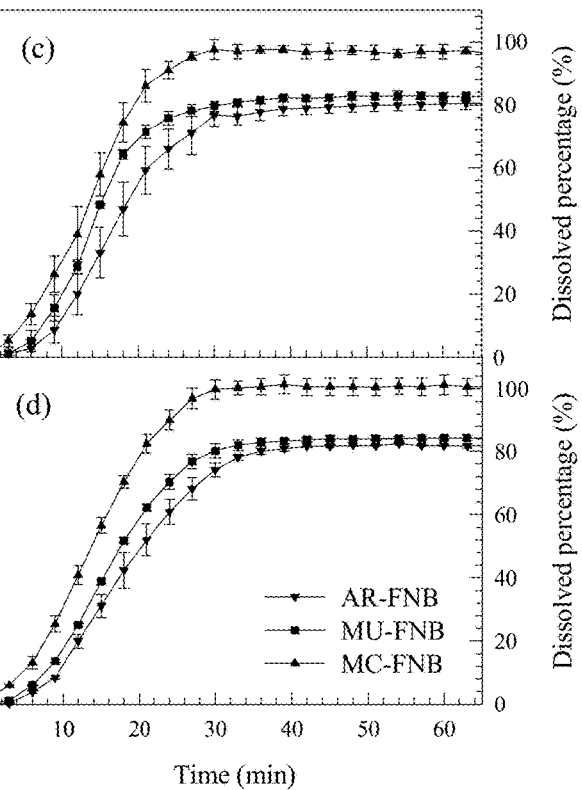
FIGURE 9B FIGURE 9D

500 μm   1000 μm   1500 μm   2000 μm

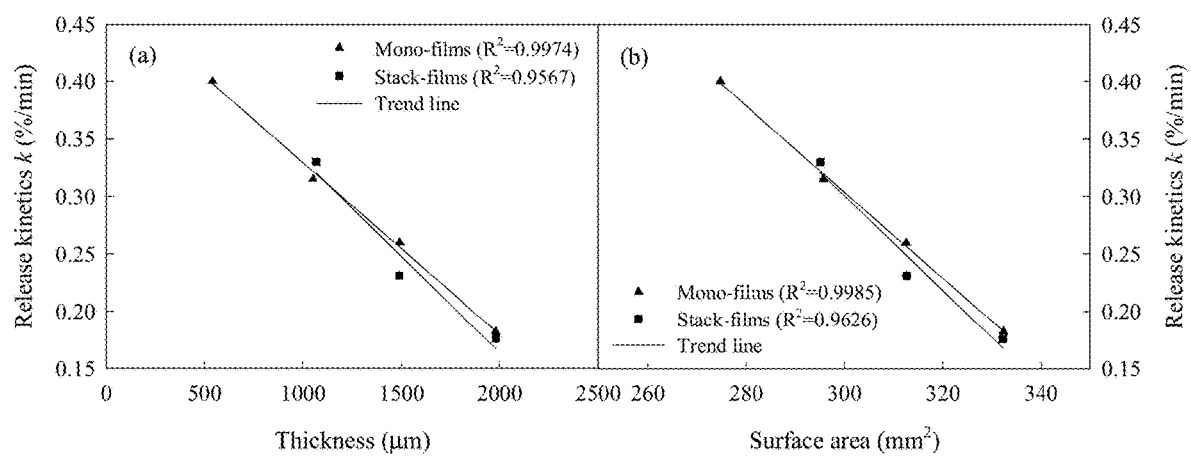
FIGURE 19A  FIGURE 19B

FIGURE 20A FIGURE 20B FIGURE 20C
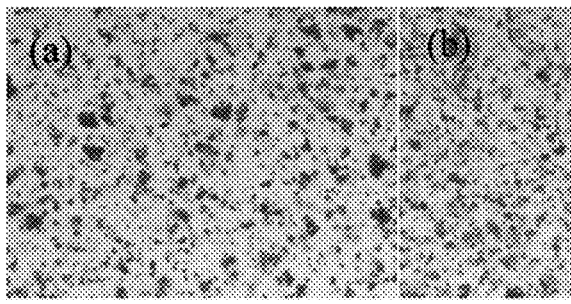 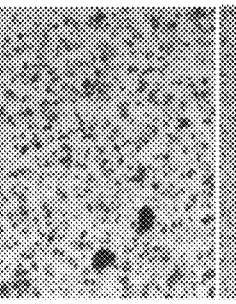 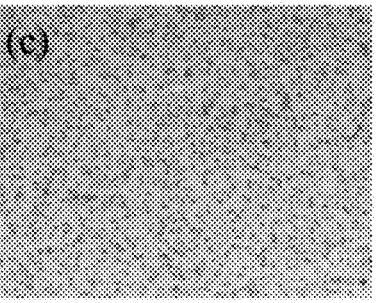
1% AR-DP  1% MU-DP  1% MC-DP
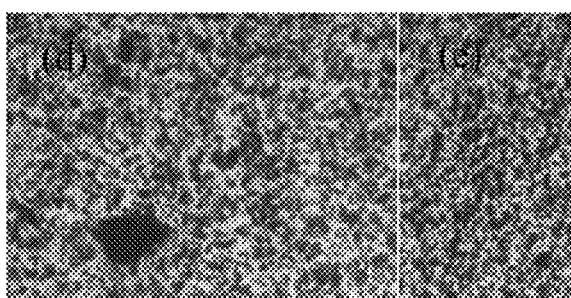 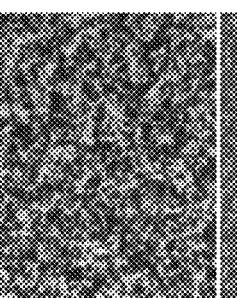 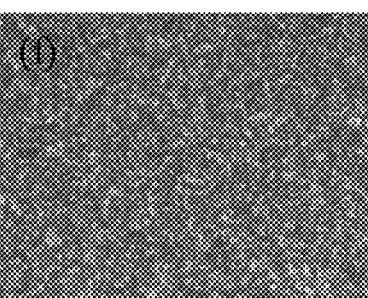
5% AR-DP  5% MU-DP  5% MC-DP
FIGURE 20D FIGURE 20E FIGURE 20F

FIGURE 21A
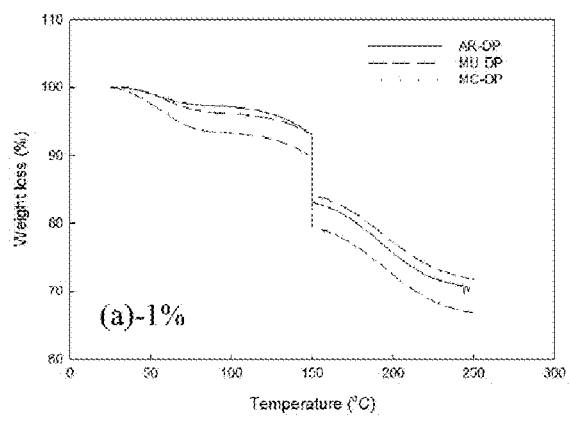
FIGURE 21B
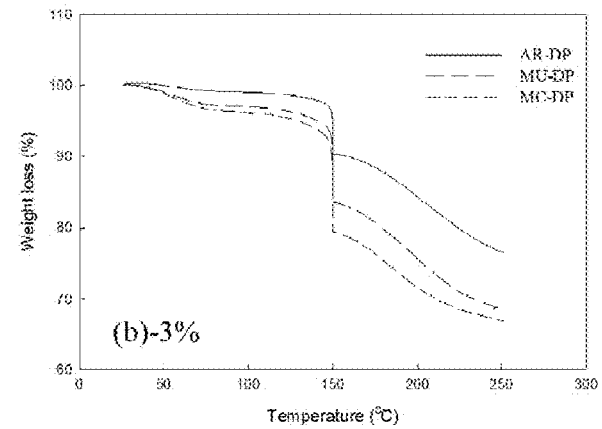
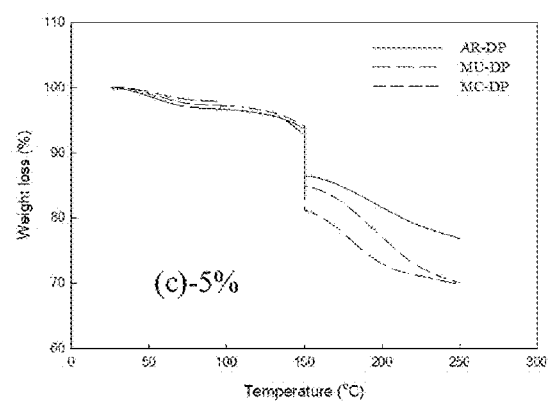
FIGURE 21C

FIGURE 22A   FIGURE 22B
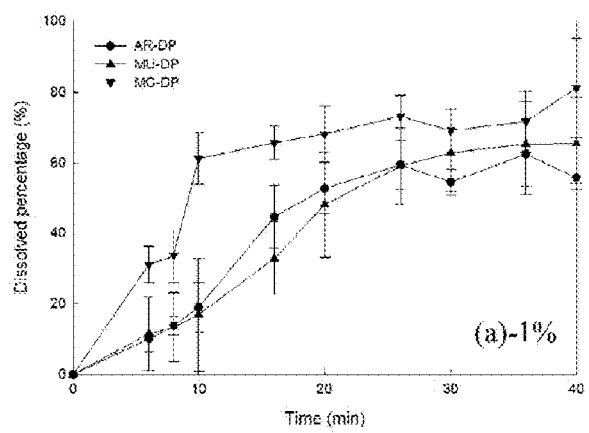 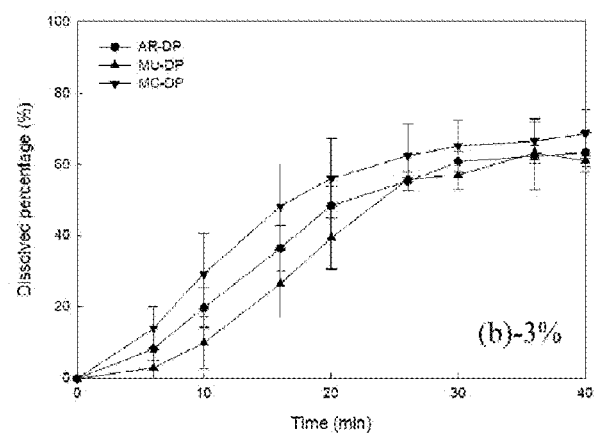
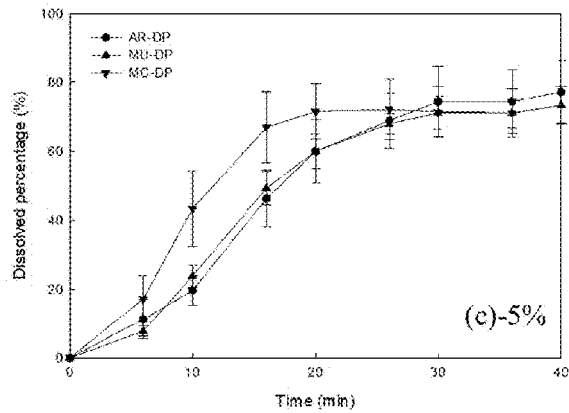
FIGURE 22C

FIGURE 24A                                    FIGURE 24B
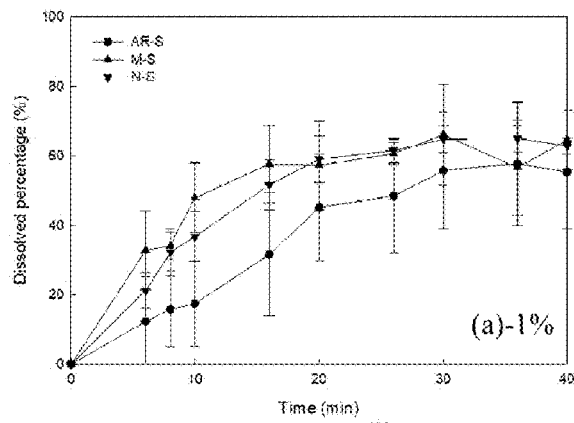
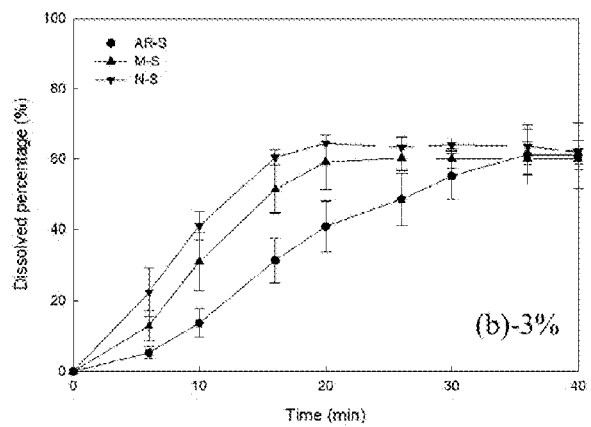
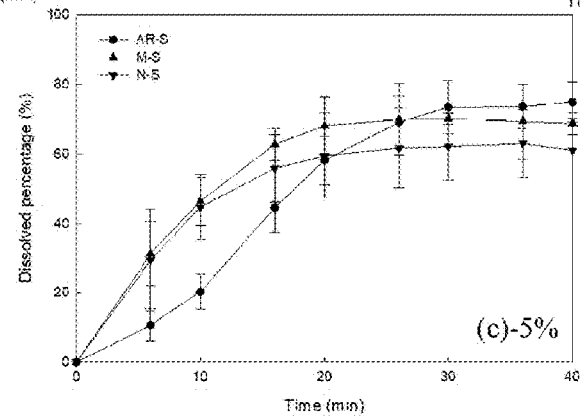
FIGURE 24C

FIG. 33A  FIG. 33B
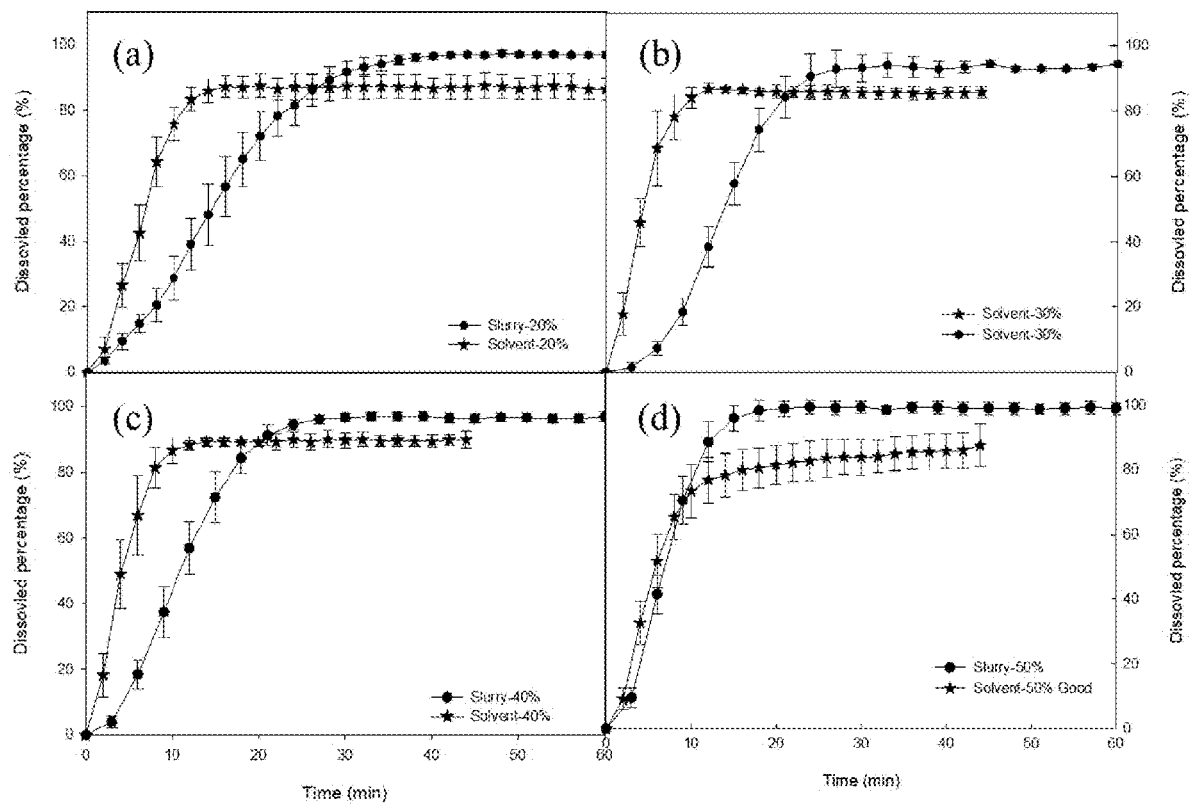
FIG. 33C  FIG. 33D

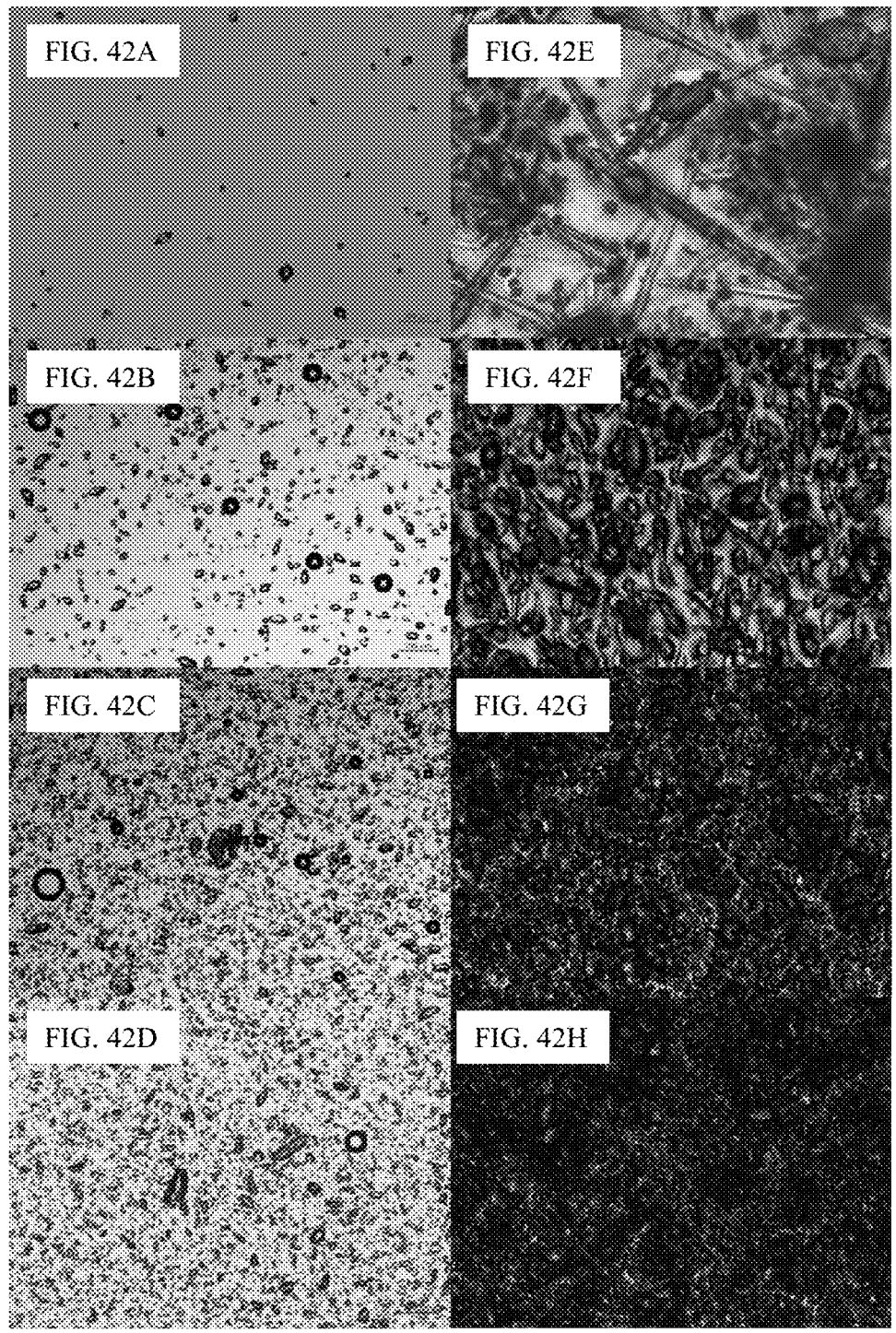

FIG. 43A            FIG. 43B
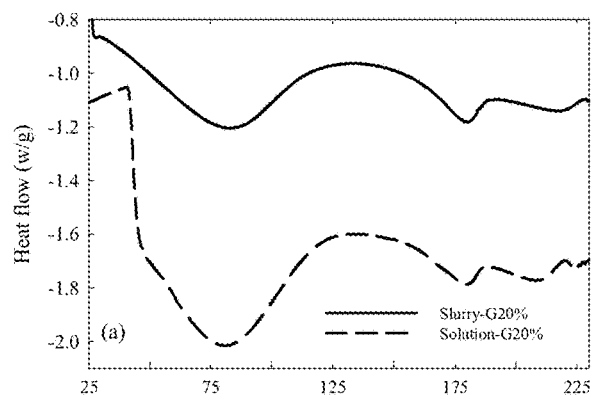
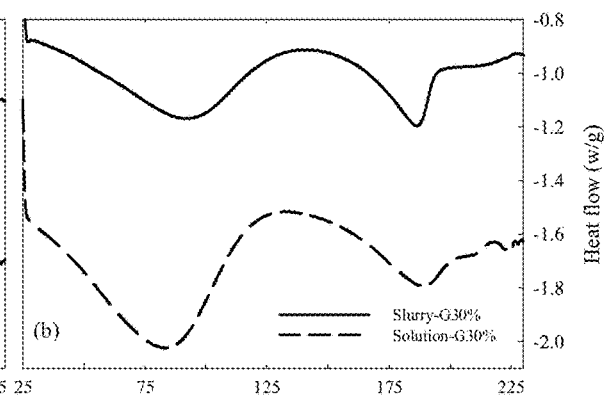
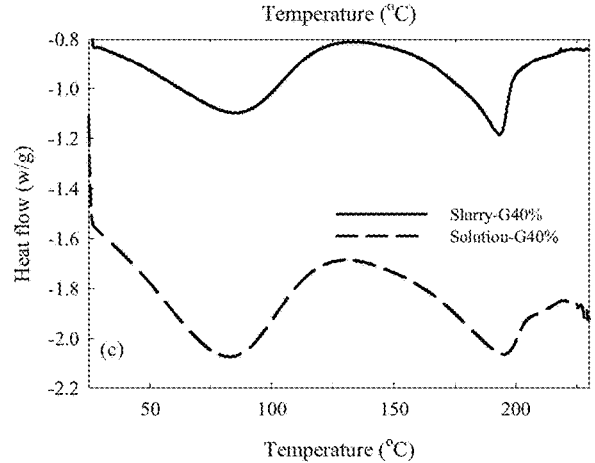
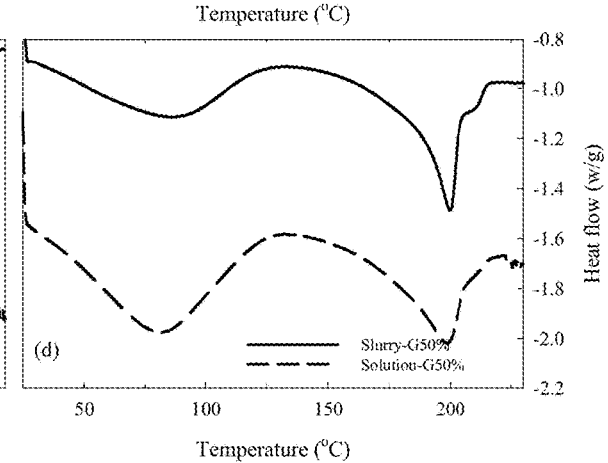
FIG. 43C            FIG. 43D

FIG. 46A         FIG. 46B
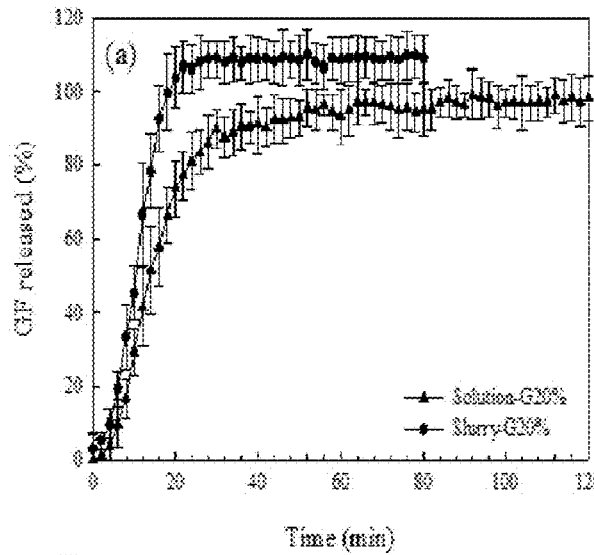 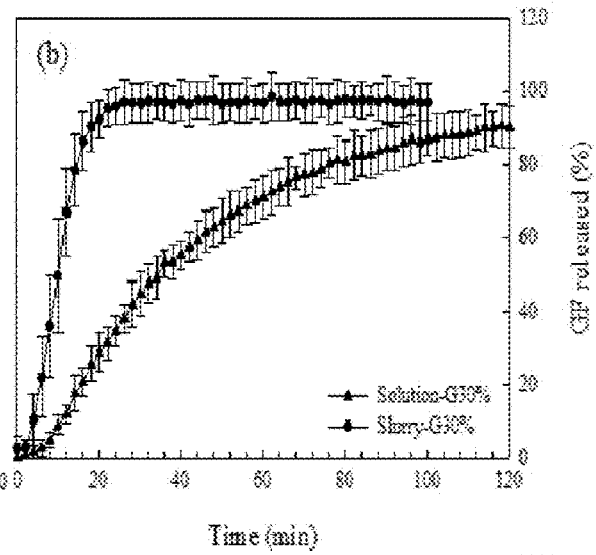
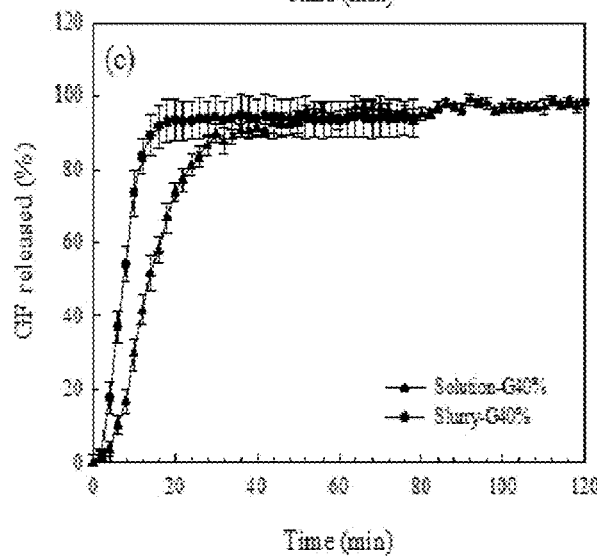 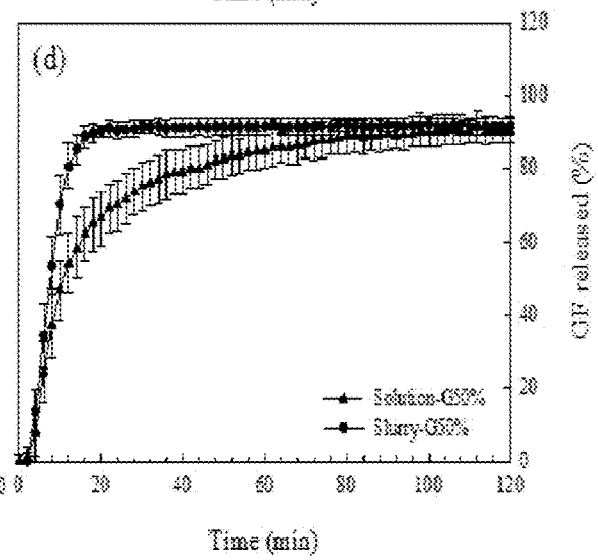
FIG. 46C         FIG. 46D FIG. 57A
FIG. 57B
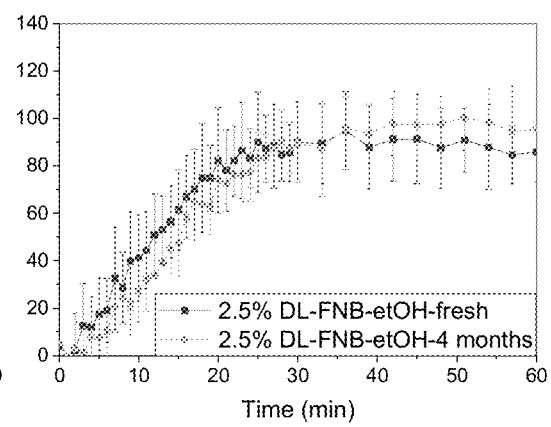
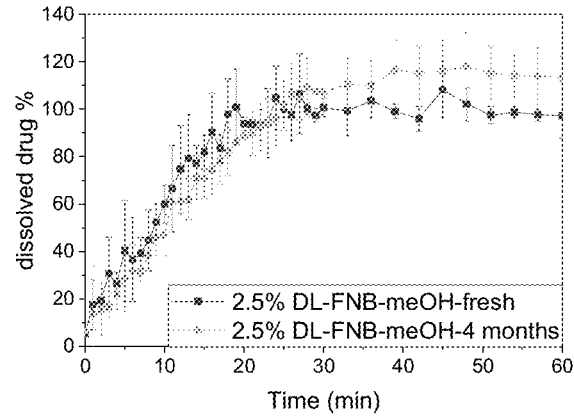
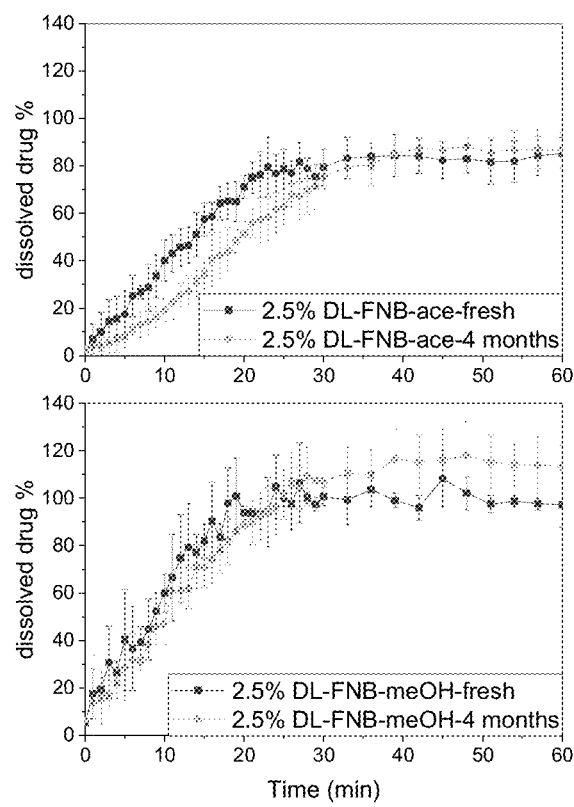
FIG. 57C

COMPOSITIONS AND METHODS FOR PREPARING POLYMERIC FILMS LOADED WITH UNIFORMLY DISTRIBUTED DRUG PARTICLES

CROSS-REFERENCE TO RELATED APPLICATIONS

This application claims the benefit of U.S. Provisional Application entitled "Compositions And Methods For Preparing Polymeric Films Loaded With Uniformly Distributed Drug Particles," which was filed on Oct. 3, 2017, and assigned Ser. No. 62/567,517, the contents of which are herein incorporated by reference in their entirety.

STATEMENT REGARDING FEDERALLY SPONSORED RESEARCH

This invention was made with government support under: (i) NSF Grant #EEC-0540855 awarded by the National Science Foundation, and (ii) NIH Grant #U01FD005521 awarded by the National Institutes of Health. The government has certain rights in the invention.

FIELD OF THE DISCLOSURE

The present disclosure relates to film based pharmaceutical products containing uniformly distributed drug or active agent particles (e.g., to achieve improved/excellent dissolution control including enhancing dissolution and bioavailability and/or product uniformity) and, more particularly, to improved systems and methods for fabricating film based pharmaceutical products by utilizing higher amounts of surface modified micronized drug or active agent powders and film forming precursors and drying methods that accomplish improved/efficient drying and provide improved/excellent content uniformity of active pharmaceutical agents, while retaining their form and size in the film based pharmaceutical products.

BACKGROUND OF THE DISCLOSURE

In general, orodispersible drug dosage forms are gaining popularity, particularly for pediatric and geriatric patients, as well as patients suffering from dysphagia or vomiting, due to the ease of handling and convenient application leading to high patient compliance. Polymeric films, one such relatively new dosage form, can also offer improved available surface area and can be amenable to easier precision dosing compared to drops or syrups. Additionally, film formulation can be readily adjusted to allow for customized disintegration and dissolution rate.

Some traditional approaches for preparing films with poorly water-soluble drugs are solvent casting and hot melt extrusion ("HME"). A weakness of solvent casting is that drug recrystallization may occur during drying, leading to drug loading limitations, poor drug particle size control and the instability of APIs in the products, along with the presence of residual solvents. HME, on the other hand, has been proposed as a solvent-free manufacturing process for films, in particular for poorly water-soluble drugs. However, it can require significant time in formulation development, particularly for drug loading beyond around 15 to 20 wt % and can pose limitations due to high-temperature processing, limiting the number of drugs that can be processed. Further, most extruders cannot produce films thin enough (e.g., less than 100 um) that can be required for fast disintegration; with their minimum thickness being around 254 to 305 um.

Some recent work reveals that films formed via aqueous slurry casting may have advantages over solvent and HME cast films for poorly water-soluble drugs. In this process, stable aqueous drug nanosuspensions are mixed with aqueous solution of polymer and plasticizer, preferably having high viscosity to prepare film precursors that are then cast and dried. Based on slurry casting, it has been demonstrated that film can be a promising, robust platform for the delivery of crystalline nanoparticles of poorly water-soluble drugs. It has been shown that this approach can be used to prepare high drug-loaded thin films with enhanced film critical quality attributes ("CQAs") such as drug content uniformity (relative standard deviation, "RSD %"), high drug load, film appearance, dissolution control, desired mechanical properties, stability of drug form and film performance, etc. However, these studies concerned the use of stable drug nanoparticle suspensions to prepare stripfilms via mixing, casting and drying.

In film literature using drug nanosuspensions, media milling is used, which can require high energy and long processing times and may pose manufacturing limitations, including high cost at production scales. In addition, surfactants and other additives are typically required during milling to achieve smaller size and to ensure drug nanosuspension stability. Other than potential for toxicity arising from the use of surfactants, there is also the risk of product contamination due to milling media wear. Considering these factors, one can question if nanomilling down to 200 nm is necessary to achieve good film CQAs. In fact, particles larger than 500 nm or low-micron sizes have been used to achieve acceptable results for some but not all of the desired film CQAs. Using liquid-antisolvent precipitation, films prepared with low-micron sizes of griseofulvin, a poorly water soluble drug, have been shown to achieve immediate release profiles and low RDS values, although at low drug loading (around 5 wt %). In other research, an interesting particle formation approach based on melt-emulsion of fenofibrate was used to prepare stable around 600 nm particle suspensions that led to immediate release of FNB at acceptable drug RSD, again at about 6 wt % drug loading. Interestingly, a less stable formulation in the same research achieved similar CQAs even when the drug particles were agglomerated to several microns size. Such results, both requiring use of surfactants, suggest that some but not all of the desired film CQAs may be achieved without using drug nanosuspensions.

Thus, an interest exists for improved systems and methods for improved film based pharmaceutical products. These and other inefficiencies and opportunities for improvement are addressed and/or overcome by the systems, assemblies and methods of the present disclosure.

SUMMARY OF THE DISCLOSURE

The present disclosure provides improved film based pharmaceutical products containing uniformly distributed drug or active agent particles (e.g., to achieve improved/ excellent dissolution control including enhancing dissolution and bioavailability and/or product uniformity). More particularly, the present disclosure provides improved systems/methods for fabricating film based pharmaceutical products by utilizing higher surface modified micronized drug or active agent powders and film forming precursors and drying methods that accomplish improved/efficient drying and provide improved/excellent content uniformity of active pharmaceutical agents in the fabricated film based pharmaceutical products.

Some exemplary systems and methods for fabricating stripfilm based pharmaceutical products are described and disclosed in U.S. Provisional Patent App. Ser. No. 61/791,752; PCT Patent App. Serial No. PCT/US2014/030506 and U.S. Non-Provisional patent application Ser. No. 14/777,191, the entire contents of each being hereby incorporated by reference in their entireties.

Recent work has established polymer strip films as a robust platform for delivery of poorly water-soluble drugs using their stabilized drug nanosuspensions. In exemplary embodiments, the present disclosure provides for an easier means of directly incorporating dry micronized poorly water-soluble drugs or active agent particles (e.g., fenofibrate ("FNB")) into films.

In certain embodiments, fine surface modified FNB ("MC-FNB") powders were obtained via simultaneous micronization and surface modification with hydrophilic silica using a fluid energy mill ("FEM"). It is noted that surface coating promotes easy and more uniform dispersion of MC-FNB via direct mixing with film precursors, positively impacting film critical quality attributes ("CQAs"). Aqueous film precursors were made using hydroxypropyl methylcellulose (HPMC-E15LY) as a film former and glycerin as a plasticizer. The impacts of film precursor viscosity, low versus high shear mixing, and FNB surface modification on CQAs of the film product were assessed. Films with as-received FNB (AR-FNB) and milled/uncoated FNB (MU-FNB) were prepared as controls.

When lower-shear impeller mixing and low film precursor viscosity were used, use of MC-FNB was important to achieve superior CQAs; e.g., appearance (thickness uniformity, visible lumps/agglomerates), drug content uniformity (RSD %), and mechanical properties (ultimate tensile strength, elongation percentage, Young's modulus).

Importantly, use of MC-FNB led to improved drug particle size recovery upon redispersion and fast, substantially complete drug release. Generally, the high-shear planetary mixer resulted in better film CQAs. The results demonstrate advantages of direct incorporation of surface modified-micronized poorly water-soluble drug powders in film manufacturing.

The present disclosure provides for a method for fabricating a film based pharmaceutical product including providing dry active agent particles; micronizing the dry active agent particles and surface modifying the dry active agent particles with a dry coating agent via dry milling to obtain micronized active agent particles surface coated with the coating agent, the micronized active agent particles surface coated with the coating agent in dry powder form; mixing the micronized active agent particles surface coated with the coating agent in dry powder form with at least one film forming precursor to form a mixture; and drying and fabricating the mixture to form a film.

The present disclosure also provides for a method for fabricating a film based pharmaceutical product wherein the step of micronizing the dry active agent particles and surface modifying the dry active agent particles with a dry coating agent via dry milling to obtain micronized active agent particles surface coated with the coating agent includes simultaneously micronizing the dry active agent particles and surface modifying the dry active agent particles with a dry coating agent via dry milling to obtain micronized active agent particles surface coated with the coating agent.

The present disclosure also provides for a method for fabricating a film based pharmaceutical product wherein the dry coating agent includes hydrophilic silica.

The present disclosure also provides for a method for fabricating a film based pharmaceutical product wherein the dry active agent particles are simultaneously micronized and surface modified with the dry coating agent via a fluid energy mill.

The present disclosure also provides for a method for fabricating a film based pharmaceutical product wherein the at least one film forming precursor includes hydroxypropyl methylcellulose and glycerin. The present disclosure also provides for a method for fabricating a film based pharmaceutical product wherein the dry active agent particles include BCS Class II poorly water-soluble drug particles or BCS Class IV poorly water-soluble drug particles.

The present disclosure also provides for a method for fabricating a film based pharmaceutical product wherein the micronized active agent particles surface coated with the coating agent are directly mixed with the at least one film forming precursor to form the mixture.

The present disclosure also provides for a method for fabricating a film based pharmaceutical product wherein the micronized active agent particles surface coated with the coating agent are directly mixed with the at least one film forming precursor via a mixer to form the mixture, the mixer selected from the group consisting of a planetary mixer, an impeller mixer, a high intensity vibratory mixer and a twin screw extruder.

The present disclosure also provides for a method for fabricating a film based pharmaceutical product wherein the dry coating agent is selected from the group consisting of hydrophilic silica, silica, a surfactant, a lipid, lecithin, a wetting agent, and combinations thereof. The present disclosure also provides for a method for fabricating a film based pharmaceutical product wherein the dry coating agent is dry coated to the micronized active agent particles.

The present disclosure also provides for a method for fabricating a film based pharmaceutical product wherein the mixture has a viscosity of from about 5,000 cP to about 18,500 cP. The present disclosure also provides for a method for fabricating a film based pharmaceutical product wherein the mixture includes a surfactant. The present disclosure also provides for a method for fabricating a film based pharmaceutical product wherein the at least one film forming precursor is a polymer solution.

The present disclosure also provides for a method for fabricating a film based pharmaceutical product wherein the micronized active agent particles include one or more particles having a particle size of about 4.2 μm. The present disclosure also provides for a method for fabricating a film based pharmaceutical product wherein the film has a tensile strength of from about 21.7 MPa to about 35.8 MPa.

The present disclosure also provides for a method for fabricating a film based pharmaceutical product wherein the dry active agent particles include pharmaceutical active agent particles; and wherein the film is formed by solution casting or slurry casting the mixture.

The present disclosure also provides for a method for fabricating a film based pharmaceutical product further including the step of re-dispersing the fabricated film in a medium to form a re-dispersion; wherein the micronized active agent particles, prior to mixing with the at least one film forming precursor, have a first D50 particle size distribution value and the re-dispersion of the fabricated film in the medium has a second D50 particle size distribution value, the first and second D50 particle size distribution values varying from one another by about 10% or less.

The present disclosure also provides for a method for fabricating a film based pharmaceutical product including providing dry active agent particles; micronizing the dry active agent particles and surface modifying the dry active agent particles with a dry coating agent via dry milling to obtain micronized active agent particles surface coated with the coating agent, the micronized active agent particles surface coated with the coating agent in dry powder form; mixing the micronized active agent particles surface coated with the coating agent in dry powder form with at least one film forming precursor to form a mixture; and drying and fabricating the mixture to form a film; wherein the dry active agent particles are simultaneously micronized and surface modified with the dry coating agent via a fluid energy mill; wherein the dry active agent particles include poorly water-soluble drug particles; wherein the micronized active agent particles surface coated with the coating agent are directly mixed with the at least one film forming precursor to form the mixture; wherein the dry coating agent is dry coated to the micronized active agent particles; and wherein the at least one film forming precursor is a polymer solution.

The present disclosure also provides for a method for fabricating a film based pharmaceutical product wherein the step of micronizing the dry active agent particles and surface modifying the dry active agent particles with a dry coating agent via dry milling to obtain micronized active agent particles surface coated with the coating agent includes simultaneously micronizing the dry active agent particles and surface modifying the dry active agent particles with a dry coating agent via dry milling to obtain micronized active agent particles surface coated with the coating agent.

The present disclosure also provides for a method for fabricating a film based pharmaceutical product including providing dry active agent particles; simultaneously micronizing the dry active agent particles and surface modifying the dry active agent particles with a dry coating agent via dry milling to obtain micronized active agent particles surface coated with the coating agent, the micronized active agent particles surface coated with the coating agent in dry powder form; mixing the micronized active agent particles surface coated with the coating agent in dry powder form with at least one film forming precursor to form a mixture; and drying and fabricating the mixture to form a film; wherein the dry active agent particles are simultaneously micronized and surface modified with the dry coating agent via a fluid energy mill; wherein the dry active agent particles include poorly water-soluble drug particles; wherein the micronized active agent particles surface coated with the coating agent are directly mixed with the at least one film forming precursor via a planetary mixer or an impeller mixer to form the mixture; wherein the dry coating agent is dry coated to the micronized active agent particles; wherein the at least one film forming precursor is a polymer solution; wherein the dry coating agent includes hydrophilic silica; wherein the mixture has a viscosity of from about 5,000 cP to about 18,500 cP; and wherein the micronized active agent particles include one or more particles having a particle size of about 4.2 μm.

The present disclosure also provides for methods for fabricating thick films (e.g., thick-film based pharmaceutical products) that have zero order release (e.g., once film thickness is above 500 microns). The present disclosure also provides for a method for fabricating a film based pharmaceutical product including continuous mixing, solution casting and/or slurry casting during fabrication.

Any combination or permutation of embodiments is envisioned. Additional advantageous features, functions and applications of the disclosed systems, assemblies and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the scope of the present disclosure. To assist those of ordinary skill in the art in making and using the disclosed systems, assemblies and methods, reference is made to the appended figures, wherein:

FIGS. 2A-2C show scanning electron microscopy (SEM) images of AR-FNB particles (FIG. 2A), MU-FNB particles (FIG. 2B), and MC-FNB particles (FIG. 2C);

FIGS. 3A-3F depict digital microscopy morphology images of dry films produced by impeller mixer; low viscosity precursor: (FIG. 3A) Film with AR-FNB; (FIG. 3B) Film with MU-FNB; (FIG. 3C) Film with MC-FNB; High viscosity precursor: (FIG. 3D) Film with AR-FNB; (FIG. 3E) Film with MU-FNB; (FIG. 3F) Film with MC-FNB.

FIGS. 9A-9D show film dissolution profiles of films loaded with AR-FNB, MU-FNB and MC-FNB in 100 ml dissolution medium; Low viscosity: (FIG. 9A) impeller mixer; (FIG. 9B) planetary mixer; High viscosity: (FIG. 9C) impeller mixer; (FIG. 9D) planetary mixer;

(FIG. 10A) Film loaded with AR-FNB; (FIG. 10B) Film loaded with MU-FNB;

FIGS. 11A-11F show digital microscopy morphology images of dry films produced by planetary mixer; Low viscosity precursor: (FIG. 11A) Film with AR-FNB; (FIG. 11B) Film with MU-FNB; (FIG. 11C) Film with MC-FNB; High viscosity precursor: (FIG. 11D) Film with AR-FNB; (FIG. 11E) Film with MU-FNB; (FIG. 11F) Film with MC-FNB;

FIGS. 19A-19B show release kinetics constant, k, of Eq. (1) as a function of thickness (FIG. 19A) and surface area (FIG. 19B) of monolithic thick films and stacked films;

FIGS. 20A-20F show the optical microscope images of films with as-received dry particle (AR-DP), micronized uncoated dry particles (MU-DP), micronized silica coated dry particles (MC-DP) at 1% and 5% drug loadings;

FIGS. 21A-21C show the water weight loss (%) between different films;

FIGS. 22A-22C show the dissolution profiles of exemplary films;

FIGS. 24A-24C show the dissolution profiles of exemplary films;

FIG. 26A is AR-FNB, FIG. 26B is MU-FNB, and FIG. 26C is MC-FNB;

FIG. 27A is thickness and FIG. 27B is drug dose per unit area;

FIG. 28A is 20%, FIG. 28B is 30%, FIG. 28C is 40%, and FIG. 28D is 50%;

FIG. 31A is 20%, FIG. 31B is 30%, FIG. 31C is 40%, and FIG. 31D is 50%;

FIG. 32A is 30%, and FIG. 32B is 40%;

FIGS. 33A-D show dissolution profiles of slurry and solution films: FIG. 33A is 20%; FIG. 33B is 30%; FIG. 33C is 40%; and FIG. 33D is 50%;

FIG. 34A shows tensile strength, FIG. 34B shows elongation at break, and FIG. 34C shows Young's modulus;

FIGS. 42A-42H show optical digital microscope images of GF film precursors and dry films via solution casting: Precursors: FIG. 42A is 20 wt %, FIG. 42B is 30 wt %, FIG. 42C is 40 wt %, and FIG. 42D is 50 wt %; Dry films: FIG. 42E is 20 wt %, FIG. 42F is 30 wt %, FIG. 42G is 40 wt %, and FIG. 42G is 50 wt %;

FIGS. 43A-43D show DSC curves of solution and slurry GF films at different drug loadings;

FIG. 44A is 20 wt %, FIG. 44B is 30 wt %, FIG. 44C is 40 wt %, FIG. 44D is 50 wt %;

FIG. 45A is tensile strength, FIG. 45B is elongation at break, FIG. 45C is Young's modulus;

FIGS. 46A-46D show dissolution profiles of slurry films and solution films laden with GF: FIG. 46A is 20 wt %, FIG. 46B is 30 wt %, FIG. 46C is 40 wt %, FIG. 46D is 50 wt %;

FIGS. 47A-47C show pictures of films loaded with 10% FNB prepared using 1:4 (w:etOH) as solvent dried at: FIG. 47A is at 50° C.; FIG. 47B is at 40° C.; and FIG. 47C is at 30° C.;

FIGS. 56A-55C show a comparison of dissolution profiles of fresh and three months old films prepared with different solvents (LC=2.5% GF); and FIGS. 57A-57C show a comparison of dissolution profiles of fresh and four months old films prepared with different solvents (LC=2.5% FNB).

DETAILED DESCRIPTION OF DISCLOSURE

Figure 1:
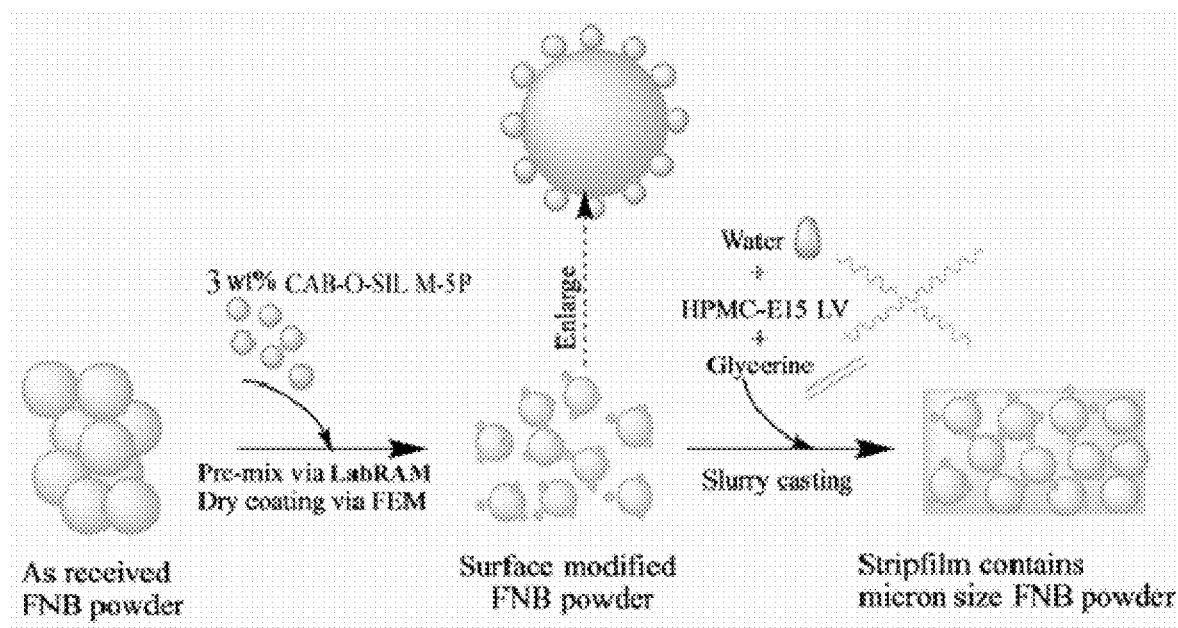
FIG. 1 shows a graphical representation of the preparation of a film loaded with FNB dry powders.

The following is a detailed description of the disclosure provided to aid those skilled in the art in practicing the present disclosure. Those of ordinary skill in the art may make modifications and variations in the embodiments described herein without departing from the scope of the present disclosure. Unless otherwise defined, the technical and scientific terms used herein have the same meaning as commonly understood by one of ordinary skill in the art. The terminology used in the description of the disclosure herein is for describing particular embodiments only, and is not intended to be limiting of the disclosure. All publications, patent applications, patents, figures and other references mentioned herein are expressly incorporated by reference in their entireties.

The exemplary embodiments disclosed herein are illustrative of advantageous film based pharmaceutical products, and systems of the present disclosure and methods/techniques thereof. It should be understood, however, that the disclosed embodiments are merely exemplary of the present disclosure, which may be embodied in various forms. Therefore, details disclosed herein with reference to exemplary film based pharmaceutical products/fabrication methods and associated processes/techniques of assembly and use are not to be interpreted as limiting, but merely as the basis for teaching one skilled in the art how to make and use the advantageous film based pharmaceutical products/systems and/or alternative products/assemblies of the present disclosure.

The present disclosure provides improved film based pharmaceutical products containing uniformly distributed drug or active agent particles (e.g., to achieve improved/excellent dissolution control including enhancing dissolution and bioavailability and/or product uniformity). More particularly, the present disclosure provides improved systems/methods for fabricating film based pharmaceutical products by utilizing higher surface modified micronized drug or active agent powders and film forming precursors and drying methods that accomplish improved/efficient drying and provide improved/excellent content uniformity of active pharmaceutical agents in the fabricated film based pharmaceutical products.

As noted, some exemplary systems and methods for fabricating stripfilm based pharmaceutical products are described and disclosed in U.S. Provisional Patent App. Ser. No. 61/791,752; PCT Patent App. Serial No. PCT/US2014/030506 and U.S. Non-Provisional patent application Ser. No. 14/777,191, the entire contents of each being hereby incorporated by reference in their entireties.

Polymer strip films can be a robust platform for delivery of poorly water-soluble drugs using their stabilized drug nanosuspensions. In exemplary embodiments, the present disclosure provides for an easier means of directly incorporating dry micronized poorly water-soluble drugs or active agent particles (e.g., fenofibrate ("FNB")) into films.

In certain embodiments, micronized surface modified active agent powders (e.g., fine surface modified FNB or "MC-FNB" powders) were obtained via simultaneous micronization and surface modification with a coating agent (e.g., hydrophilic silica; silica; surfactants; lipids; lecithin; wetting agents; combinations thereof; etc.) using a fluid energy mill ("FEM"). It is noted that surface coating promotes easy and more uniform dispersion of micronized surface modified active agent powders (e.g., MC-FNB) via direct mixing with film precursors, positively impacting film CQAs. Aqueous film precursors were made using hydroxypropyl methylcellulose (HPMC-E15LV) as a film former and glycerin as a plasticizer. The impacts of film precursor viscosity, low versus high shear mixing, and FNB surface modification on CQAs of the film product were assessed. Films with as-received FNB (AR-FNB) and milled/uncoated FNB (MU-FNB) were prepared as controls.

When lower-shear impeller mixing and low film precursor viscosity were used, use of MC-FNB was important to achieve superior CQAs; e.g., appearance (thickness uniformity, visible lumps/agglomerates), drug content uniformity (RSD %), and mechanical properties (ultimate tensile strength, elongation percentage, Young's modulus).

It is noted that the use of MC-FNB led to improved drug particle size recovery upon redispersion and fast, substantially complete drug release. Generally, the high-shear planetary mixer resulted in better film CQAs. The results demonstrate advantages of direct incorporation of surface modified-micronized poorly water-soluble drug powders in film manufacturing.

One objective of the present disclosure was to examine the use of dry milling to achieve very fine/micronized drug powders as an alternate to wet milling in the film formation process without negatively affecting film CQAs. However, sometimes micronization can lead to downstream problems attributed to their poor flow, severe agglomeration and poor dispersion, hence, failing to achieve expected dissolution rate enhancements. Poor flow and agglomeration are expected to lead not only to difficulties in handling, but also in mixing of dry agglomerated hydrophobic drug particles with aqueous solution of polymer and plasticizer. Fortunately, severe agglomeration may be tackled using a novel simultaneous surface modification and micronization method where coating agents/additives such as hydrophilic silica may be dry coated using the fluid energy mill ("FEM"). It has been shown that ibuprofen powders may be micronized down to about 5 or 10 μm and simultaneously dry coated with hydrophilic silica to greatly enhance flow, packing, dispersion and importantly, dissolution from micronized powders. It has also been shown that micronized and surface modified ibuprofen powders provide excellent flow properties for 60% drug loaded blends and very fast dissolution from their tablets. However, the effectiveness of hydrophilic silica on the surface of dry surface modified-micronized hydrophobic drug particles for their direct mixing with aqueous film precursors has not been previously examined.

Consequently, incorporation of micronized and surface modified drug powders (e.g., BCS Class II poorly water-soluble drug particles, or BCS Class IV poorly water-soluble drug particles) in to film formulations was considered in this disclosure. Fenofibrate, a BCS Class II drug, was used as the model drug and micronization was carried out in a FEM with or without surface modification with hydrophilic silica, MSP. Two additional factors, the mixer type (a high-shear planetary mixer and a low-shear impeller mixer) and the viscosity of the polymer solution (5,000 cP and 15,000 cP) were also investigated due to their potential impact on film CQAs. Overall, a systematic investigation was performed to test the hypothesis that surface modified micronized powders may be directly incorporated to manufacture films with enhanced CQAs such as content uniformity, dissolution and mechanical properties. In addition, the impact of the viscosity of the polymer solution as well as the type of mixer was evaluated.

The present disclosure will be further described with respect to the following examples; however, the scope of the disclosure is not limited thereby. The following examples illustrate the improved systems/methods of the present disclosure of fabricating advantageous film based pharmaceutical products containing uniformly distributed drug or active agent particles.

More particularly, the following examples illustrate the advantageous systems/methods of the present disclosure of fabricating film based pharmaceutical products by utilizing higher surface modified micronized drug or active agent powders and film forming precursors and drying methods that accomplish improved/efficient drying and provide improved/excellent content uniformity of active pharmaceutical agents in the fabricated film based pharmaceutical products.

Example 1: The Effect of Surface-Modified Dry Micronized Powders of Poorly Water Soluble Drug on Critical Quality Attributes (CQAs) of Polymer Strip Films Processed by an Impeller Mixer Materials:

Fenofibrate (FNB; Jai Radhe Sales, Ahmedabad, India) was selected as a model BCS Class II poorly water-soluble drug. Pharmaceutical grade amorphous hydrophilic silica (M5P, Cabot Corporation, MA) with primary particle size of 16 nm was used as the coating material for dry FNB particles. Low molecular weight hydroxypropyl methylcellulose (HPMC; Methocel E15 Premium LV, $M_w$ around 40,000, The Dow Chemical Company, Midland, Mich.) and glycerin (Sigma-Aldrich, Saint Louis, Mo.) were used as the film former and the film plasticizer, respectively. Sodium dodecyl sulfate (SDS) (Sigma-Aldrich, Saint Louis, Mo.) was used as the surfactant in the dissolution media. The FNB particles with or without M5P processed via a FEM (qualification model, Sturtevant Inc., Hanover, Mass.) were referred to as MC-FNB and MU-FNB particles, respectively. The other materials were used as received.

Preparation of Milled/Coated and Milled/Uncoated Powders:

The detailed procedures for pre-mixing of powders via a Laboratory Resonant Acoustic Mixer (LabRAM; Resodyn Acoustic Mixers, Inc., Butte, Mont.), a high-intensity vibrational mixer, and preparation of dry coated and uncoated powders using FEM have been established and were followed here (see, e.g., Davé et al., 2011, *Particle engineering via dry coating: development of a novel material sparing technology for pharmaceutical powders*, AiChe Annual Meeting, Pittsburgh; and Han et al., 2011, *Simultaneous micronization and surface modification for improvement of flow and dissolution of drug particles*, International Journal of Pharmaceutics 415, 185-195).

As received FNB powder did not require any secondary pre-milling. Pre-mixing of FNB powder (97 g) and M5P (3 g) was performed in the LabRAM by placing the powder in a plastic cylindrical jar. The pre-mixing process operated at a frequency of 61 Hz with an acceleration of 70 G for 5 min to ensure that the silica particles were well distributed and attached to FNB particles. The MU-FNB particles were prepared without a pre-mixing step, and FNB powders were fed directly into the FEM.

Simultaneous micronization and surface modification was achieved through a FEM process as follows. The powder feeding rate was controlled by a volumetric feeder (Model 102M, Schenck Accurate, WI, USA) at a rate of 1 g/min. A constant feeding pressure (FP) of 45 psi and constant grinding pressure (GP) of 40 psi were maintained. Processed powders were stored in a vacuum desiccator at room temperature for subsequent scanning electron microscopy (SEM) and particle size tests.

Preparation of FNB Microparticle-Laden Films:

The method for incorporation of nano drug particles into HPMC films by slurry casting has been discussed in previous work (Sievens-Figueroa et al., 2012, *Preparation and characterization of hydroxypropyl methyl cellulose films containing stable BCS Class II drug nanoparticles for pharmaceutical applications*, Int J Pharm 423, 496-508).

Slurry casting involved the preparation of a polymer solution followed by an addition of drug substances, and the resulting film precursor was passed through a Doctor Blade (3700, Elcometer, MI, USA). A novel difference in the present disclosure is that the drug substance was used in dry powder form in contrast to stable aqueous suspension form, which was required in previous work. This major departure led to examination of the effect of the viscosity of the polymer solution and the type of mixers, since they were expected to impact aggregation and settling of drug particles.

The viscosity was controlled by through two different levels of polymer loading. The low viscosity aqueous formulation contained 12% HPMC-E15LV (wt %) and 4% glycerin (wt %), and the high viscosity aqueous formulation contained 17% HPMC-E15LV (wt %) and 5% glycerin (wt %).

The resulting polymer solutions and as-received fenofibrate particles (AR-FNB), micronized fenofibrate particles (MU-FNB), or surface-modified micronized fenofibrate particles (MC-FNB) were added in a 5:1 ratio and mixed for 3 hours using an impeller mixer (RW16, IKA, USA). The mixed low viscous FNB-polymer precursor (about 11,500 to 13,000 cp) and high viscous FNB-polymer precursor (about 17,000 to 18,500 cp) were cast at 900 to 1000 microns using a doctor blade (3700, Elcometer, USA) and dried in a drier chamber (TC-71LC, HED International, NJ, USA).

FIG. 1 shows the schematic of the preparation of FNB loaded films, and Table 1 below shows composition of polymer formulations.

In each case, the film precursor was cast on a plastic substrate (Scotchpak™ 9744, 3M, MN, USA) using a Doctor Blade (3700, Elcometer, MI, USA). The casting thickness was set in the range 900 to 1000 microns. The cast film was then dried at 50° C. in a batch mode under laminar air flow for 40 to 60 min in the tape casting equipment (TC-71LC, HED International, NJ, USA) capable of providing simultaneous conductive and convective drying.

TABLE 1

Composition of the polymer solution and the types of mixer:

| Run No. | Sample | Viscosity level | Mixing methods | HPMC E-15LV (g) | Glycerin (g) | DI water (g) |
|---|---|---|---|---|---|---|
| 1 | AR-FNB | Low | Impeller | 12 | 4 | 84 |
| 2 | MU-FNB | Low | Impeller | 12 | 4 | 84 |
| 3 | MC-FNB | Low | Impeller | 12 | 4 | 84 |
| 4 | AR-FNB | Low | Planetary | 12 | 4 | 84 |
| 5 | MU-FNB | Low | Planetary | 12 | 4 | 84 |
| 6 | MC-FNB | Low | Planetary | 12 | 4 | 84 |
| 7 | AR-FNB | High | Impeller | 17 | 5 | 78 |
| 8 | MU-FNB | High | Impeller | 17 | 5 | 78 |

TABLE 1-continued

Composition of the polymer solution and the types of mixer:

| Run No. | Sample | Viscosity level | Mixing methods | HPMC E-15LV (g) | Glycerin (g) | DI water (g) |
|---|---|---|---|---|---|---|
| 9 | MC-FNB | High | Impeller | 17 | 5 | 78 |
| 10 | AR-FNB | High | Planetary | 17 | 5 | 78 |
| 11 | MU-FNB | High | Planetary | 17 | 5 | 78 |
| 12 | MC-FNB | High | Planetary | 17 | 5 | 78 |

AR—as received;
MU—milled/uncoated;
MC—milled/coated;
Fixed drug loading of dry film-20% (wt %)
Polymer solution:
Low viscosity level-9000 cP;
High viscosity level-15000 cP Particle Size Distribution of Dry FNB Particles and after Re-Dispersion from Dried Films:

The particle size distribution of dry powder was measured via the laser diffraction technique (Rodos/Helos system, Sympatec, NJ, USA) where the D50 and the D90 size statistics were reported at 0.5 bar Rodos dispersion pressure. AR-FNB, MU-FNB and MC-FNB particles were tested three times to characterize their particle size.

The size distribution of re-dispersed drug particles from dried films was assessed by a laser diffraction particle size analyzer (Coulter LS 13320, Beckman Coulter, FL, USA). To access the redispersibility of drug particles, samples of films using circular punches of 0.72 cm² in area were mixed with 3 to 5 ml deionized water by a digital vortex mixer (Fisher Scientific, USA) at 1500 rpm for 5 to 10 min. The resulting suspension was then analyzed as per previously established protocols (Krull et al., 2015, *Polymer strip films as a robust, surfactant-free platform for delivery of BCS Class II drug nanoparticles*, Int J Pharm 489, 45-57).

Viscosity:

The apparent shear viscosity of the polymer solutions and film precursor was measured with a rheometer (R/S-CC+, Brookfield Engineering, MA, USA) equipped with a shear rate-controlled coaxial cylinder (CC25) and a temperature controlled water jacket (Lauda Eco, Lauda-Brinkmann LP, NJ, USA). Both were recorded at a low shear rate (2.2 s$^{-1}$) and 25±0.5° C., representing the low-shear rate imparted during film casting at room temperature.

Determination of Drug Content and Uniformity in Films:

Previously established protocols for determining the drug content and uniformity were followed (Krull et al., 2015, *Polymer strip films as a robust, surfactant-free platform for delivery of BCS Class II drug nanoparticles*, Int J Pharm 489, 45-57). Ten circular samples around 0.72 cm² in area were punched randomly from a film sample of 8 cm×15 cm size and dissolved in 100 ml of 7.2 mg/ml SDS solution with continuous stirring for a minimum 3 h.

Despite being roughly ¹/₁₀$^{th}$ the size of a traditional film dosage, this smaller size was used to help elucidate differences in drug content uniformity between drug particle size, surface modification, polymer solution viscosity and film precursor mixing process conditions. A Thermo Scientific Evolution 300 UV-vi spectrophotometer (Thermo Fisher Scientific Inc., MA) was used to measure the UV absorbance at a wavelength of 290 nm of each dissolved sample and then the concentration was calculated according to the previously constructed calibration curve. The thickness of 10 random punches were measured using a digital micrometer (Mitutoyo Corporation, Kanagawa, Japan). The average and relative standard deviation (RSD) of dose per unit area, weight percentage of the drug in the film, and thickness were calculated for each set of 10 samples.

Mechanical Properties of the Films:

A Texture Analyzer (TA-XT Plus, Stable Microsystems, UK) was used to ascertain the effect of surface modification of drug particles, type of mixers and viscosity levels of polymer solution on the mechanical properties of films. Tensile strength (TS), Young's modulus (YM) and percentage elongation (E %) were calculated from the stress versus strain data. For such testing, 3 to 5 rectangular test strips were cut to a dimension of 50 mm×15 mm from a single film sample. The test strips were held between two clamps positioned at a distance of 3 cm and elongated at a constant speed of 1 mm/s until the breaking point (e.g., tensile failure). The average and standard deviation of TS, YM and E % were computed over three different tests.

Digital Optical Microscopy:

The optical imaging of the dry films laden with AR-FNB, MU-FNB or MC-FNB were captured using a digital optical microscope (VHX-100K, Keyence, Japan). In the test, sample films were cut to a dimension of 2 mm×3 mm, a common commercial strip film size and imaged with 50× resolution.

Scanning Electron Microscopy (SEM):

A field emission scanning electron microscope (FESEM) (LEO1530VP GEMINI, Carl Zeiss Inc., MA, USA) was used to examine the morphology of AR-FNB, MU-FNB, and MC-FNB particles, and the film loaded with MC-FNB. The drug particles were placed on carbon tape and then were coated with carbon by sputter coater (Bal-Tec MED 020 HR, Leica Microsystems, Germany) to enhance the conductivity while under the FESEM. The images of AR-FNB, MU-FNB, and MC-FNB particles were recorded. In addition to analysis of film structure and drug particles in the film, a small piece of film laden with MC-FNB was placed on an aluminum stub via carbon tape and carbon coated using a sputter coater prior to imaging. The cross-sectional images of select films were recorded.

Thermo-Gravimetric Analysis (TGA):

Thermo-gravimetric analysis (TGA) of placebo film and films with AR-FNB, MU-FNB or MC-FNB were performed using a TGA/DSC1/SF STAR$^e$ system (Mettler Toledo Inc., OH, USA).

In a standard ceramic crucible, 5 to 8 mg of film sample was heated under a nitrogen atmosphere from 25° C. to 150° C. at a constant rate of 10° C./min, maintained at 150° C. for 15 min, heated to 250° C. at a rate of 10° C./min, and finally cooled back to 25° C. at a rate of 10° C./min.

Differential Scanning Calorimetry (DSC):

A differential scanning calorimeter (DSC, Mettler Toledo, Inc., OH, USA) was used to determine the melting degree of AR-FNB, MC-FNB particles, and MC-FNB particles in the film. In a standard aluminum pan, 5 to 8 mg of films was heated under a nitrogen flow from 25° C. to 150° C. at a constant rate of 10° C./min, maintained at 150° C. for 15 min, heated to 250° C. at a rate of 10° C./min, and finally cooled back to 25° C. at a rate of 10° C./min.

X-Ray Diffraction (XRD):

X-ray diffraction was performed to determine the crystallinity of AR-FNB, MU-FNB and MC-FNB particles, placebo film and drug particles in the films. Diffraction patterns were acquired for analysis of amorphous/crystalline behavior of these samples using Philips X'Pert (Almelo, Netherlands), scanning a 2θ angle in the range 5 to 35° (0.01° step).

Dissolution:

Dissolution experiments of films laden with AR-FNB, MU-FNB and MC-FNB were performed using a flow-through cell dissolution apparatus (USP IV, Sotax, Switzerland) with cells of an internal diameter of 22.6 mm and 0.2 μm Pall HT Tuffryn membrane disc filters. Punched circular samples from each film with an area of 0.72 cm$^2$ were horizontally positioned in the cells with 3 g of glass beads at the bottom and 2 g of glass beads on the top.

100 ml or 250 ml dissolution media (7.2 mg/ml SDS aqueous solution) was circulated through cells at a flow rate of 16 ml/min with a constant temperature 37±0.5° C. Six circular samples were used and the average drug release was plotted as a function of time.

Statistical Analysis:

All calculations were performed using Microsoft Excel (Microsoft Office 2010, USA). Results for mechanical properties were expressed as mean±SD (standard deviation) while content uniformity results are expressed as mean with RSD % (relative standard deviation). Dissolution profiles were contrasted using similarity and difference factors f1 and f2 (Costa et al., 2003, *Comparison of dissolution profiles of Ibuprofen pellets*, Journal of Controlled Release 89, 199-212; Costa, 2001, *An alternative method to the evaluation of similarity factor in dissolution testing*, Int J Pharm 220, 77-83; Costa et al., 2001, *Modeling and comparison of dissolution profiles*, European Journal of Pharmaceutical Sciences 13, 123-133).

Polymer Solution and Precursor Suspension Viscosities:

As expected, an increase in HPMC concentration led to an increase in viscosity. Accordingly, 12% and 17% HPMC concentration corresponded to 9,018 cP and 15,643 cP for "low level" and "high level" viscosity polymer solutions, respectively. As discussed, reasonable levels of viscosity were necessary to ensure film precursors could be cast easily, neither spreading too easily at low viscosities nor too viscous to cast at very high viscosities. As may be expected, the viscosities of film precursor increased to 11,500 to 13,000 cp and 17,000 to 18,500 cp, respectively, after adding dry FNB particles. No significant difference was found between film precursors with AR-FNB, MU-FNB, and MC-FNB with regard to viscosity.

TABLE 2

Relative standard deviation values of film thickness and drug dose per unit area of films containing AR-FNB, MU-FNB and MC-FNB:

| Run No. | Sample | Viscosity level | Mixing method | Thickness RSD % | Drug mass per unit area RSD % |
|---|---|---|---|---|---|
| 1 | AR-FNB | Low | Impeller | 16.12 | 11.37 |
| 2 | MU-FNB | Low | Impeller | 18.91 | 10.65 |
| 3 | MC-FNB | Low | Impeller | 8.58 | 7.29 |
| 4 | AR-FNB | Low | Planetary | 6.68 | 5.8 |
| 5 | MU-FNB | Low | Planetary | 7.08 | 5.14 |
| 6 | MC-FNB | Low | Planetary | 3.04 | 3.49 |
| 7 | AR-FNB | High | Impeller | 9.04 | 7.42 |
| 8 | MU-FNB | High | Impeller | 11.31 | 7.02 |
| 9 | MC-FNB | High | Impeller | 3.87 | 4.07 |
| 10 | AR-FNB | High | Planetary | 3.1 | 4.75 |
| 11 | MU-FNB | High | Planetary | 3.99 | 4.19 |
| 12 | MC-FNB | High | Planetary | 4.89 | 4.67 |

TABLE 3

Mechanical properties of the strip films with different dry powders:

| Run no. | Sample | Viscosity level | Mixing method | Tensile strength (MPa) | Young's modulus (GPa) | Percentage elongation (%) |
|---|---|---|---|---|---|---|
| 1 | AR-FNB | Low | Impeller | 25.62 ± 1.39 | 1.88 ± 0.08 | 6.26 ± 0.78 |
| 2 | MU-FNB | Low | Impeller | 21.11 ± 1.02 | 1.47 ± 0.08 | 4.56 ± 0.91 |
| 3 | MC-FNB | Low | Impeller | 35.88 ± 3.22 | 2.08 ± 0.11 | 7.66 ± 1.24 |
| 4 | AR-FNB | Low | Planetary | 29.18 ± 2.22 | 2.12 ± 0.24 | 5.33 ± 0.67 |
| 5 | MU-FNB | Low | Planetary | 31.88 ± 3.37 | 1.83 ± 0.18 | 6.38 ± 2.06 |
| 6 | MC-FNB | Low | Planetary | 35.49 ± 0.84 | 2.18 ± 0.11 | 7.78 ± 2.38 |
| 7 | AR-FNB | High | Impeller | 17.71 ± 0.41 | 1.52 ± 0.04 | 4.21 ± 0.43 |
| 8 | MU-FNB | High | Impeller | 18.70 ± 2.10 | 1.64 ± 0.13 | 5.43 ± 2.31 |
| 9 | MC-FNB | High | Impeller | 21.70 ± 0.52 | 1.69 ± 0.10 | 6.87 ± 1.86 |
| 10 | AR-FNB | High | Planetary | 21.81 ± 0.44 | 1.65 ± 0.11 | 6.11 ± 0.05 |
| 11 | MU-FNB | High | Planetary | 20.96 ± 1.40 | 1.64 ± 0.17 | 5.10 ± 1.38 |
| 12 | MC-FNB | High | Planetary | 22.30 ± 1.44 | 1.77 ± 0.02 | 8.25 ± 0.91 |

AR—as received;
MU—milled/uncoated;
MC—milled/coated;
H—high viscosity precursor Polymer solution:
Low viscosity level-9000 cP;
High viscosity level-15000 cP

TABLE 4

Content uniformity of the films with different dry powders:

| Run No. | Sample | Viscosity level | Mixing method | Thickness (μm) | Drug dose (mg/cm$^2$) | Wt % drug |
|---|---|---|---|---|---|---|
| 1 | AR-FNB | Low | Impeller | 148 | 3.04 | 20.69 |
| 2 | MU-FNB | Low | Impeller | 147 | 2.82 | 18.43 |
| 3 | MC-FNB | Low | Impeller | 126 | 3.27 | 21.20 |
| 4 | AR-FNB | Low | Planetary | 114 | 2.64 | 19.31 |
| 5 | MU-FNB | Low | Planetary | 109 | 2.83 | 20.30 |
| 6 | MC-FNB | Low | Planetary | 110 | 2.48 | 18.00 |
| 7 | AR-FNB | High | Impeller | 125 | 2.98 | 21.90 |
| 8 | MU-FNB | High | Impeller | 124 | 3.04 | 22.70 |
| 9 | MC-FNB | High | Impeller | 115 | 3.18 | 21.86 |
| 10 | AR-FNB | High | Planetary | 115 | 2.96 | 22.60 |

TABLE 4-continued

Content uniformity of the films with different dry powders:

| Run No. | Sample | Viscosity level | Mixing method | Thickness (μm) | Drug dose (mg/cm$^2$) | Wt % drug |
|---|---|---|---|---|---|---|
| 11 | MU-FNB | High | Planetary | 113 | 2.96 | 22.80 |
| 12 | MC-FNB | High | Planetary | 113 | 2.97 | 22.28 |

AR—as-received;
MU—milled/uncoated;
MC—milled/coated;
Polymer solution:
Low viscosity level-9000 cP;
High viscosity level-15000 cP Results and Discussion:

To test for content uniformity of the film, 10 circular samples ⅜" in diameter were punched from each film, and dissolved in 100 ml of 7.2 mg/ml SDS. The final thickness of films was measured using a digital micrometer (Mitutoyo, Japan) and the concentration of the resulting samples was measured using UV spectrophotometry (Thermo Fisher Scientific Inc., USA). The drug (FNB) loading in the dry films was kept constant at about 22 wt %. The average and relative standard deviation (RSD) for film thickness, drug mass per area for the impeller formulations are shown in Table 4 above and FIG. 8, respectively.

Figure 8:
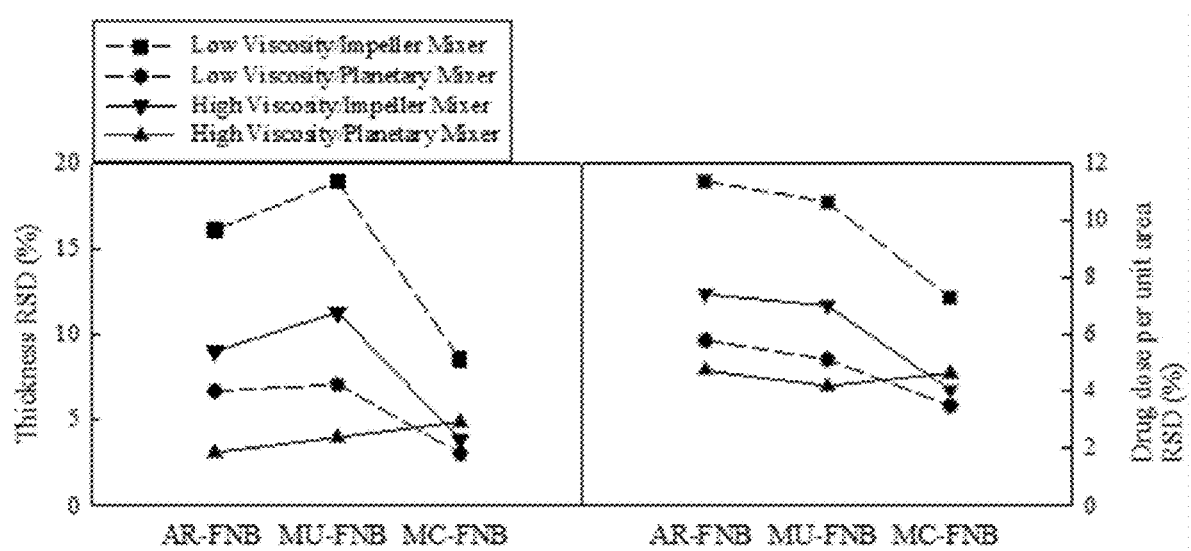
FIG. 8 shows relative standard deviation (RSD) values of film thickness and drug dose per unit area.
Figures 10A, 10B:
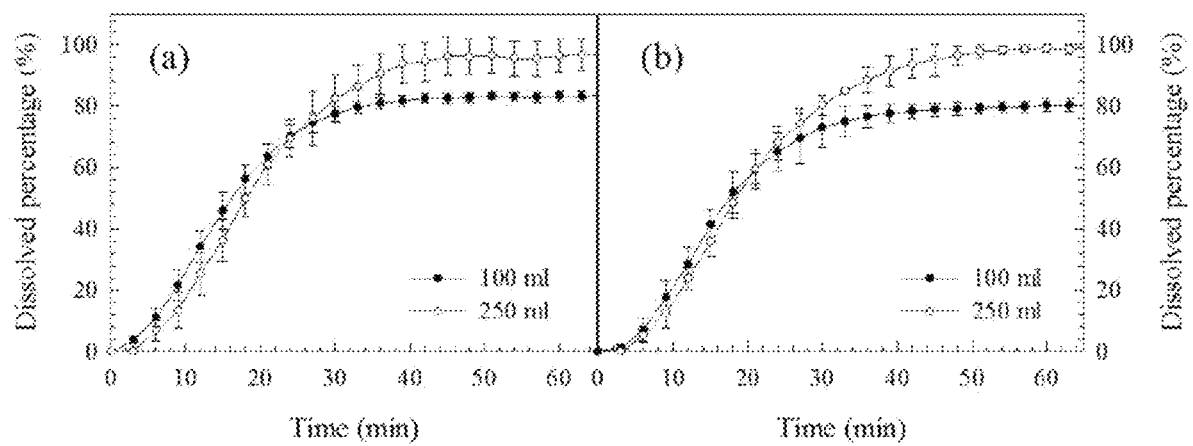
FIGS. 10A-10B show a comparison of dissolution profiles of films in 100 ml and 250 ml dissolution medium.

In Table 4 and FIG. 8, large thickness variability of films with AR-FNB or MU-FNB was attributed to the formation of drug aggregates in the films. It was observed from FIG. 8 that films with MC-FNB have improved, lower RSD % compared to films with AR-FB or MU-FNB for both low and high viscosity formulations processed by an impeller mixer. The results for films with MC-FNB in comparison with those from AR-FNB and MU-FNB offer strong evidence that even under low shear rate mixing conditions that are common in industry, surface modification of drug particles by hydrophilic silica led to excellent drug content uniformity. When an impeller mixer was used, the results suggest that high viscosity polymer solution should be used, since it led to lower RSD % values.

The optical imaging of the dry films laden with AR-FNB, MU-FNB or MC-FNB were captured using a digital optical microscope (VHX-100K, Keyence, Japan). In the test, sample films were cut to a dimension of 2 mm×3 mm, a common commercial strip film size and imaged with 50× resolution.

In FIGS. 3A-3F, the images shown are typical cases selected from many observations. Images in FIGS. 3A-3C are films produced using a low viscosity polymer solution and images in FIGS. 3D-3F are films produced using a high viscosity polymer solution. The images in FIGS. 3A and 3B show that the range of aggregate size in the film with AR-FNB and MU-FNB were from 283 to 715 μm and 395 to 1792 μm, respectively. Larger aggregates in the film with MU-FNB may be due to the high cohesion of micronized powders resulting in high aggregation. As a result, the range of aggregate sizes were much smaller than those found in films formed by low viscosity polymer solution ranging from 364 to 599 μm for AR-FNB (FIG. 3D), and 433 to 917 μm for MU-FNB (FIG. 3E).

In contrast, regardless of the precursor viscosity, smooth surface and no visible signs of drug aggregates can be observed in the images of films loaded with MC-FNB (FIG. 3C and FIG. 3F), indicating surface modification of particles by hydrophilic silica reduces agglomeration and improves dispersion of the micro particles in the films. Impeller mixing is commonly used in industry and these results indicate that it is advisable to use surface modified drug particles for improved dispersion of drug particles and achieving better film CQAs.

Dissolution experiments of films laden with AR-FNB, MU-FNB and MC-FNB were performed using a flow-through cell dissolution apparatus (USP IV, Sotax, Switzerland) with cells of an internal diameter of 22.6 mm and 0.2 μm Pall HT Tuffryn membrane disc filters. Punched circular samples from each film with an area of 0.72 cm$^2$ were horizontally positioned in the cells with 3 g of glass beads at the bottom and 2 g of glass beads on the top. 100 ml dissolution media (7.2 mg/ml SDS aqueous solution) was circulated through cells at a flow rate of 16 ml/min with a constant temperature 37 plus or minus 0.5° C. Six circular samples were used and the average drug release was plotted as a function of time.

In FIGS. 9A and 9C, the films loaded with MC-FNB exhibited faster release rates compared to films loaded with AR-FNB or MU-FNB for low and high viscous formulations. Remarkably, the MC-FNB release rates are comparable to those previously reported for FNB nanoparticles. Improved wettability due to surface modification may also have contributed to complete drug release, since films loaded with MC-FNB exhibited 100% API release while films loaded with AR-FNB or MU-FNB had incomplete release (80% to 90%), suggesting surface modification is necessary for robust performance.

Thermo-gravimetric analysis (TGA) of placebo film and films with AR-FNB, MU-FNB or MC-FNB were performed using a TGA/DSC1/SF STAR$^e$tare system (Mettler Toledo Inc., OH, USA). In a standard ceramic crucible, 5 to 8 mg of film sample was heated under a nitrogen atmosphere from 25° C. to 150° C. at a constant rate of 10° C./min, maintained at 150° C. for 15 min, heated to 250° C. at a rate of 10° C./min, and finally cooled back to 25° C. at a rate of 10° C./min.

Figure 5:
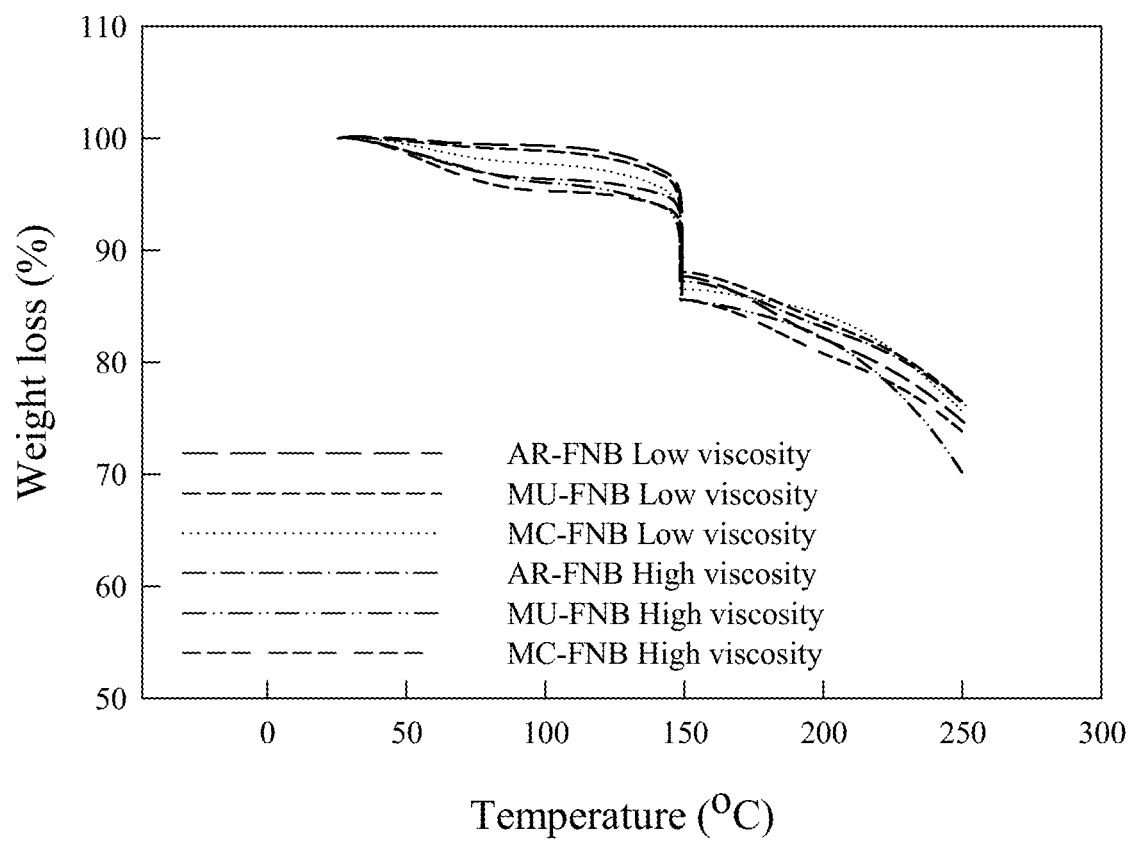
FIG. 5 shows normalized thermo-gravimetric analysis (TGA) curves for films containing AR-FNB, MU-FNB and MC-FNB of low and high viscosity formulations.
Figure 6:
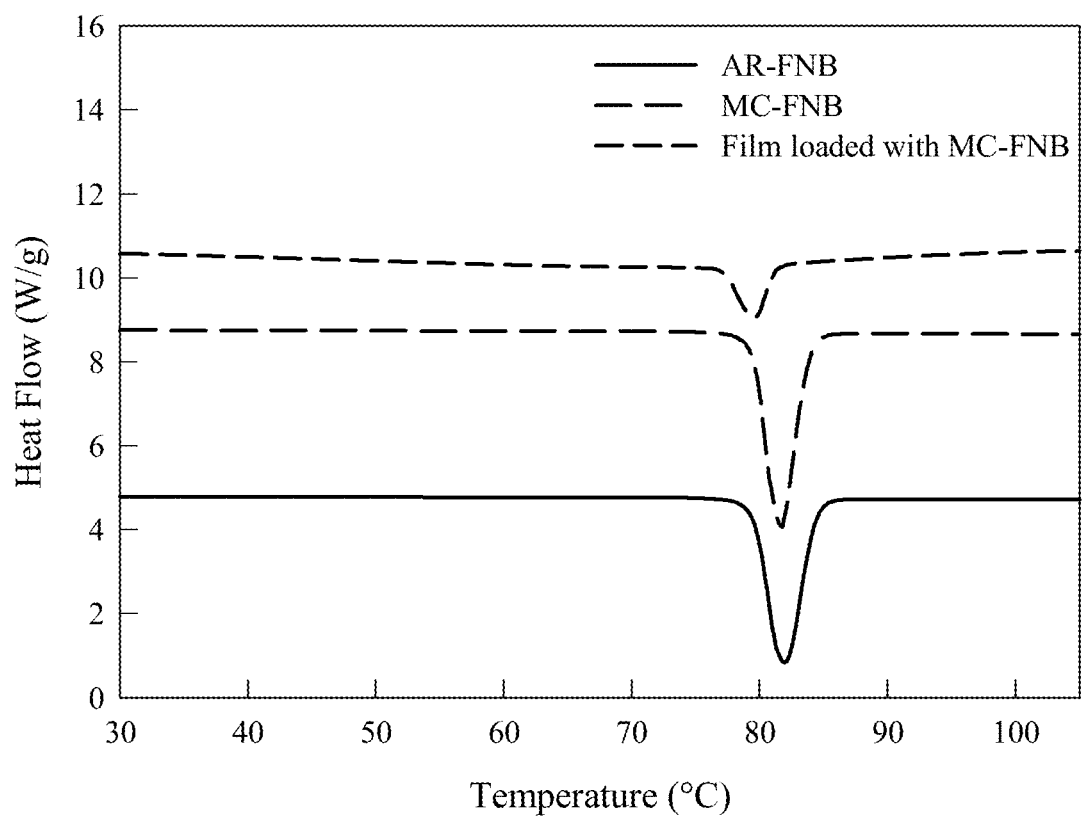
FIG. 6 shows differential scanning calorimeter (DSC) curves of AR-FNB, MC-FNB dry powder and film laden with MC-FNB.

TGA analysis was carried out and the results are shown in FIG. 5 where the curves were normalized to account for varying free or bound water content for various film samples. Films exhibited a weight loss between 0.8% and 2.6% up to 100° C. in low viscosity formulations. In contrast, the weight loss of films prepared using high viscosity formulations was higher with range 3.5 to 4.9%. This was most likely due to an increase in bounded water with larger amount of hydrophilic polymer and the difficulty of molecular movement in the high viscosity polymer solution. The additional weight loss of 10 to 15% for all films at 150° C., was mainly attributed to the loss of glycerin. Overall, the convective-conductive drying process employed was effective in keeping the moisture content under 5%, which is important because high water content can lead to tacky films. Low moisture content is also expected to result in flexible films with increased long term stability.

X-ray diffraction was performed to determine the crystallinity of AR-FNB, MU-FNB and MC-FNB particles, placebo film and drug particles in the films. Diffraction patterns were acquired for analysis of amorphous/crystalline behavior of these samples using Philips X'Pert (Almelo, Netherlands), scanning a 2θ angle in the range 5 to 35° (0.01° step).

Figure 7:
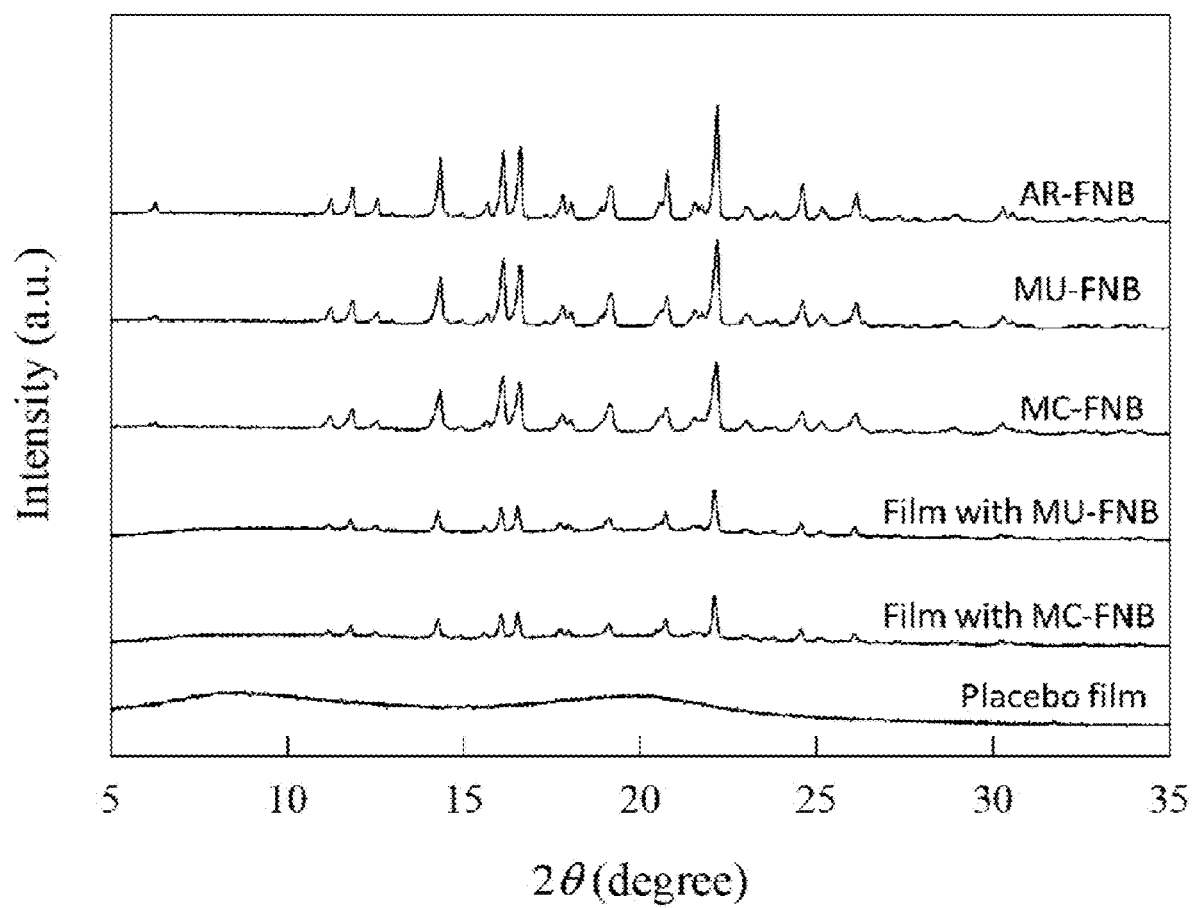
FIG. 7 shows X-ray diffraction (XRD) patterns of pure FNB and processed FNB placebo film and stripfilm containing FNB particles.

In addition, XRD analysis was performed to study the crystal structure of drug particles and the drug incorporated in the film. FIG. 7 shows the XRD patterns of AR-FNB, MU-FNB, MC-FNB, placebo film and films laden with these drug particles. AR-FNB, MU-FNB and MC-FNB presented sharp and high intensity peaks at the main diffraction angles (2θ) 15.0° to 25.0°, indicating the crystalline form of the FNB. HPMC did not show any peak due to its amorphous nature. For the films loaded with FNB particles, the peaks were attributed to FNB, confirming that HPMC had no effect on the drug crystalline structure. The spectra obtained also demonstrate that the drug in film has crystalline structure that is preserved during the milling and mixing processes.

A field emission scanning electron microscope (FESEM) (LEO1530VP GEMINI, Carl Zeiss Inc., MA, USA) was used to examine the morphology of film loaded with MC-FNB. A small piece of film laden with MC-FNB was placed on an aluminum stub via carbon tape and carbon coated using a sputter coater prior to imaging. The cross-sectional images of select films were recorded.

Figures 4A, 4B:
FIGS. 4A-4B show SEM images of the cross section of film containing MC-FNB.

In order to assess the morphology of the polymer matrix of the dry films, cross-sectional image of film loaded with MC-FNB is presented in FIGS. 4A and 4B. A well-mixed and uniform polymer matrix was observed within the film cross-section (FIG. 4A). In FIG. 4B, higher resolution imaging from cross-sectional view is shown depicting the surface morphology of what appears to be one single silica coated drug particle (see arrow). It is highly likely that silica coating on the FNB particles is retained after mixing with polymer solution, followed by casting and drying.

The mechanical properties; tensile strength (TS), Young's modulus (YM) and percentage of elongation (E %), of the films loaded with AR-FNB, MU-FNB or MC-FNB are shown in Table 3 above. The tensile strength, young's modulus, and elongation were determined from the stress-strain curve obtained from texture analyzer testing. Films containing AR-FNB or MU-FNB exhibited TS in range 17.7 to 25.6 MPa, and E % in range 4.2 to 6.2%.

Interestingly, films containing MC-FNB exhibited significantly higher TS (21.7 to 35.8 MPa) and higher E % (6.8 to 7.6), suggesting mechanical strength enhancement due to uniform distribution of micro-particles within the films. These results provide additional evidence that surface modification by hydrophilic silica promotes more uniform drug particles dispersion in the film. With regard to the effect of viscosity, the higher TS of films produced by low viscosity formulations can be mainly attributed to their higher plasticizer/polymer ratio and higher plasticizer/dry powder ratio. The YM of all films are in a very small range, between 1.47 to 2.12 GPa, the YM of low viscosity formulation was 50% higher than YM of high viscosity formulation. These mechanical tests showed that mechanical properties, TS and E %, are dependent on how uniformly the drug particles are dispersed in the films. It was found that surface modification is beneficial for the dispersion of drug particles, resulting in an increase in tensile strength and percentage of elongation.

Example 2: The Effect of Surface-Modified Dry Micronized Powders of Poorly Water Soluble Drug on Critical Quality Attributes (CQAs) of Polymer Strip Films Processed by a Planetary Mixer Two viscosities aqueous polymer solutions were used in this study. The low viscosity aqueous polymer solution contained 12% HPMC-E15LV (wt %) and 4% glycerin (wt %), and the high viscosity aqueous polymer solution contained 17% HPMC-E15LV (wt %) and 5% glycerin (wt %). The resulting polymer solutions and as-received fenofibrate particles (AR-FNB), micronized fenofibrate particles (MU-FNB), or surface-modified micronized fenofibrate particles (MC-FNB) were added in a 5:1 ratio and mixed for 5 minutes using a planetary mixer (ARE-310, THINKY, USA). The mixed low viscous FNB-polymer precursor (about 11500 to 13000 cp) and high viscous FNB-polymer precursor (about 17000 to 18500 cp) were cast at 900 to 1000 microns using a doctor blade (3700, Elcometer, USA) and dried in a drier chamber (TC-71LC, HED International, NJ, USA).

The average and relative standard deviation (RSD) for film thickness, drug mass per area for the planetary mixer formulations are shown in Table 4 above and FIG. 8, respectively. In FIG. 8, the RSD % of film thickness of high viscosity (less than 6%) is lower than low viscosity, and the RSD % of dose per unit area of both low and high viscosity formulations are all acceptable (less than 6%). This can be attributed to higher shear due to higher viscosity of the polymer solution that leads to smaller drug agglomerate size and improved mixing. Overall, better mixing and smaller drug agglomerate sizes promote lower RSD values, and those are achieved by use of high-shear mixing as in a planetary mixer, or higher viscosity polymer solution.

Figures 11A, 11C, 11D, 11F:
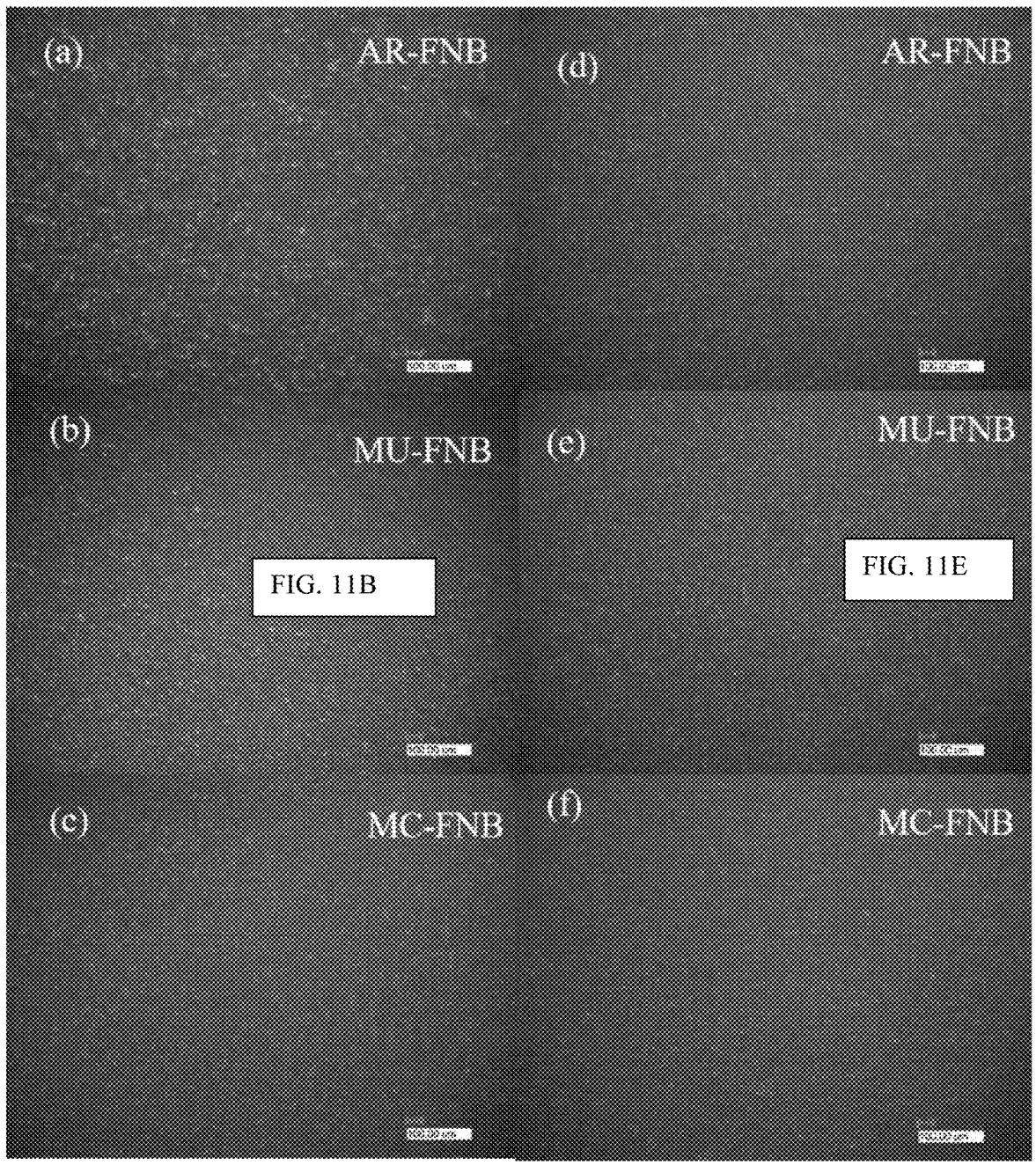
Figure 12:
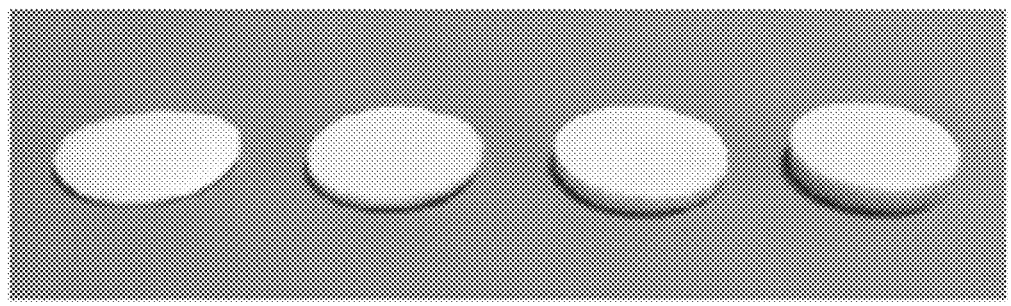
FIG. 12 shows images of films having different film thickness.

In FIGS. 11A-11F, the images shown are typical cases selected from many observations. Images in FIGS. 11A-11C are films of a low viscosity polymer solution using a planetary mixer and images in FIGS. 11D-11F are films of a high viscosity polymer solution using a planetary mixer. Regardless of drug particles used, smooth surface and no visible signs of drug aggregates can be observed in the images of films of both low and high viscosity formulations, indicating high shear mixer improves dispersion of the micro particles in the films.

In FIGS. 9B and 9D, the films loaded with MC-FNB exhibited faster release rate and complete release compared to films loaded with AR-FNB or MU-FNB for low and high viscous formulations. The viscosity of the polymer solution did affect the dissolution rate of FNB from strip film.

The mechanical properties; tensile strength (TS), Young's modulus (YM) and percentage of elongation (E %), of the films loaded with AR-FNB, MU-FNB or MC-FNB are shown in Table 3 above. Films processed by a planetary mixer exhibited similar TS and E % of films loading with AR-FNB, MU-FNB and MC-FNB particles. Higher shear mixing is beneficial for the dispersion of drug particles, resulting in an increase in tensile strength and percentage of elongation.

Example 3: Release Kinetics of Poorly Water Soluble Drug from Thick Films Prepared with Hydroxypropyl Methylcellulose: Effect of Film Thickness and Film Forming Methods Polymer solution was prepared by adding HPMC E-15 LV (polymer matrix; 17% wt) and glycerin (plasticizer; 5% wt) per formulation slowly into a beaker containing water heated to 90° C. Ample amount of time was allowed for the polymer to disperse completely without any clumps or agglomerates, and polymer solution was allowed to cool down to room temperature while being stirred continuously. The polymer solution was then mixed with silica coated griseofulvin powder. This film precursor suspension was mixed thoroughly to achieve homogeneous drug dispersion using a planetary centrifugal mixer (ARE-310, Thinky, USA) for 10 min at 2100 rpm. Finally, the defoaming of film precursor suspension was achieved by settling for overnight.

Preparation of monolithic thick film was as follows. The resulting film precursor was then cast using a cookie press injector into plastic molds with different thickness (2 to 6 mm) on the plastic substrate (Scotchpak™ 9744, 3M, MN, USA), and dried at 50° C. in a convection oven for 6 to 10 hours depending on casting film thickness.

Figure 13:
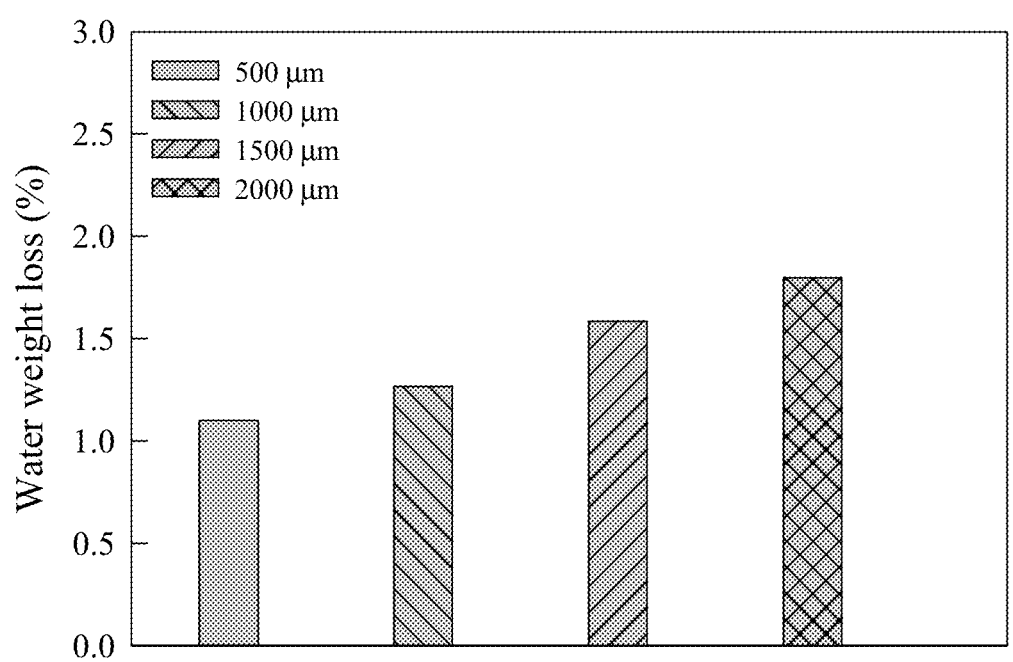
FIG. 13 shows the water weight loss (%) of films having different film thickness.

Due to the thickness larger than 200 μm, the water content of thick film might too large leading to quality issues. Generally, high water content can lead to tacky films and facilitate the growth of microorganisms. Consequently, TGA analysis was done and curves were normalized to account for varying free or bound water content between films (FIG. 13).

Films exhibited a weight loss between 1.1% and 1.8% of monolithic films up to 100° C. The additional weight loss of around 15% for all films at 150° C., was mainly attributed to the loss of glycerin. Overall, the drying process was effective in keeping the moisture content under 3%.

Figure 14:
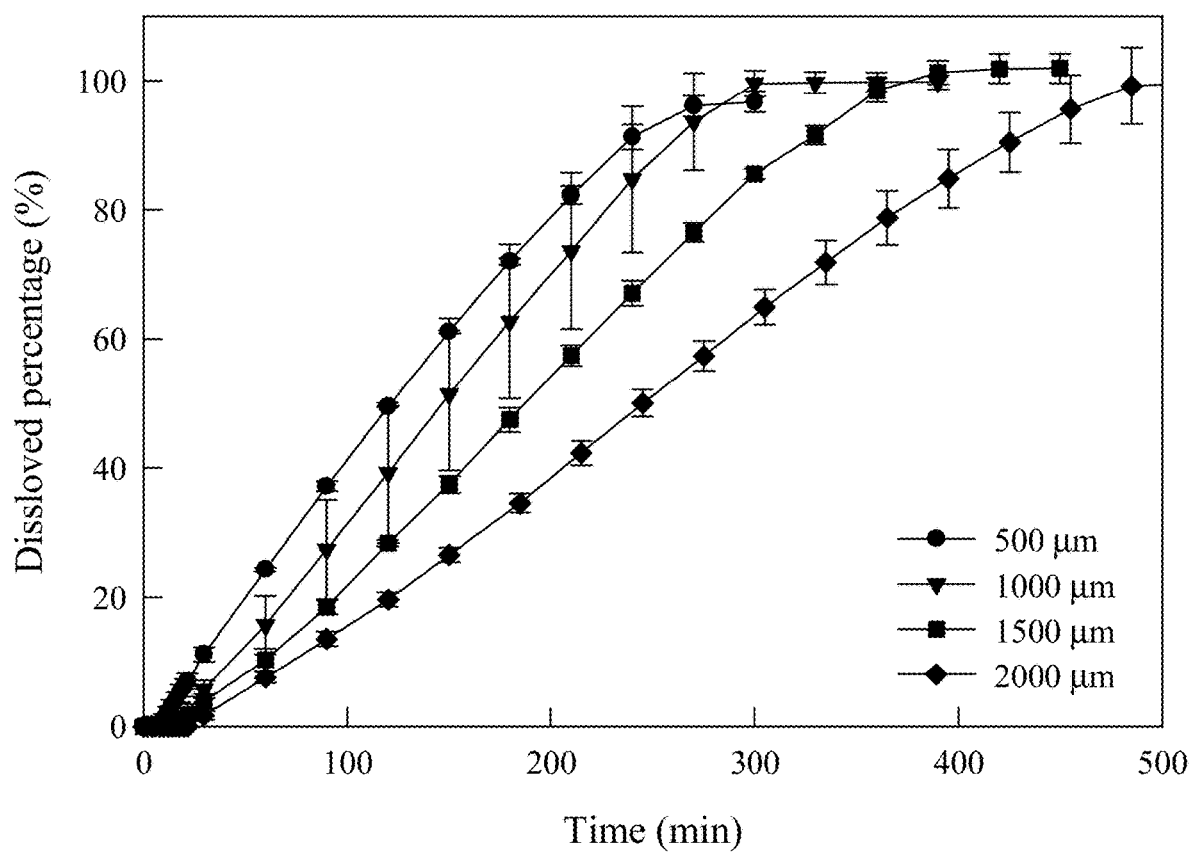
FIG. 14 shows the mean percentage cumulative release against time for different thickness of single films.

In order to examine the effect of film forming method on the drug release rate, FIG. 14 shows the mean percentage cumulative release against time for different thickness of monolithic films. The 500 μm film showed the highest release rate at the same time, followed by film matrices of 1000 μm, 1500 μm and 2000 μm. The release curves for film matrices of 1000 μm to 2000 μm were nearly linear with time after a lag time from the beginning of the release experiment.

The kinetics of drug release was analyzed by applying the Korsmeyer-Peppas equation, often used for identifying the release mechanism. The calculated exponents n of the Korsmeyer-Peppas equation indicated that the release mechanism is anomalous for a film matrix between 100 to 1000 μm, and Case II for film matrices at 1000 to 2000 μm. Thus, the film thickness increasing alters the relationship between swelling and drug diffusion of the original film.

Example 4: Release Kinetics of Poorly Water Soluble Drug from Thick Films Prepared with Hydroxypropyl Methylcellulose: Effect of Film Forming Methods Effect of method of drug addition and particle sizes on CQAs of low films at low drug load:

Polymer solution was prepared by adding HPMC E-15 LV (polymer matrix; 17% wt) and glycerin (plasticizer; 5% wt) per formulation slowly into a beaker containing water heated to 90° C. Ample amount of time was allowed for the polymer to disperse completely without any clumps or agglomerates, and polymer solution was allowed to cool down to room temperature while being stirred continuously. The polymer solution was then mixed with silica coated griseofulvin powder. This film precursor suspension was mixed thoroughly to achieve homogeneous drug dispersion using a planetary centrifugal mixer (ARE-310, Thinky, USA) for 10 min at 2100 rpm. Finally, the defoaming of film precursor suspension was achieved by settling for overnight.

Preparation of Monolithic Thick Film:

The resulting film precursor was then cast using a cookie press injector into plastic molds with different thickness (2 to 6 mm) on the plastic substrate (Scotchpak™ 9744, 3M, MN, USA), and dried at 50° C. in a convection oven for 6 to 10 hours depending on casting film thickness.

Preparation of Stacked Film:

The precursor was cast using a doctor blade on a plastic substrate (Scotchpak™ 9744, 3M, MN, USA) with a casting thickness 1.5 mm. One film was cut into 8 cm×15 cm pieces. And then 2, 3, and 4 layers of dry films were pasted with 2% HPMC solution according to 1000 μm, 1500 μm and 2000 μm dry film thickness. Prepared films were stored at ambient temperature until further analyses.

Figures 15A, 15B, 15C:
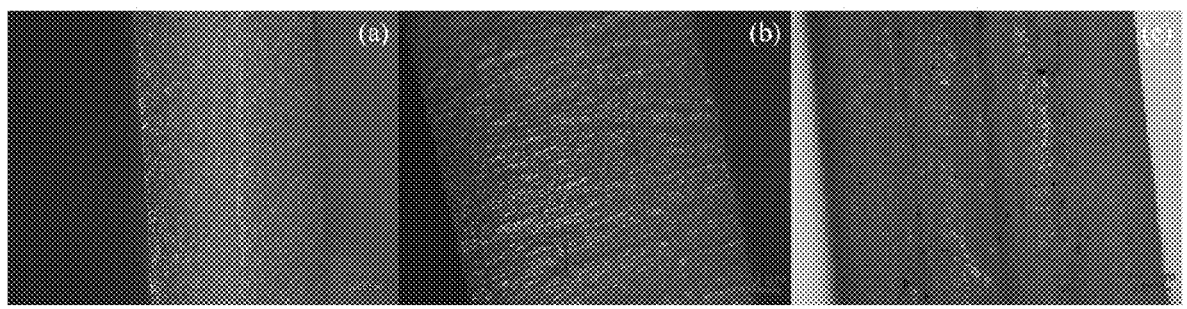
FIGS. 15A-15C show digital microscope images of the cross-section of stacked films: 2 layered (Stack-A) (FIG. 15A), 3 layered (Stack-B) (FIG. 15B), 4 layered (Stack-C) (FIG. 15C). Scale bars are 200 µm each.

FIGS. 15A-15C show the cross-sectional images of two layers of stacked film, three layers of stacked film and four layers of stacked film. A straight connective line between the layers could be detected. It shows that interfaces between the film layers were straight and layers appeared even.

Figure 16:
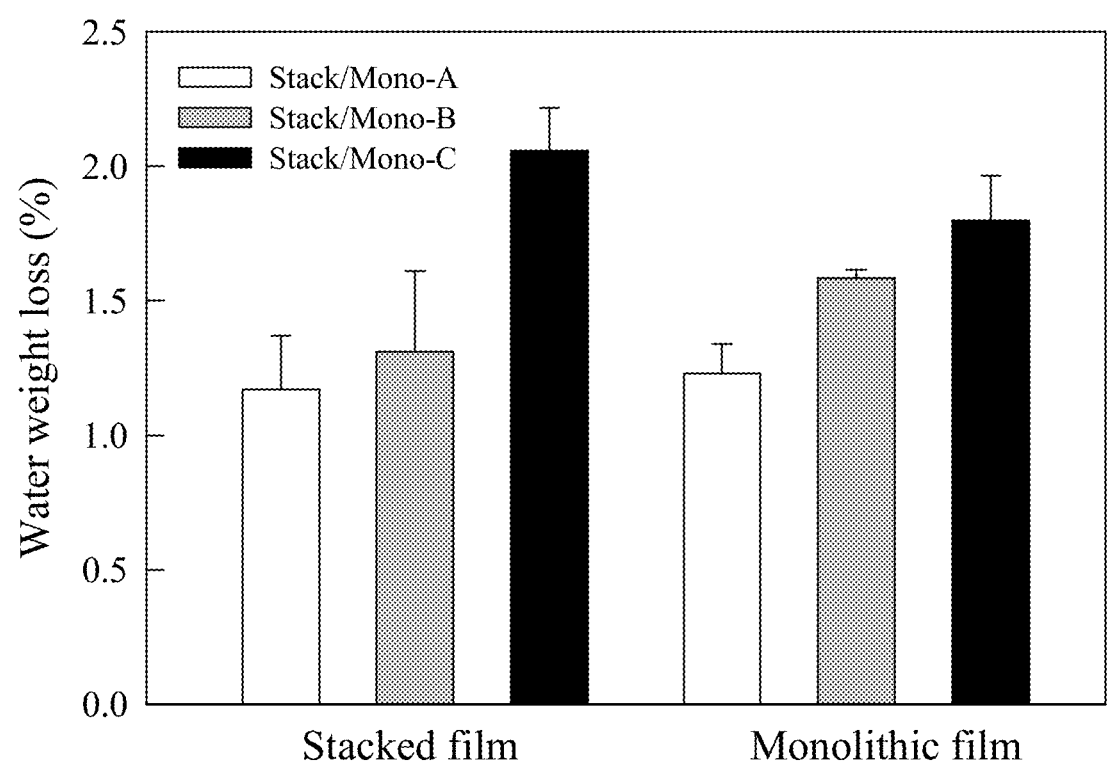
FIG. 16 shows moisture content of stacked films (Stack-A, Stack-B, Stack-C) and monolithic thick films (Mono-A, Mono-B, Mono-C) obtained through TGA analysis.

TGA analysis was done and curves were normalized to account for varying free or bound water content between films (FIG. 16). Films exhibited a weight loss between 1.1% and 1.8% of monolithic films and exhibited a weight loss between 1.1% and 2.1% of stacked films up to 100° C. The drying process was effective in keeping the moisture content under 3%.

Figures 17A, 17B, 17C, 17D:
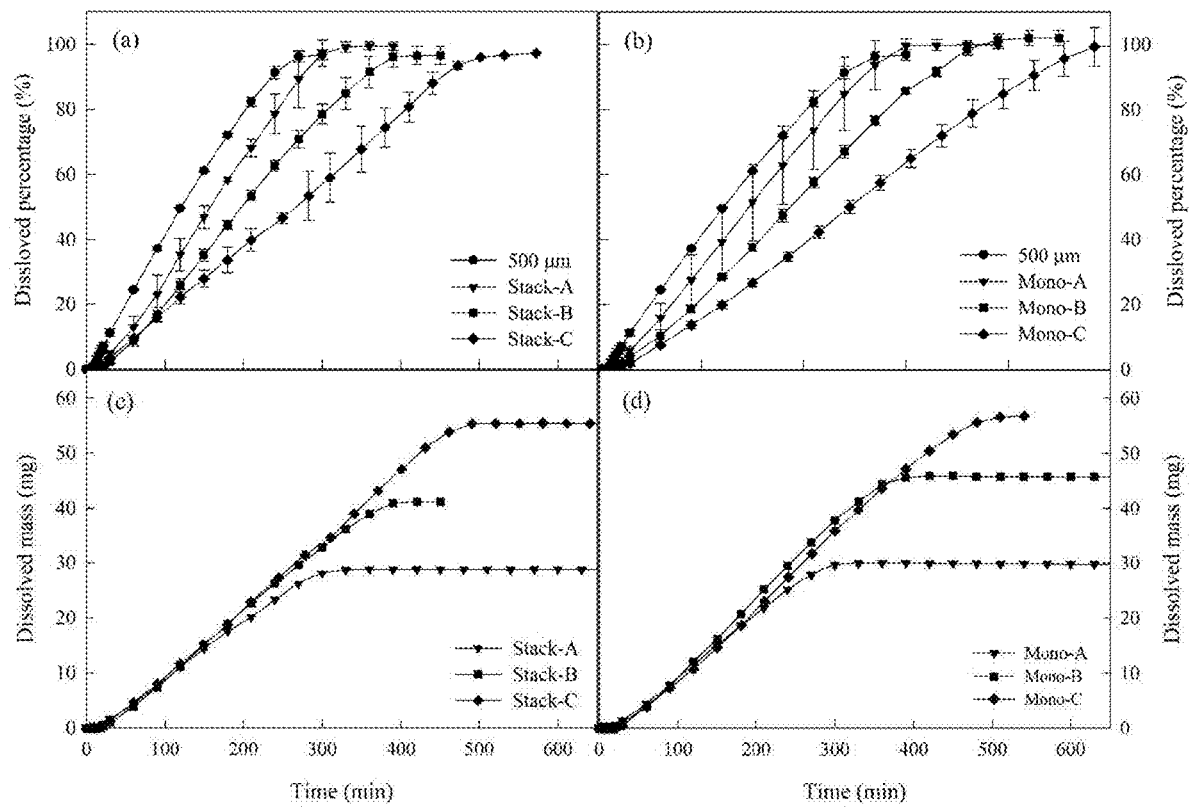
FIGS. 17A-17D show dissolution profiles of stacked films and monolithic thick films: Dissolved percentage stacked films (500 µm, Stack-A, Stack-B, Stack-C) (FIG. 17A) and monolithic thick films (500 µm, Mono-A, Mono-B, Mono-C) (FIG. 17B); Dissolved mass stacked film (Stack-A, Stack-B, Stack-C) (FIG. 17C) and monolithic thick film (Mono-A, Mono-B, Mono-C) (FIG. 17D)

In FIGS. 17A and 17B, the mean percentage cumulative release against time of 500 films, as well as Stack-A, Stack-B, Stack-C and Mono-A, Mono-B, Mono-C films are shown. The 500 μm film showed the fastest percentage release rate, followed by Stack-A, Stack-B, and Stack-C films (FIG. 17A).

The same trend was observed in the monolithic thick films (FIG. 17B). More importantly, both stacked films and monolithic thick films demonstrated the sustained release of GF drug that ranged from 240 min to 500 min which is comparable to commercially available Geomatrix® with barrier layers (Conte et al., 1993, *Multi-layered hydrophilic matrices as constant release devices (Geomatrix™ Systems)*; Journal of Controlled Release 26, 39-47) and Dome Matrix® (5% drug loading) (Casas et al., 2010, *Tapioca starch graft copolymers and Dome Matrix® modules assembling technology, I. Effect of module shape on drug release*, European Journal of Pharmaceutics and Biopharmaceutics 75, 42-47) tablets formulated with high molecular weight HPMC, having a release time of 400 to 700 min and 200 to 800 min, respectively.

In addition, appreciable lag time was observed for the films, although it is difficult to visualize in FIGS. 17A-17B, with substantially no drug released from film matrices for about 7 min to about 22 min Such trends are similar to previously reported results for tablets, and the delayed drug release might be attributed to the polymer swelling process as well as the low diffusion rate of GF particles in the eroding layer of the HPMC matrix (Ford et al., 1987, *Importance of drug type, tablet shape and added diluents on drug release kinetics from hydroxypropylmethylcellulose matrix tablets*, Int. Journal of Pharmaceutics 40, 223-234).

Since the relative amounts of drug released can be important (Siepmann et al., 2000; *Calculation of the required size and shape of hydroxypropyl methylcellulose matrices to achieve desired drug release profiles*; Int. Journal of Pharmaceutics 201, 151-164), those trends are shown in FIGS. 17C and 17D.

The $t_{50}\%$, $t_{75}\%$, and $t_{90}\%$ dissolution times from the monolithic and stacked films were compared based on the similarity and difference factors (Table 5). For the dissolution profiles to be considered similar, $f_1$ values should be close to zero, and $f_2$ values should be close to 100 (FDA 1997, *Guidance for industry-dissolution testing of immediate release solid oral dosage forms*; FDA Maryland). Generally, $f_1$ values up to 15 and $f_2$ values greater than 50 should ensure equivalence of the dissolution curves, indicating an average difference of no more than 10% at a given sample time point. As the dissolution time evolved, $f_1$ tended to be closer to zero and $f_2$ stayed close enough to 100; only deviating slightly. Therefore, it can be concluded that monolithic thick films and stacked films have similar release rates.

To better understand the drug release behavior depicted in FIG. 17, the modified Korsmeyer-Peppas power law model (Eq. 1) was applied and the diffusional exponent n (Eq. 1), representing the mechanism of drug release, was computed, along with an additional result for 100 μm film as an example of typical thin film from literature (Krull et al., 2015, *Polymer strip films as a robust, surfactant-free platform for delivery of BCS Class II drug nanoparticles*; Int. Journal of Pharmaceutics 489, 45-57).

Figure 18:
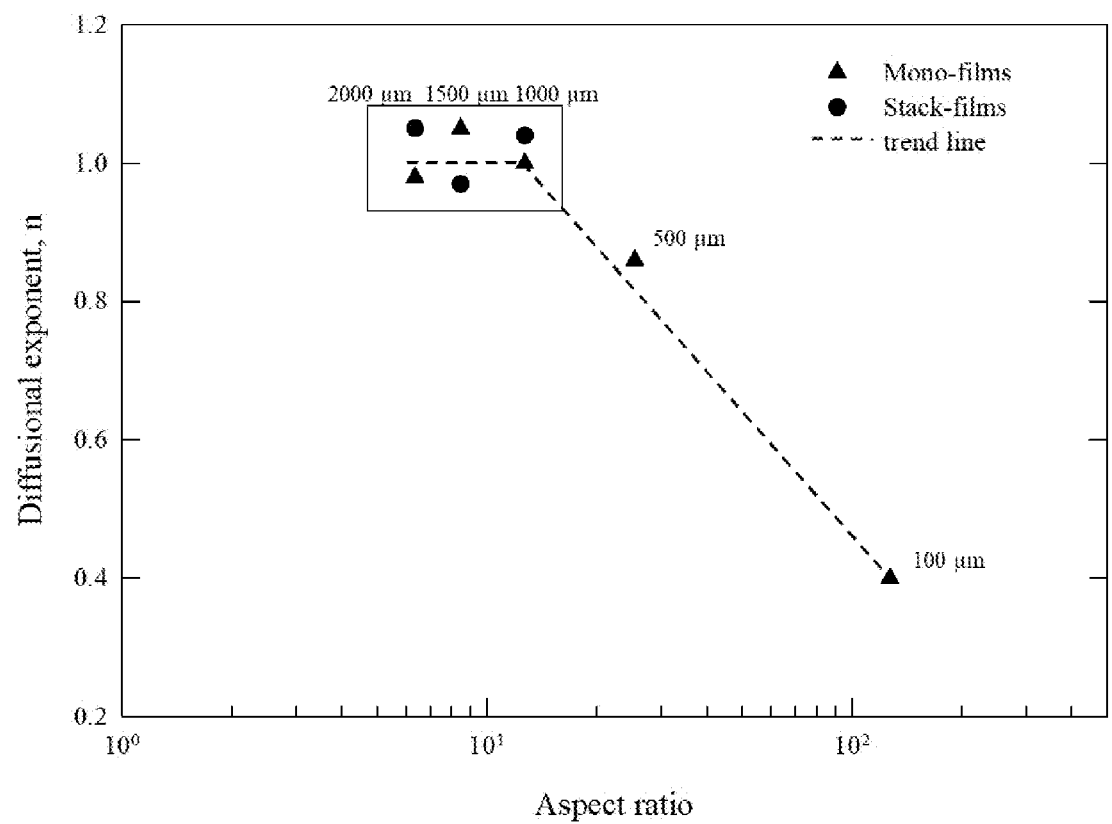
FIG. 18 shows diffusional exponent, n, of Eq. (1) for drug release from monolithic thick films (Mono) and stacked films (Stack), as a function of their aspect ratio; The dashed lines represent general trends.

FIG. 18 shows that the diffusional exponent n is about 1 (n=0.97-1.05) for the films 1000 μm and thicker, indicating true zero-order release. As a reference, values of the exponent lower than 0.5 indicate that the drug release mechanism is Fickian diffusion; whereas for n between 0.5 to 1.0, it is termed anomalous transport and when n is equal to 1.0 it is case-II transport (Ritger and Peppas, 1987, *A simple equation for description of solute release I. Fickian and nonfickian release from non-swellable devices in the form of slabs, spheres, cylinders or discs*; Journal of Controlled Release 5, 23-36; *A simple equation for description of solute release II. Fickian and anomalous release from swellable devices*; Journal of Controlled Release 5, 37-42).

To summarize, the release mechanism for thin films, e.g., 100 μm film matrix (n=0.4), is predominantly one-dimensional and follows Fickian diffusion (Ford et al., 1987, *Importance of drug type, tablet shape and added diluents on drug release kinetics from hydroxypropylmethylcellulose matrix tablets*; Int. Journal of Pharmaceutics 40, 223-234).

However, as the film thickness increases making the release three-dimensional, the mechanism is that of anomalous for intermediate thickness, e.g., 500 μm film matrix (n=0.86), and true zero-order release for thicker films, e.g., 1000 μm and higher. As was expected, both the monolithic and stacked films matrixes exhibit similar release mechanisms, which was the swelling of HPMC matrix coupled with an important diffusive contribution for thinner films (Ritger and Peppas, 1987, *A simple equation for description of solute release II. Fickian and anomalous release from swellable devices*; Journal of Controlled Release 5, 37-42). It is noted that similar, but slightly lower values for n (0.9 and 0.82) were obtained for poorly water-soluble drugs, indomethacin and diazepam, released from tablets having a near zero-order release (Ford et al., 1987, *Importance of drug type, tablet shape and added diluents on drug release kinetics from hydroxypropylmethylcellulose matrix tablets*; Int. Journal of Pharmaceutics 40, 223-234). The present results for slurry cast films of poorly water-soluble drug GF exhibit n to be essentially 1, which suggests that the performance compares favorably with HPMC based tablets.

Since the aspect ratio, e.g., disk diameter divided by disk thickness for this disk type dosage shape ranges from about 6 to 25 for thickness of 500 to 2000 μm, the release, being predominantly three-dimensional, is expected to be linearly related with the surface area of the dosage (Ford et al., 1987, *Importance of drug type, tablet shape and added diluents on drug release kinetics from hydroxypropylmethylcellulose matrix tablets*; Int. Journal of Pharmaceutics 40, 223-234).

However, because the film samples have the same diameter, the thickness becomes the controlling factor, leading to the drug release mainly influenced by the thickness. In order to examine how the kinetic constant, k, from Eq. (1) varies as a function of the characteristic indicator of the structure and geometry of the dosage shape, the results are plotted in FIGS. 19A and 19B for both thickness and dosage surface area, confirming the behavior to be linearly dependent on the surface area as predicted previously (Ford et al., 1987, *Importance of drug type, tablet shape and added diluents on drug release kinetics from hydroxypropylmethylcellulose matrix tablets*; Int. Journal of Pharmaceutics 40, 223-234), but may be easily represented by thickness.

The dissolution behavior presented above suggests that the multi-layer thick film system may provide an approach for preparing film-based dosage forms by assuring that the film-thickness is above a certain threshold for a given sample diameter. It is noted that apart from being a strong function of thickness, the release kinetics, and total time of release may depend on the properties of the polymer forming the matrix, including its molecular weight, further adding to the dosage design flexibility. This may be an interesting topic for further future research.

TABLE 5

Similarity and difference factors for dissolution profiles of films:

|  | Sample | Fit Factor | |
| --- | --- | --- | --- |
|  |  | $f_1$ | $f_2$ |
| $t_{50\%}$ | Mono-A/Stack-A | 9.8 | 87.2 |
|  | Mono-B/Stack-B | 3.6 | 94.9 |
|  | Mono-C/Stack-C | 5.8 | 94.1 |
| $t_{75\%}$ | Mono-A/Stack-A | 7.8 | 83.3 |
|  | Mono-B/Stack-B | 5.0 | 85.4 |
|  | Mono-C/Stack-C | 5.5 | 88.1 |
| $t_{90\%}$ | Mono-A/Stack-A | 6.7 | 80.2 |
|  | Mono-B/Stack-B | 6.2 | 75.5 |
|  | Mono-C/Stack-C | 4.6 | 84.7 |

Example 5: Effect of Low Drug Loadings on CQAs of Films with Dry Powder

Effect of Method of Drug Addition on CQAs of Low Films at Low Drug Load

Polymer solution was prepared by adding HPMC E-15 LV (polymer matrix; 12% wt) and glycerin (plasticizer; 5% wt) per formulation slowly into a beaker containing water heated to 90° C. Ample amount of time was allowed for the polymer to disperse completely without any clumps or agglomerates, and polymer solution was allowed to cool down to room temperature while being stirred continuously. The polymer solution was then mixed with as-received dry particle (AR-DP), micronized uncoated dry particles (MU-DP) or micronized silica coated dry particles (MC-DP). The final drug loadings of dry film are designed at 1%, 3% and 5%. The film precursor suspensions were mixed thoroughly to achieve homogeneous drug dispersion using an impeller mixer (RW16, IKA, USA) for 3 hours at 120 rpm. Finally, the defoaming of the film precursor suspension was achieved by settling for overnight. The resulting film precursor was then cast using a doctor blade on the plastic substrate (Scotchpak™ 9744, 3M, MN, USA), and dried at 50° C. in a convection oven for 1 to 2 hours depending on casting film thickness.

The average and relative standard deviation (RSD %) for film thickness, drug mass per area and drug loading (%) for all formulations are shown in Table 6a and Table 6b below.

In Table 6a, the thickness of the films ranges between 98 to 111 μm, and drug amount per unit area and drug loading for the majority of 3 wt % and 5 wt % films are 3 times and 5 times higher as compared to 1 wt % films, respectively.

In Table 6b, the RSD values of 1 wt %, 3 wt %, and 5 wt % films regarding to thickness, drug amount per unit area, and drug loading of MC-DP films are below 6%.

Not surprisingly, the films with AR-DP had the higher RSD % for thickness and drug per unit area.

TABLE 6a

Average values of the films with different dry powders:

| Sample | Thickness (μm) | | | Drug per unit area (mg/cm²) | | | Drug loading (wt %) | | |
| --- | --- | --- | --- | --- | --- | --- | --- | --- | --- |
| | 1 wt % | 3 wt % | 5 wt % | 1 wt % | 3 wt % | 5 wt % | 1 wt % | 3 wt % | 5 wt % |
| AR-DP | 107.6 | 111.5 | 101.1 | 0.14 | 0.41 | 0.73 | 1.0 | 2.8 | 5.4 |
| MU-DP | 109.9 | 107.2 | 102.2 | 0.13 | 0.40 | 0.60 | 0.9 | 2.8 | 4.9 |
| MC-DP | 105.9 | 98.8 | 109.9 | 0.12 | 0.36 | 0.62 | 0.9 | 2.9 | 5.2 |

TABLE 6b

RSD values of the films with different dry powders

| Sample name | Thickness RSD (%) | | | Drug per unit area RSD (%) | | | Drug loading RSD (%) | | |
| --- | --- | --- | --- | --- | --- | --- | --- | --- | --- |
| | 1 wt % | 3 wt % | 5 wt % | 1 wt % | 3 wt % | 5 wt % | 1 wt % | 3 wt % | 5 wt % |
| AR-DP | 4.7 | 3.2 | 11.2 | 9.3 | 2.3 | 11.2 | 5.8 | 1.4 | 1.6 |
| MU-DP | 6.9 | 3.5 | 2.4 | 6.6 | 3.7 | 2.6 | 2.8 | 3.1 | 1.1 |
| MC-DP | 4.3 | 4.7 | 1.3 | 4.4 | 3.5 | 0.8 | 3.3 | 4.2 | 1.1 |

Table 7 below shows the original particle size of dry powders and the size of particles redispersed from film.

The particle sizes of AR-DP and MC-DP are similar to the size of particles redispersed from film, indicating those particles can be stabilized in the film processes. But the particle size of redispersion of films with MU-DP is larger than the original particle size of MU-DP, 7.15 μm compared to 4.86 μm. Micronized dry powder tends to aggregate in the film processes.

TABLE 7

Particle size distribution of drug powder and redispersion from films:

| | | D50 | |
| --- | --- | --- | --- |
| Drug loading (%) | | Original PS (μm) | Redispersion (μm) |
| 1% | AR-DP | 9.430 | 9.971 |
| 1% | MU-DP | 4.860 | 7.154 |
| 1% | MC-DP | 4.200 | 4.457 |
| 3% | AR-DP | 9.430 | 9.644 |
| 3% | MU-DP | 4.860 | 6.698 |
| 3% | MC-DP | 4.200 | 4.640 |
| 5% | AR-DP | 9.430 | 9.441 |
| 5% | MU-DP | 4.860 | 6.127 |
| 5% | MC-DP | 4.200 | 4.412 |

FIGS. 20A-20F show the optical microscope images of films with AR-DP, MU-DP, MC-DP at 1% and 5% drug loadings. Particle aggregates can be observed in films with AR-DP and MU-DP clearly. However, the film with MC-DP shows uniform distribution of particles in the film. TGA analysis was done and curves were normalized to account for varying free or bound water content between films (FIGS. 21A-21C). The 1% films exhibited higher water loss than 3% and 5% films up to 100° C., with 4.6% to 7.4% for 1% films, 3.5% to 4.4% for 3% films, and 3.2% to 3.8% for 5% films. The drying process was effective for films loaded with dry powder in keeping the moisture content under 7%. FIGS. 22A-22C show the dissolution profiles of exemplary films. Obviously, dissolution rate of films with MC-DP, was faster than films with AR-DP and MU-DP. The dissolution rate of films with AR-DP was similar to films with MU-DP of 1% and 5% films.

The mechanical properties; tensile strength (TS), Young's modulus (YM) and percentage of elongation (E %), of the films loaded with AR-FNB, MU-FNB or MC-FNB are shown in Table 8 below. The tensile strength, young's modulus, and elongation were determined from the stress-strain curve obtained from texture analyzer testing.

First, there is substantially no significant difference (p greater than 0.05) of films of different drug loadings (1 wt %, 3 wt %, and 5 wt %) in terms of E %, and YM, and a minor decrease in TS of films with increased drug loading. Next, films containing AR-DP and MU-DP displayed TS and E % in range of 15.4 to 21.4 MPa and 54.0 to 69.5%. Films containing MC-FNB illustrated significantly higher TS (25.1 to 28.5 MPa) and E % (82.7 to 91.0%), suggesting mechanical strength enhancement perhaps due to the uniform distribution of micronized coated particles within films. Although the YM values of the films are in a very small range between 0.22 to 0.40 GPa, MC-DP films were around 40% higher than films loaded with AR-DP and MU-DP.

TABLE 8

Mechanical properties of films with drug powders:

| Sample | Tensile strength (MPa) | | | Elongation percentage (%) | | |
| --- | --- | --- | --- | --- | --- | --- |
| | 1 wt % | 3 wt % | 5 wt % | 1 wt % | 3 wt % | 5 wt % |
| AR-DP | 20.6 ± 0.8 | 18.7 ± 0.9 | 17.4 ± 0.1 | 68.6 ± 5.4 | 69.5 ± 3.4 | 57.0 ± 3.6 |
| MU-DP | 21.4 ± 1.0 | 17.8 ± 1.0 | 15.4 ± 0.6 | 54.4 ± 5.8 | 54.0 ± 5.0 | 68.0 ± 3.6 |
| MC-DP | 28.5 ± 1.4 | 25.9 ± 4.0 | 25.1 ± 1.4 | 82.7 ± 6.3 | 83.0 ± 8.5 | 91.0 ± 9.5 |

TABLE 8-continued

Mechanical properties of films with drug powders:

| | Young's modulus (GPa) | | |
|---|---|---|---|
| Sample | 1 wt % | 3 wt % | 5 wt % |
| AR-DP | 0.29 ± 0.01 | 0.27 ± 0.01 | 0.28 ± 0.04 |
| MU-DP | 0.33 ± 0.04 | 0.26 ± 0.01 | 0.22 ± 0.06 |
| MC-DP | 0.40 ± 0.02 | 0.38 ± 0.06 | 0.30 ± 0.03 |

Example 6: Effect of Low Drug Loadings on Critical Quality Attributes (CQAs) of Films Made with Suspensions of Dry Surface Modified Drug Powders Effect of Low Drug Loadings on CQAs of Film:

Polymer solution was prepared by adding HPMC E-15 LV (polymer matrix; 12% wt) and glycerin (plasticizer; 5% wt) per formulation slowly into a beaker containing water heated to 90° C. Ample amount of time was allowed for the polymer to disperse completely without any clumps or agglomerates, and polymer solution was allowed to cool down to room temperature while being stirred continuously. The polymer solution was then mixed with as-received suspension (AR-S), microparticle suspension (M-S), nanoparticles suspension (N-S). The final drug loadings of dry film were designed at 1%, 3% and 5%. The film precursor suspensions were mixed thoroughly to achieve homogeneous drug dispersion using an impeller mixer (RW16, IKA, USA) for 3 hours at 120 rpm. Finally, the defoaming of film precursor suspension was achieved by settling for overnight.

The average and relative standard deviation (RSD %) for film thickness, drug mass per area and drug loading (%) for all formulations are shown in Table 9a and Table 9b below.

In Table 9a, the thickness of the films ranges between 98 to 111 μm, and drug amount per unit area and drug loading for the majority of 3 wt % and 5 wt % films are 3 times and 5 times higher compared to 1 wt % films, respectively.

In Table 9b, most RSD values of AR-S and N-S films regarding to thickness, drug amount per unit area, and drug loading of MC-DP films are below 6%. Not surprisingly, the films with AR-DP had the higher RSD % for thickness and drug per unit area.

Higher RSD % found in M-S films may be due to the drug particle settlement in the drug suspensions after storage.

TABLE 9a

Average value of content uniformity of films with drug suspensions:

| | Thickness (μm) | | | Drug per unit area (mg/cm$^2$) | | | Drug loading (wt %) | | |
|---|---|---|---|---|---|---|---|---|---|
| Sample | 1 wt % | 3 wt % | 5 wt % | 1 wt % | 3 wt % | 5 wt % | 1 wt % | 3 wt % | 5 wt % |
| AR-S | 108.6 | 108.6 | 107.3 | 0.10 | 0.45 | 0.69 | 0.7 | 3.4 | 5.2 |
| M-S | 111.3 | 100.8 | 104.6 | 0.13 | 0.42 | 0.70 | 0.8 | 3.4 | 5.5 |
| N-S | 108.8 | 98.5 | 101.3 | 0.15 | 0.37 | 0.67 | 1.1 | 3.0 | 5.2 |

TABLE 9b

RSD value of content uniformity of films with drug suspensions:

| Sample | Thickness RSD (%) | | | Drug per unit area RSD (%) | | | Drug loading RSD (%) | | |
|---|---|---|---|---|---|---|---|---|---|
| name | 1 wt % | 3 wt % | 5 wt % | 1 wt % | 3 wt % | 5 wt % | 1 wt % | 3 wt % | 5 wt % |
| AR-S | 4.2 | 5.4 | 1.6 | 2.3 | 2.3 | 4.1 | 2.2 | 1.2 | 2.8 |
| M-S | 4.6 | 6.1 | 2.9 | 3.6 | 4.5 | 9.2 | 1.6 | 1.6 | 1.6 |
| N-S | 2.9 | 1.2 | 3.4 | 6.5 | 1.3 | 3.7 | 3.3 | 1.9 | 1.7 |

Table 10 below shows the original particle size of suspensions and the size of particle redispersed from film.

The particle sizes of AR-S, M-S and N-S are similar to the size of particles redispersed from film, indicating those particles can be stabilized in the film processes.

TABLE 10

Particle size distribution of drug suspensions and redispersion from films:

| | | D50 | |
|---|---|---|---|
| Drug loading (%) | | Original PS (μm) | Redispersion (μm) |
| 1% | AR-S | 25.41 | 10.600 |
| 1% | M-S | 1.569 | 1.937 |
| 1% | N-S | 0.270 | 0.225 |
| 3% | AR-S | 25.41 | 9.151 |
| 3% | M-S | 1.569 | 2.000 |
| 3% | N-S | 0.270 | 0.298 |
| 5% | AR-S | 25.41 | 10.908 |
| 5% | M-S | 1.569 | 2.407 |
| 5% | N-S | 0.270 | 0.192 |

Figure 23A:
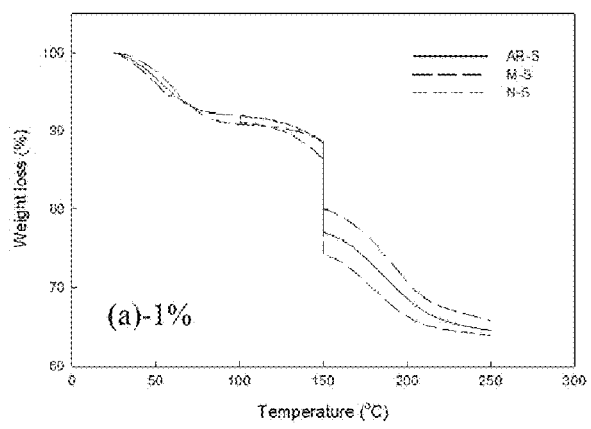
FIGS. 23A-23C show the water weight loss (%) between different films.
Figure 23B:
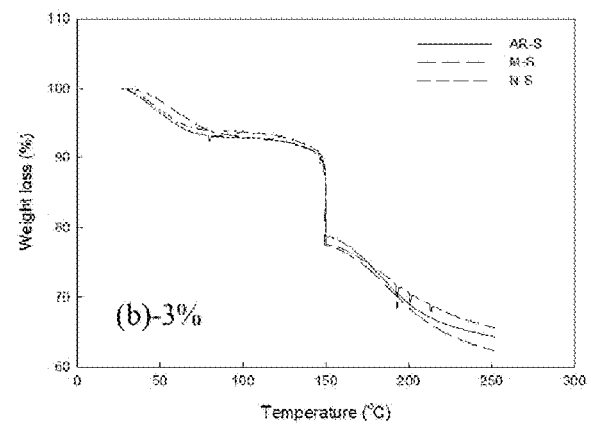
Figure 23C:
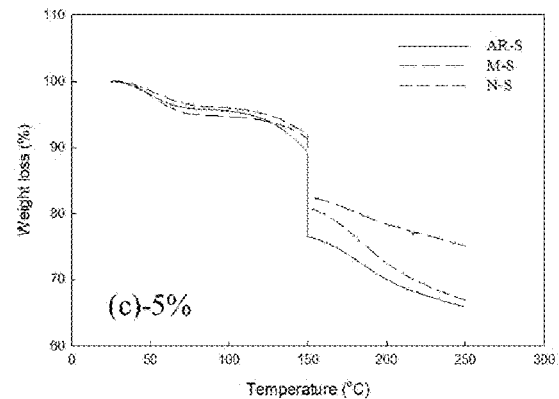

TGA analysis was done and curves were normalized to account for varying free or bound water content between films (FIGS. 23A-23C). The 1% films exhibited higher water loss than 3% and 5% films up to 100° C., 8.7 to 9.7% for 1% films, 6.5 to 7.5% for 3% films, and 4.7 to 5.8% for 5% films. The additional weight loss of around 15% for all films at 150° C., was mainly attributed to the loss of glycerin. Overall, the drying process was effective for films loaded with dry powder in keeping the moisture content under 10%.

FIGS. 24A-24C show the dissolution profiles of exemplary films. As shown, the dissolution rate of films with N-S and M-S are faster than films with AR-S. The dissolution rate of films with N-S is similar to films with M-S of 1% and 5% films.

The mechanical properties; tensile strength (TS), Young's modulus (YM) and percentage of elongation (E %), of the films loaded with AR-S, M-S and N-S are shown in Table 11 below. The tensile strength, young's modulus, and elongation were determined from the stress-strain curve obtained from texture analyzer testing.

First, there is substantially no significant difference (p greater than 0.05) of films of different drug loadings (1 wt %, 3 wt %, and 5 wt %) in terms of E %, and YM, and a minor decrease in TS of films with increased drug loading. Next, films containing AR-S and M-S displayed TS and E % in range of 22.3 to 25.8 MPa and 67 to 86%.

Films containing N-S illustrated significantly higher TS (28.6 to 30.2 MPa) and E % (84.6 to 87.4%), suggesting mechanical strength enhancement perhaps due to the uniform distribution of nano-particles within films. Although the YM values of all films are in a very small range between 0.22 to 0.40 GPa, N-S films were around 30% higher than films loaded with AR-S and M-S.

TABLE 11

Mechanical properties of films with drug suspensions:

| Sample | Tensile strength (MPa) | | | Elongation percentage (%) | | |
|---|---|---|---|---|---|---|
| | 1 wt % | 3 wt % | 5 wt % | 1 wt % | 3 wt % | 5 wt % |
| AR-S | 25.8 ± 1.3 | 24.6 ± 1.9 | 23.4 ± 2.2 | 74.9 ± 14.0 | 72.0 ± 10.0 | 78.1 ± 7.0 |
| M-S | 24.5 ± 1.9 | 23.1 ± 2.8 | 22.3 ± 1.6 | 77.0 ± 5.3 | 67.2 ± 10.2 | 86.0 ± 6.0 |
| N-S | 30.2 ± 0.6 | 28.9 ± 2.8 | 28.6 ± 2.3 | 87.4 ± 2.5 | 84.9 ± 3.5 | 84.6 ± 7.1 |

| Sample | Young's modulus (GPa) | | |
|---|---|---|---|
| | 1 wt % | 3 wt % | 5 wt % |
| AR-S | 0.30 ± 0.02 | 0.34 ± 0.03 | 0.31 ± 0.03 |
| M-S | 0.32 ± 0.01 | 0.33 ± 0.04 | 0.32 ± 0.02 |
| N-S | 0.40 ± 0.03 | 0.37 ± 0.04 | 0.30 ± 0.02 |

Example 7: Effect of Surface Modification of Micronized Drug Particles on Mixing Properties of Film Manufacturing The drug powder wettability in the deionized water was measured by the Washburn method. Attension Sigma 700 set-up (Biolin Scientific, MD, USA) was used to study the penetration of deionized water into a packed powder bed of drug particles (AR-FNB, MU-FNB and MC-FNB) inside a cylindrical column and determine the drug powder wettability, based on the Washburn method. About 0.40 grams of drug powder was packed uniformly into the tube before each measurement. A filter paper was placed at the perforated end of the cylindrical column in order to support drug powders, followed by packing about 0.40 g of drug powders uniformly in the column.

Figure 25:
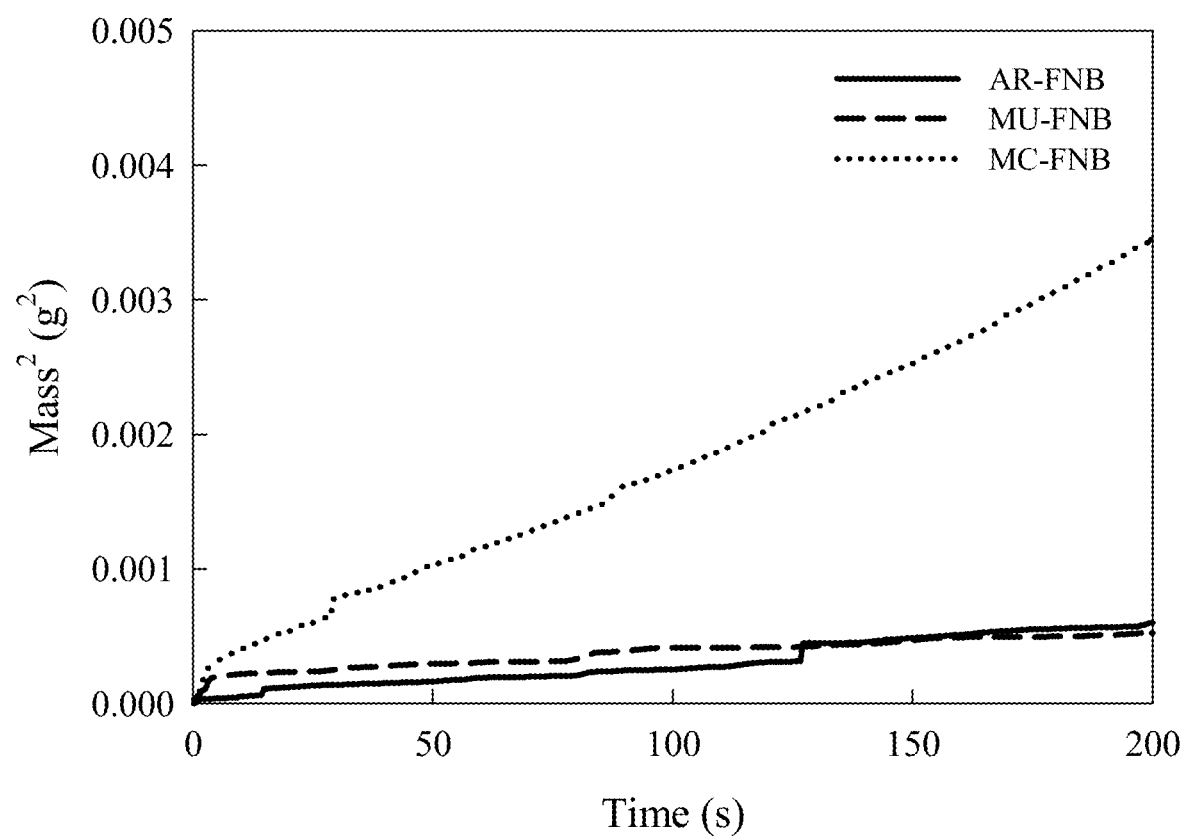
FIG. 25 shows the wetting curves of AR-FNB, MU-FNB and MC-FNB powders in deionized water.

A petri dish containing deionized water was placed below the perforated end of the column on the mechanical platform. Attension Sigma 700 recorded the mass of liquid penetrated into the drug powder bed as a function of time. The wetting curves of drug powders are reported in FIG. 25. MC-FNB powder was observed with higher rate of mass/time compared to AR-FNB and MU-FNB powders. This suggests that MC-FNB has better wettability than the other two.

Figures 26A, 26B, 26C:
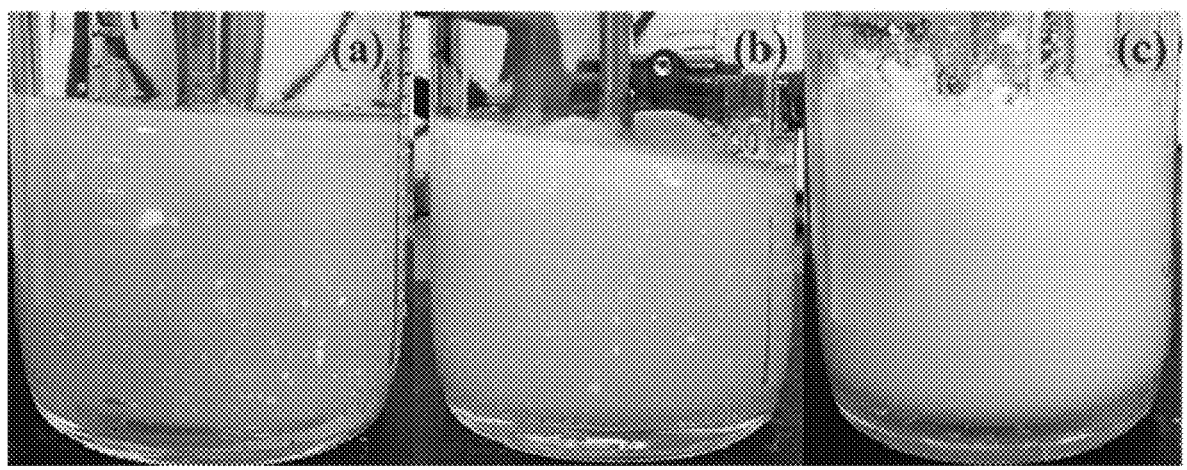
FIGS. 26A-C show pictures during mixing of polymer solutions with drug powders.

The polymer solutions were mixed with AR-FNB, MU-FNB and MC-FNB micronized particles to form the film precursor. FIGS. 26A-C show the mixing process of film precursors. It can be observed that film precursors with AR-FNB (FIG. 26A) and MU-FNB (FIG. 26B) contained plenty of drug chunks, while the film precursor with MC-FNB (FIG. 26C) looked like milk, smooth without any obvious drug chunks.

Example 8: Comparison Between Slurry Casting and Solution Casting Techniques of Film Loaded with Poorly Water Soluble Drug Fenofibrate Solution casting films were prepared by dissolving HPMC-E15 LV in the water and acetone binary solution (1:4 w/w) at 50° C. and then mixing with FNB drug particles in the THINKY mixer for 3 min. The resulting film precursor was cast and dried in room temp.

Figure 27A:
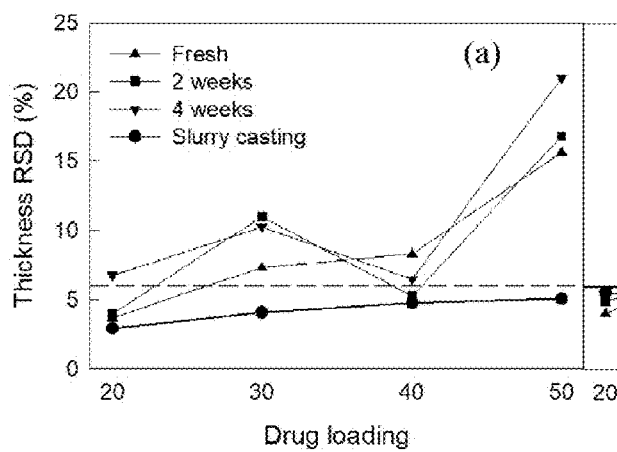
FIGS. 27A-B show relative standard deviation of solution films.
Figure 27B:
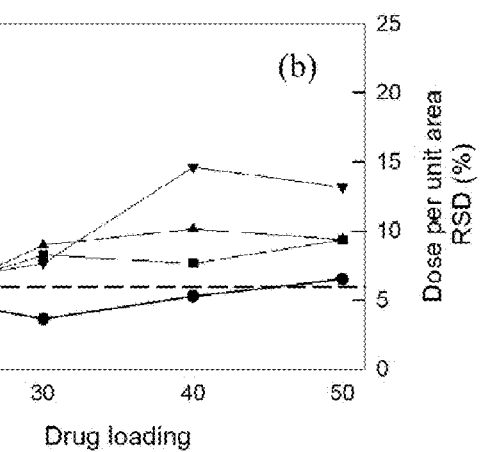
Figures 28A, 28B, 28C, 28D:
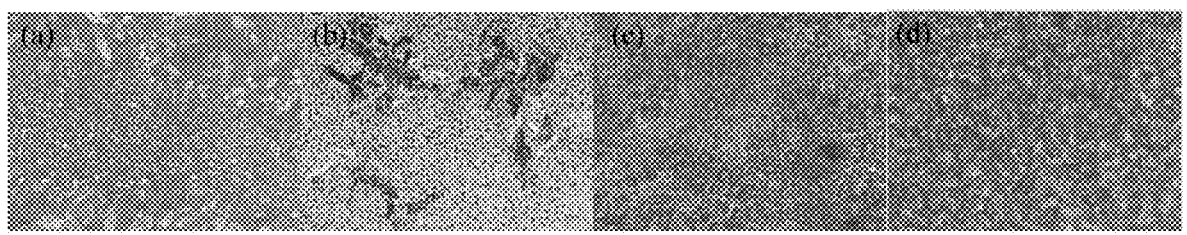
FIGS. 28A-D show digital microscope images of different drug loading solution films.

The relative standard deviation (RSD %) for film thickness, drug mass per area of slurry films and solution films at 20%, 30%, 40%, and 50% drug loadings are shown in FIGS. 27A-B. In order to evaluate the stability of solution films, the content uniformity of fresh, 2 weeks stored and 4 weeks stored films were utilized. The RSD of thickness and dose per unit area of slurry films at all drug loadings are below 6%. In the contrast, the RSD % of solution films at high drug loading, larger than 20%, are higher than 6%. And the RSD of thickness of 50% solution films are more than 15%. As the solution films being stored 4 weeks at room temperature and humidity ambient, the RSD % of dose per unit area of 40% and 50% increased to 15%.

FIGS. 28A-D show the microscope images of solution casting films of 20% to 50%. As shown in the images, drug crystals appear in the all drug loading films, indicating the dissolved FNB drug particles recrystallized in after casting and drying processes.

Figure 29:
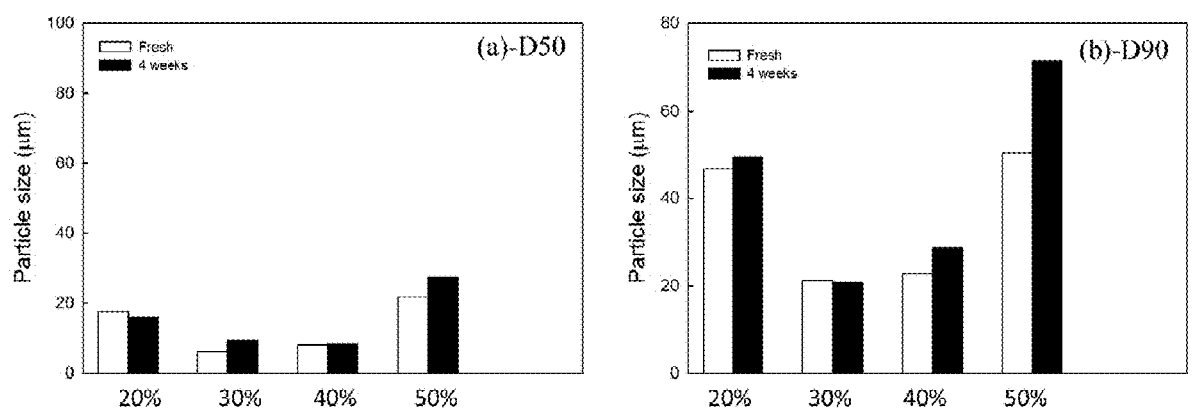
FIG. 29 shows redispersion particle size of different drug loading solution films.
Figure 30:
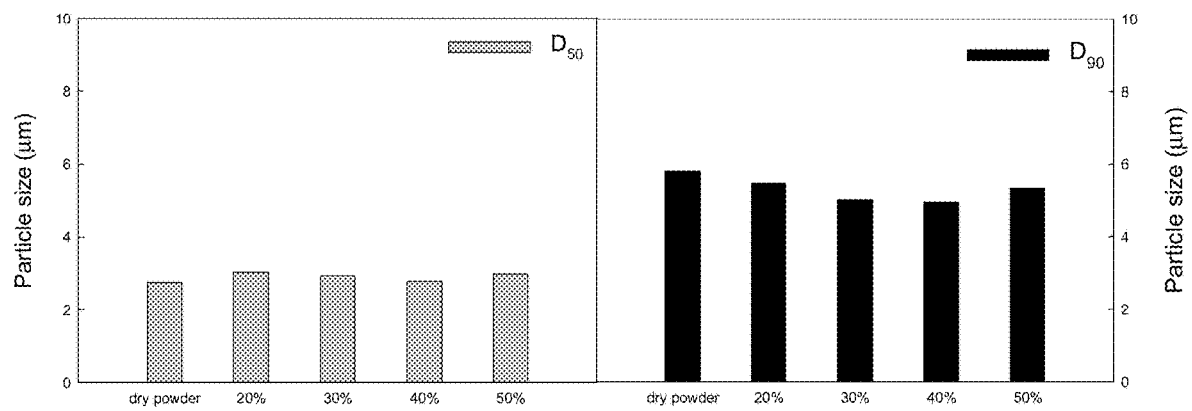
FIG. 30 shows redispersion particle size of different drug loading slurry films.
Figures 31A, 31B, 31C, 31D:
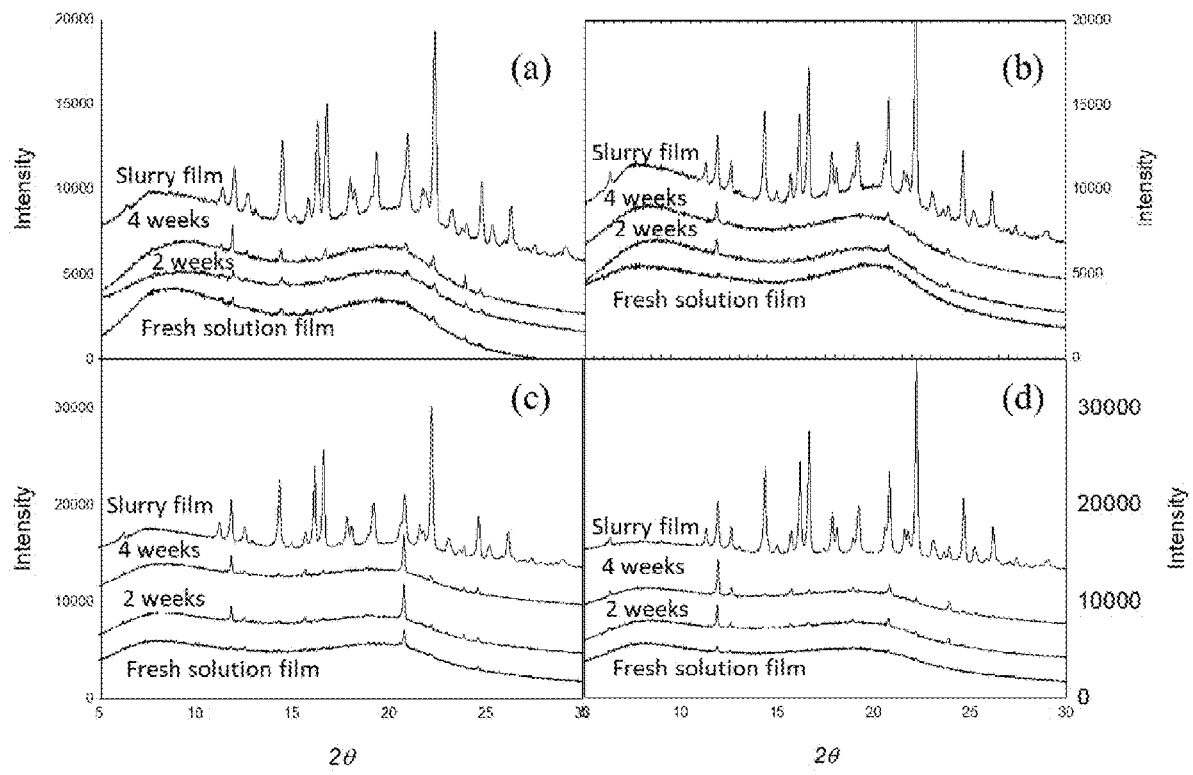
FIGS. 31A-D show XRD patterns of slurry and solution films.

FIGS. 29 and 30 show the redispersion particle size (D50 (left) and D90 (right)) from solution films and slurry films. As shown in FIG. 29, the redispersed particle size of solution films are not stable, varying from around 10 μm to around 36 μm for D50, and around 20 μm to 80 μm for D90. They are far away from the particle size of dry FNB powder. While the redispersed particle size of slurry films are comparable to the original particle size of surface modified micronized drug powders even at high drug loadings, around 4 μm for D50 and 6 μm for D90.

FIGS. 31A-D show the XRD spectra of slurry films and solution films at 20% to 50% drug loadings. All slurry films show high intensity of FNB peaks and the humps of HPMC polymer. Regarding to the spectra of solution films, only a few FNB peaks appeared with very low intensity indicating the amorphous state of FNB in the film matrices but not 100%. The peaks of solution films suggest the small percentage of crystal state of FNB in the film matrices.

Figure 32A:
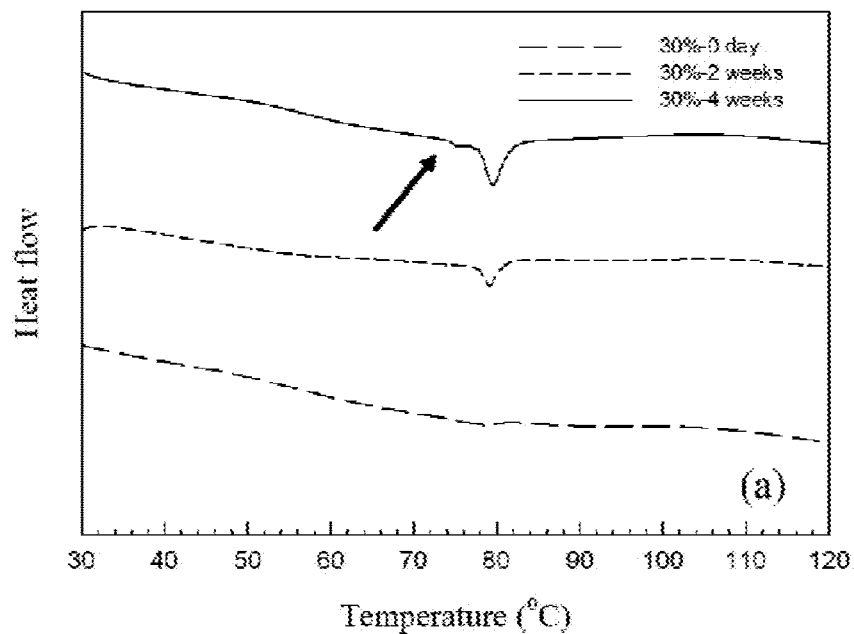
FIGS. 32A-B show DSC curves of solution films.
Figure 32B:
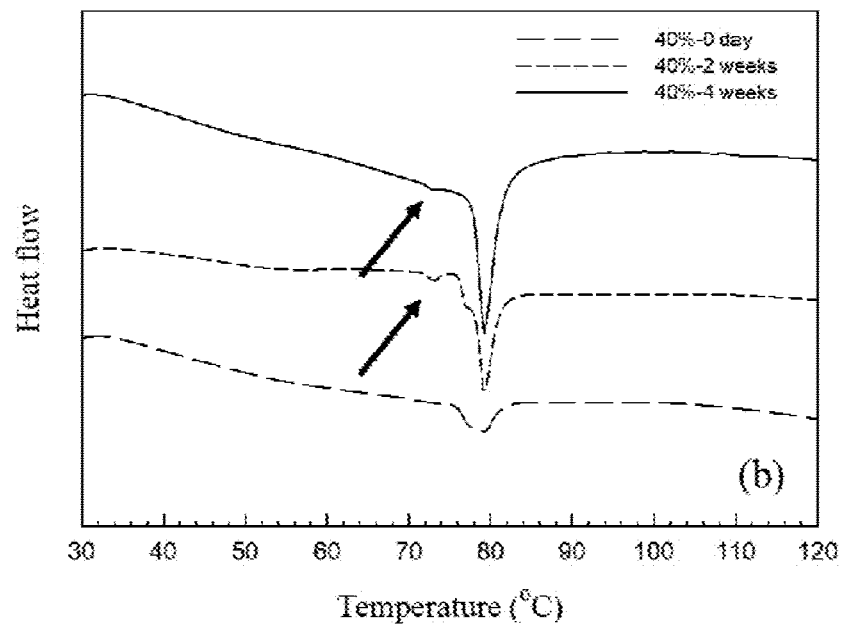

DSC was also used to assess the states of FNB in the solution films. FIG. 32A-B are DSC curves of 30% and 40% solution films. As the films were stored, the melting peak of FNB increased and one more peak at 74° C. can be observed in both curves, indicating the metastable crystalline form II of FNB appeared in the recrystallization process. However, the form II is not detected in the 20% and 50% films. Recrystallization of amorphous FNB is unpredictable in the casting and drying process.

Dissolution profiles of slurry and solution films at 20% to 50% drug loadings were compared in FIGS. 33A-D. It was not surprising that solution films released faster than slurry films, except the 50% drug loading film which the release rate of slurry film is similar to solution film.

Figure 34A:
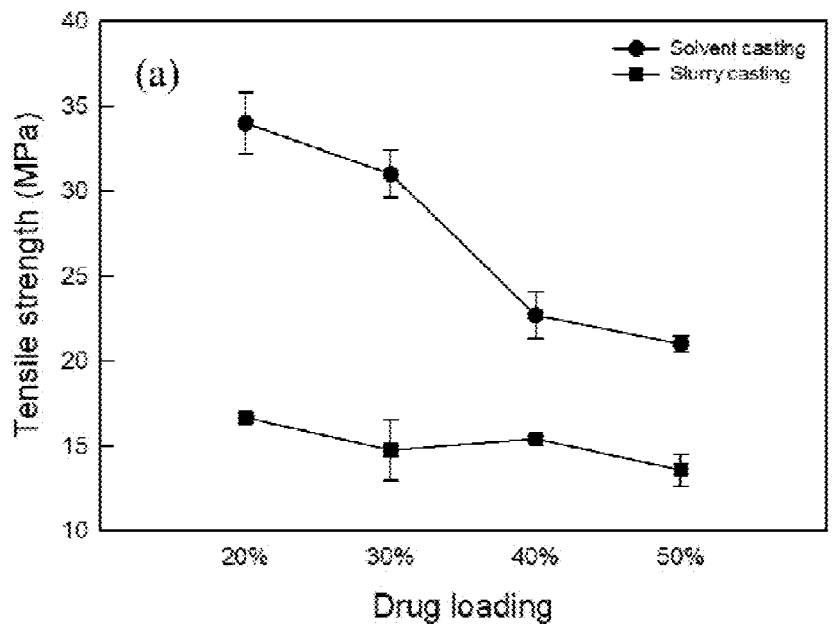
FIGS. 34A-C show mechanical properties of slurry and solution films at different drug loadings.
Figure 34B:
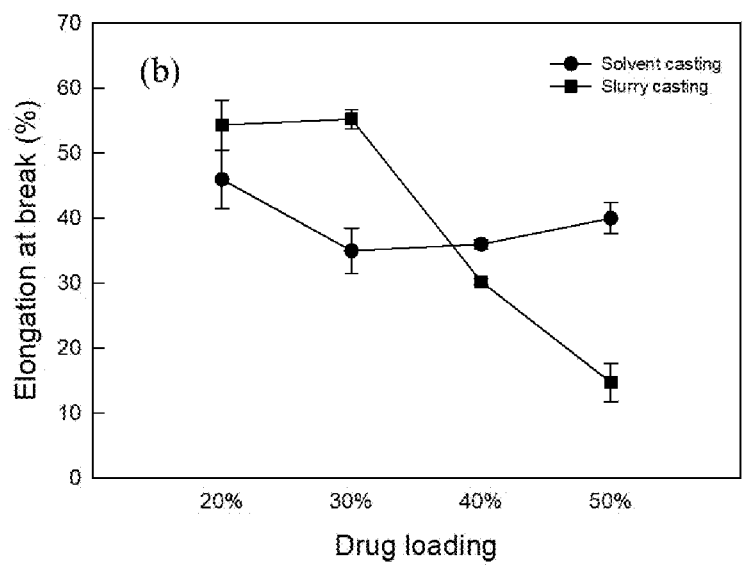
Figure 34C:
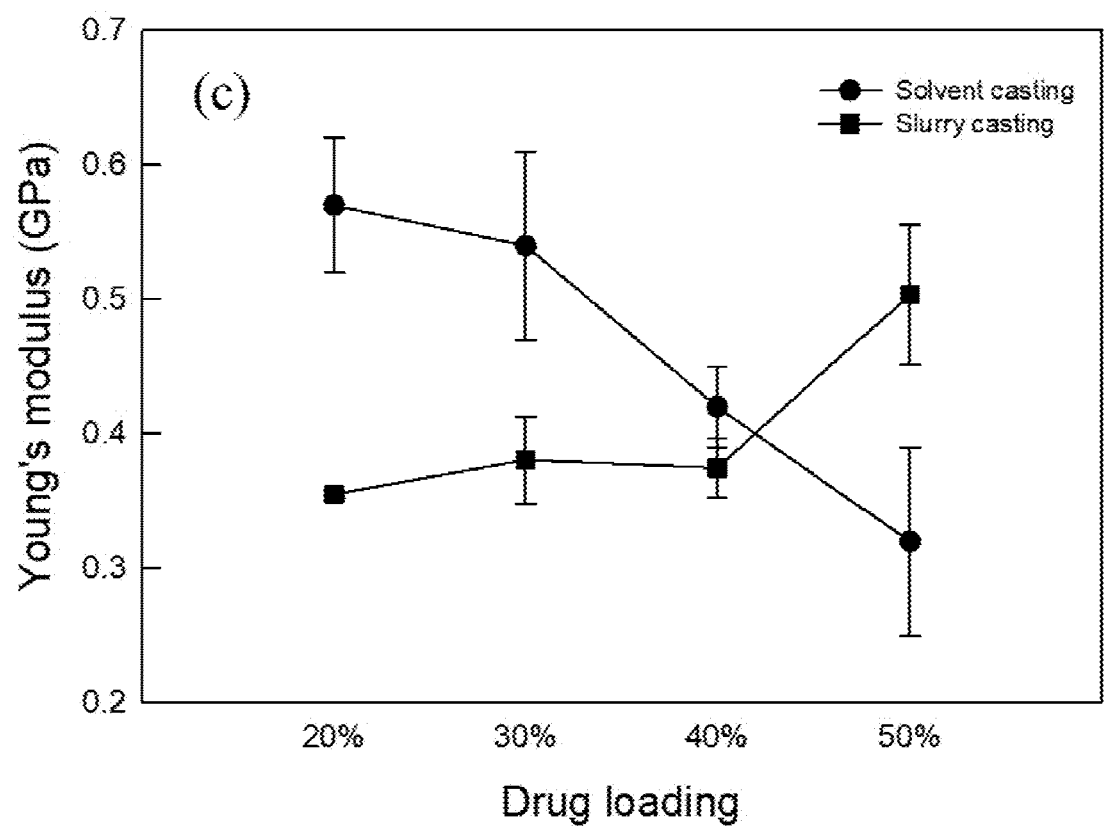

FIGS. 34A-C show the mechanical properties of slurry and solution films. From the results, slurry films have lower tensile strength than solution films, from around 13 MPa to 17 MPa for 20% to 50% drug loadings. Regarding the elongation percentage, slurry films are from 55% to 14% and solution films are from 45% to 33% for 20% to 50% drug loadings. Young's modulus of slurry films increased as drug loading increased; to the contrary, YM of solution films decreased as drug loading increased. Slurry cast films are ductile and strong.

Example 9: The Effect of Mixing Process Parameters on Critical Quality Attributes (CQAs) of Polymer Strip Films Processed by Three Different Mixer Types Three different mixer types were used in this project namely, impeller, planetary (ARE-310, THINKY, USA) and high intensity vibratory mixer (Resodyn Acoustic Mixers, Inc., Butte, Mont., USA).

Each mixer type was evaluated by its processing parameters; e.g., speed and time. The processing parameters were chosen using a Taguchi L9 Orthogonal Array.

Composition of film precursor suspensions used in this study are shown in Table 12, below.

TABLE 12

Composition of film precursor suspensions and low shear (2.2 s$^{-1}$) viscosity at room temp:

| Run no. | Wt. % HPMC | Wt. % Glycerin | Wt. % Water |
|---|---|---|---|
| 1 | 12 | 4 | 79 |
| 2 | 12 | 4 | 83.5 |
| 3 | 12 | 4 | 83.9 |

TABLE 12-continued

Composition of film precursor suspensions and low shear (2.2 s$^{-1}$) viscosity at room temp:

| Run no. | Wt. % FNB in Film Precursor | Film Precursor Suspension Viscosity (Cp) | Target FNB Loading in Film (Wt. %) |
|---|---|---|---|
| 1 | 5.0% | 11.74 ± 0.16 | 22.7 |
| 2 | 0.50% | 8.10 ± 0.22 | 2.88 |
| 3 | 0.10% | 7.70 ± 0.25 | 0.59 |

A standard table known as a Taguchi L9 orthogonal array with three levels and three factors (shown in Table 13) was used for the design of the experiments. For film manufacturing, mixer types and their processing conditions, e.g., mixing speed/time are some important parameters in terms of content uniformity. Taking this into consideration, mixer type, mixing speed and time were studied as factors with three levels that are namely high, middle and, low corresponding to the related factors of each mixer type. It is worth mentioning that each of the mixer types has a different performance range.

TABLE 13

Design of processing parameters by Taguchi L9 orthogonal array:

| Factors | Level 1 | Level 2 | Level 3 |
|---|---|---|---|
| Mixer Type | Impeller | Planetary | HIVM |
| Mixing Speed | Low | Medium | High |
| Mixing Time | Slow | Intermediate | Fast |

HIVM: High intensity vibratory mixer

For the sake of the evaluation for effect of the mixer types and their processing parameters, the formulation that was used for film forming was fixed. For this end, the viscosity aqueous polymer solution contained 12% HPMC-E15LV (wt %) and 4% glycerin (wt %), and as-received fenofibrate particles (AR-FNB) (5%) were used. Later, the mixed precursors were cast at 900 to 1000 microns opening using a doctor blade (3700, Elcometer, USA) and dried in a drier chamber (TC-71LC, HED International, NJ, USA).

Figure 35:
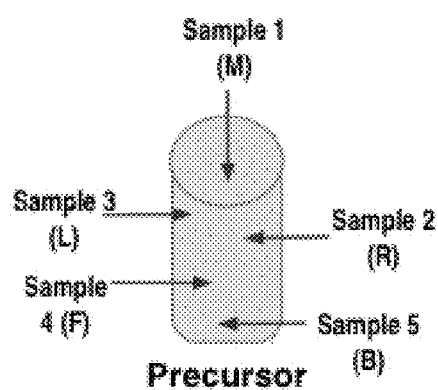
FIG. 35 shows a schematic of film precursor suspension homogeneity sampling and assessment. M: Middle, L: Left (surface), R: Right (surface), F: Front (bottom), B: Back (bottom)

Accurate prediction of the product properties based on design process parameters was tested with both homogeneity and content uniformity from each precursors and films, respectively. To test the precursor uniformity, 50 mg sample amount from five different points of the precursor, namely middle, left surface, right surface, front bottom, and back bottom were measured (FIG. 35).

Figure 36:
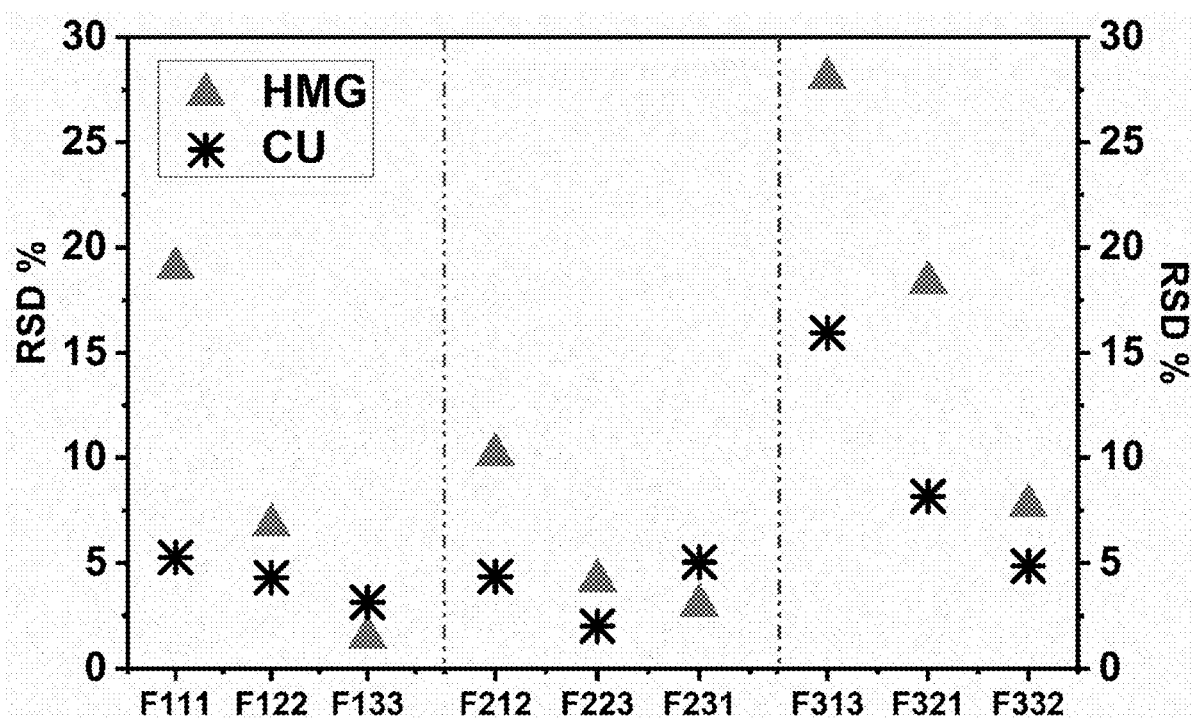
FIG. 36 shows a comparison of homogeneity and content uniformity test vs. RSD % with FNB loaded precursors and films, respectively.

Each sampled precursor was dissolved in 50 ml of 7.2 mg/ml SDS and the solution was stirred until the drug was dissolved. Later, drug content was tested using a UV spectrophotometer (Thermo Fisher Scientific Inc.). To test the uniformity of the end product, 10 circular samples ⅜" in diameter were punched from each of the film, and transferred in 100 ml of 7.2 mg/ml SDS. The content uniformity of film was tested using an UV spectrophotometer. FIG. 36 shows the comparison between precursor and film uniformity.

Homogeneity is an important intermediate-CQA, as the uniformity of the precursor product may reflect the quality of the final product. Such intermediate-CQAs could potentially be very important in the industrial scale continuous production of strip-films, because they may allow for the manufacturer to monitor the quality of the product without interrupting production.

FIG. 36 shows the homogeneity test results. The homogeneity of the precursor solution produced via impeller mixing showed a correlation between mixing time and speed and uniformity of the precursor. The results showed that increased mixing time and increased mixing speed (F133) for the impeller mixer resulted in a more homogenous precursor (1.59% RSD).

However, the lowest mixing time/speed (F111) and the medium mixing time/speed (F122) both resulted in a precursor with % RSDs above 5% for impeller mixing. Precursor produced via planetary mixing showed a correlation between mixing speed and precursor uniformity; increased mixing speeds (F223, F231) resulted in more homogeneous precursors (RSD, 4.19 and, 3.03, respectively).

For this mixing type, the lowest mixing speed (F212) resulted in a precursor with a % RSD above 5%. This correlation was also seen for the HIVM, however the tested conditions resulted in precursors with % RSD values greater than 5% while increased mixing speed had slightly better homogeneity with a % RSD, 7.75.

Generally, a precursor that displays increased homogeneity will result in a more homogenous final product. However, precursors showing an RSD above 15% can still result in a final product with an acceptable RSD. An effective drug delivery platform should deliver the API reliably and consistently. To this end it is essential that not only the dosage form contain the indicated amount of drug, the drug must also be uniformly distributed.

The effect of CPPs on the content uniformity of dry film was also evaluated and was compared to the homogeneity results (FIG. 36). In addition, acceptance values (AV) of each parameter were included. Between the three mixing methods, several trends emerged from the different processing parameters.

For impeller mixing, the lowest mix speed and lowest mix time (F111) resulted in the least uniform final product, albeit the RSD % was still acceptable (less than 6%). Increased mix time and speed improved the uniformity of the final products, with F133 (high mix time and speed) producing the most uniform result (RSD %: 3.1%).

However, the acceptance value (AV) for F111 of 25.26, indicates that while the API in the film was uniformly distributed, the film did not have the desired drug loading. The observed drug loading was 19.56% while the theoretical value was 22.73%. This indicated that these processing parameters were not able to properly mix the precursor.

It was observed that drug particles adhered to the walls of the vessel, which resulted in a lower drug amount than that of the label claim. When the planetary mixer was used all of the mixing conditions were able to produce uniform film. Notably, F223 produced a % RSD of 2.0, and an AV of 10.26, both of which are acceptable. However, F231 while producing a slightly higher % RSD (5.1), had a better AV (4.72). This may indicate that there is an optimum combination of mixing speed and time for planetary mixing that falls between the tested conditions.

For HIVM mixing, for the less intense conditions evaluated, F313 and F321, not only failed to produce uniform films, as indicated by their % RSD values 15.5% and 8.0% respectively, they also did not contain the desired amount of drug, as shown by their AV 91.19 and 25.87, respectively.

During the HIVM mixing process it was observed that powdered drug adhered to the top of the mixing vessel and failed to enter the precursor solution. This indicates that the low mixing times/speeds are unable to properly mix the precursor solution. However, HIVM mixing successfully produced uniform film at the highest mixing time and medium speed (F332), as indicated by its RSD % value of 4.87 and AV of 6.07.

Figure 37:
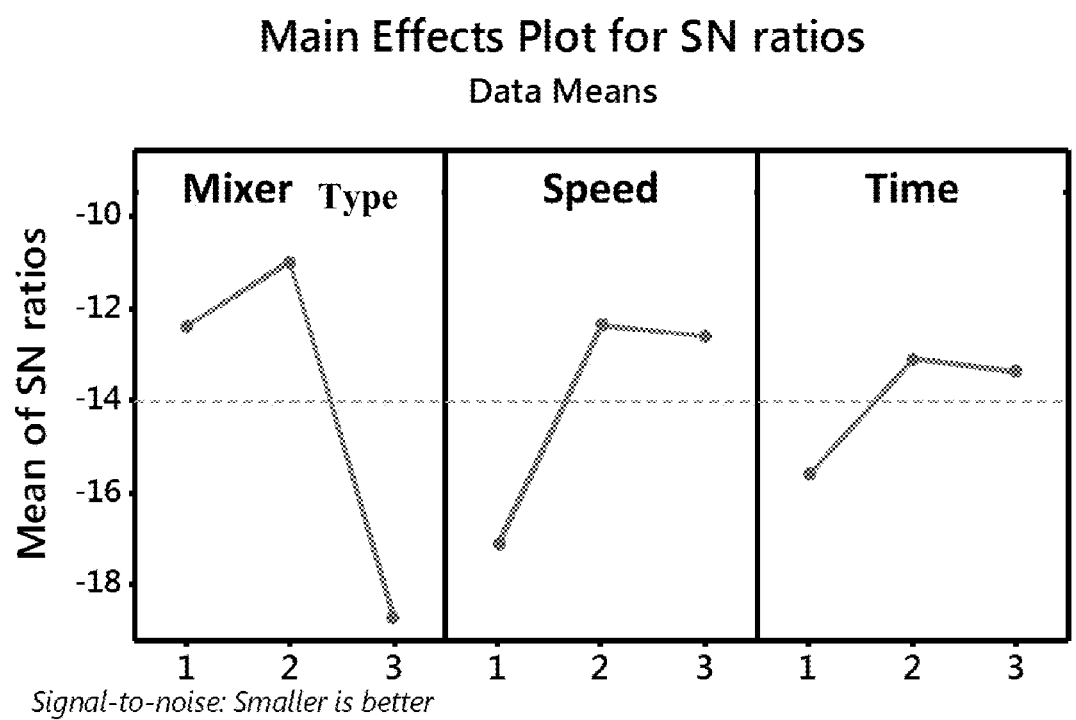
FIG. 37 shows the main effects plot for content uniformity.

Optimization of the mixing processing parameters was considered to achieve the highest level of drug content uniformity in the end product. The main effects plot for content uniformity was created by using the "smaller the better" characteristic and are shown in FIG. 37. The highest values in the main effect plot, F222, represent the maximum contribution to minimize the RSD % values.

The optimum parameters, F222, correspond to planetary mixer with 1500 rpm mixing speed with 10 min mixing time. The same procedure for the content uniformity was followed in order to analyze optimum parameters dictated by Taguchi Design. According to the experimental result of F222, 3.13% RSD and AV of 4.59 was obtained.

Figure 38A:
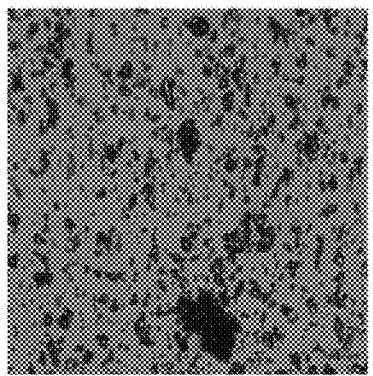
FIGS. 38A-38C show that digital microscopy was used to visualize the extent of drug particle agglomeration in the dried film.
Figure 38B:
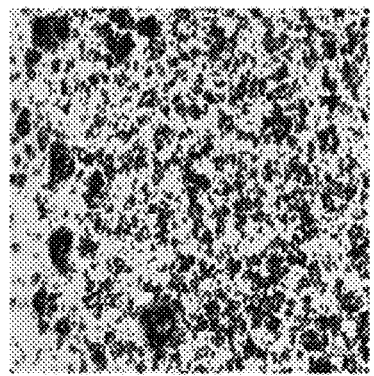
Figure 38C:
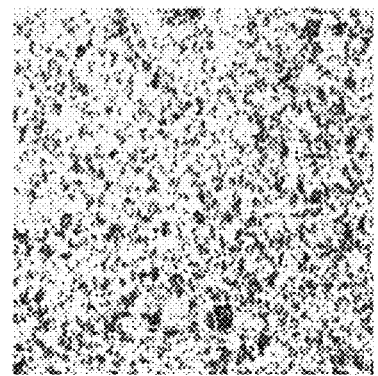

Digital microscopy was used to visualize the extent of drug particle agglomeration in the dried film. There was a direct correlation between the mix conditions that produced poor content uniformities and final products with observable particle agglomeration. This effect can be seen with images taken of film produced by F313, FIG. 38A, where there are large and irregularly distributed agglomerations.

In comparison, films created using planetary mixing showed more uniform distribution of drug particles in the polymeric matrix. For impeller mixing, the extent of agglomeration in the final product decreased with increased mixing times/speeds.

Generally speaking, a film should have a high enough TS and % EB to ensure that it is robust enough to survive the stresses associated with production and transport.

However, these properties should be combined with a lower YM, as an overly stiff film may cause discomfort to the patient.

The tensile strength (TS), yield strength (YS), Young's Modulus (YM) and elongation at break (EB %) are shown in Table 14 below. TS was not negatively affected by the different mixer types or mixing conditions.

Films with more uniform drug dispersion, had higher EB % values and less uniform films had lower EB % values. For example, films prepared by impeller mixer (F111) and HIVM (F321) with the shortest mixing time had low EB %, 36.9% and 33.5%, respectively. Moreover, the films with the lowest mixing speed (F313) and, middle mixing speed (F122) had the highest SDs.

TABLE 14

Tensile strength and percent elongation at break of FNB loaded films with fixed thicknesses (0.12-0.13 mm):

| | Tensile strength (MPa) | Yield strength (MPa) | Young's modulus (Gpa) | Elongation at break (%) | Thickness (µm) |
| --- | --- | --- | --- | --- | --- |
| F111 | 16.1 ± 1.9 | 13.3 ± 1.4 | 0.5 ± 0.1 | 36.9 ± 8.0 | 124.7 ± 3.3 |
| F122 | 17.0 ± 0.7 | 12.7 ± 0.8 | 0.6 ± 0.1 | 46.8 ± 9.9 | 129.0 ± 2.3 |
| F133 | 17.4 ± 0.8 | 12.9 ± 0.6 | 0.5 ± 0.0 | 45.5 ± 2.4 | 126.5 ± 1.9 |
| F212 | 16.1 ± 0.7 | 12.0 ± 0.7 | 0.4 ± 0.1 | 40.5 ± 3.4 | 125.8 ± 1.2 |
| F223 | 17.7 ± 0.6 | 12.1 ± 0.5 | 0.5 ± 0.1 | 53.5 ± 4.0 | 123.4 ± 2.5 |
| F231 | 15.1 ± 0.8 | 11.2 ± 0.4 | 0.5 ± 0.1 | 48.0 ± 7.0 | 124.5 ± 2.6 |
| F313 | 17.8 ± 0.5 | 13.5 ± 0.8 | 0.5 ± 0.0 | 41.2 ± 9.8 | 124.0 ± 2.9 |
| F321 | 15.5 ± 0.8 | 12.4 ± 0.9 | 0.6 ± 0.2 | 33.5 ± 4.8 | 125.0 ± 3.2 |
| F332 | 18.6 ± 1.2 | 13.4 ± 0.7 | 0.6 ± 0.1 | 51.4 ± 5.9 | 127.7 ± 1.0 |

Figures 39A, 39B, 39C:
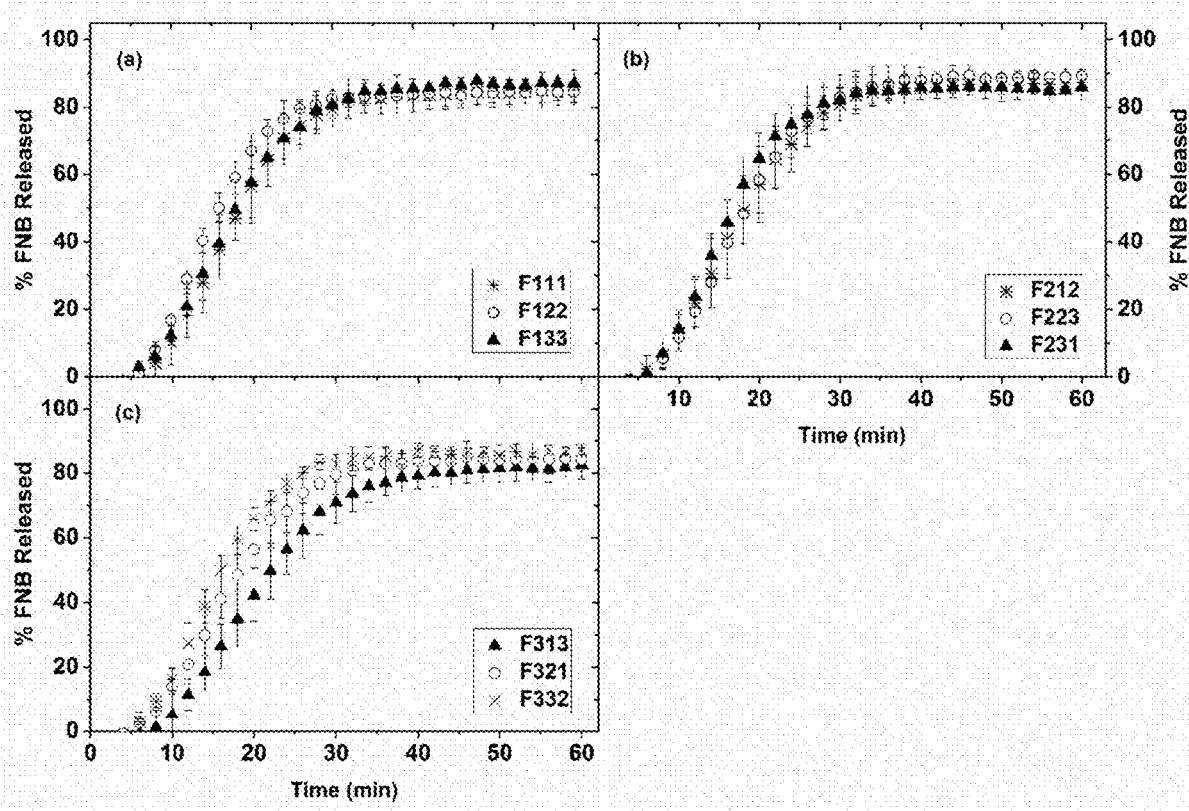
FIGS. 39A-39C show the dissolution profiles of the strip-films containing FNB particles.

The dissolution profiles of the strip-films containing FNB particles are shown in FIGS. 39A-39C. Changing mixing parameters had substantially no negative impact on drug release profile on the strip-films. The films showed fast release behavior (greater than 80% dissolved in 30 min) for poorly water soluble FNB with the only exception being HIVM with low mixing intensity and high mixing time (F313). This exhibited a slight decrease in dissolution rate. This can be attributed to the agglomeration issue for poor mixing condition.

Failure to select proper mixing parameters, (e.g., combination of mixer type, intensity, and time), is likely to result in a poor dispersion of drug particles in both the film precursor and final product, which would result in an infeasible final product. There was little or no difference in dissolution behavior between films prepared with the different processing conditions. However, mechanical properties of the films showed a difference in EB %, indicating insufficient mixing parameters might negatively affect the product structure.

On the other hand, the suggested mixer type and mixing parameters can be used to obtain the most uniform final product as well as good mechanical properties with little or no impact on drug release profile. These conclusions are most likely impacted due to the use of larger, as received and non-functionalized particles, which are expected to pose a bigger challenge for the mixing process.

Example 10: Investigation of the Effect of Aqueous of Polymer Solution Mixing with Twin Screw Extruder (TSE) on Uniformity of the Film Product The mixing efficiency for aqueous feedstock of strip film was tested using a twin screw extruder (Leistritz Extrusionstechnik GmbH, Nurnberg, Germany)). The aqueous polymer solution contained 12% HPMC-E15LV (wt %) and 4% glycerin (wt %). 2% hydrophilic silica (A-200) hydropobic silica (R972P) (Evonik, U.S.A.) was utilized for the surface modification of fenofibrate (C-FNB). The composition of dry film including processing conditions are presented in Table 15.

Aqueous polymer solution and the C-FNB particles were mixed with continuous mixing at room temperature. The processing parameters were chosen to be 300 rpm, 400 rpm and 500 rpm. These parameters prevented the twin screw from back flowing and allowed for the obtainment of a practicable feedstock for strip film product. The mixed drug-polymer precursor was cast at 900 to 1000 microns using a doctor blade (3700, Elcometer, USA) and dried in a drier chamber (TC-71LC, HED International, NJ, USA).

To test the uniformity of feedstock (precursor) and end product (strip film), homogeneity and content uniformity tests were performed and evaluated the feedstock uniformity as well as thickness and mass of drug per unit area (Table 15).

That said, both of the processing parameters of films exhibited less than 6% RSD in terms of film thickness and FNB mass per unit area. It is worth the mention that, although the residence time of mixing process in the twin screw was around 40 s, the product had excellent uniformity based on content uniformity results.

TABLE 16

RSD % Thickness, drug content and uniformity variation in dry film processed by Twin Screw Extruder:

| Formulation | Dry Film Thickness (μm) | RSD % | Drug mass per unit area (mg/cm$^2$) | RSD % | wt % API | RSD % |
| --- | --- | --- | --- | --- | --- | --- |
| F1 | 101.30 | 1.68 | 1.60 | 4.04 | 11.15 | 3.86 |
| F2 | 106.40 | 1.01 | 2.78 | 1.94 | 18.44 | 1.03 |
| F3 | 100.90 | 2.74 | 2.82 | 3.31 | 20.19 | 2.54 |
| F4 | 102.60 | 0.94 | 2.53 | 1.15 | 18.68 | 1.13 |
| F5 | 106.20 | 1.32 | 2.20 | 1.76 | 15.50 | 2.02 |
| F6 | 104.70 | 2.55 | 2.61 | 3.72 | 18.52 | 2.33 |
| F7 | 117.90 | 4.69 | 2.68 | 3.31 | 17.36 | 1.22 |
| F8 | 120.40 | 4.59 | 2.38 | 4.13 | 16.29 | 1.18 |
| F9 | 106.60 | 5.75 | 2.44 | 6.17 | 17.39 | 2.35 |

Figure 40:
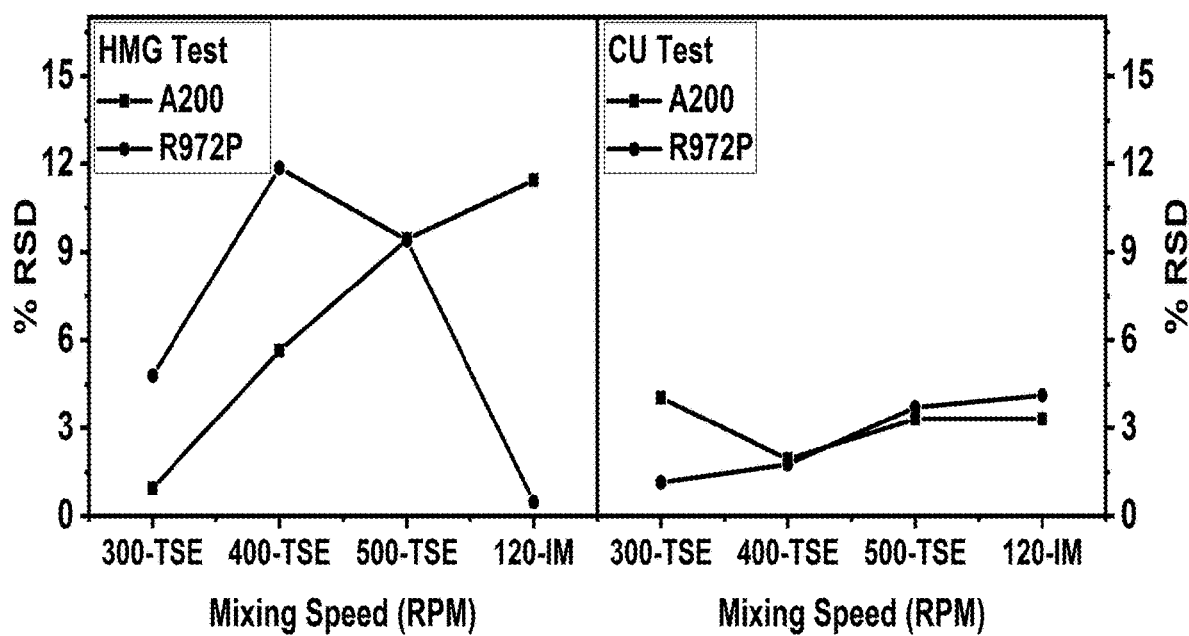
FIG. 40 shows that the feedstock showed relatively larger RSD % results than the content uniformity of end product.
Figures 41A, 41B, 41C, 41D:
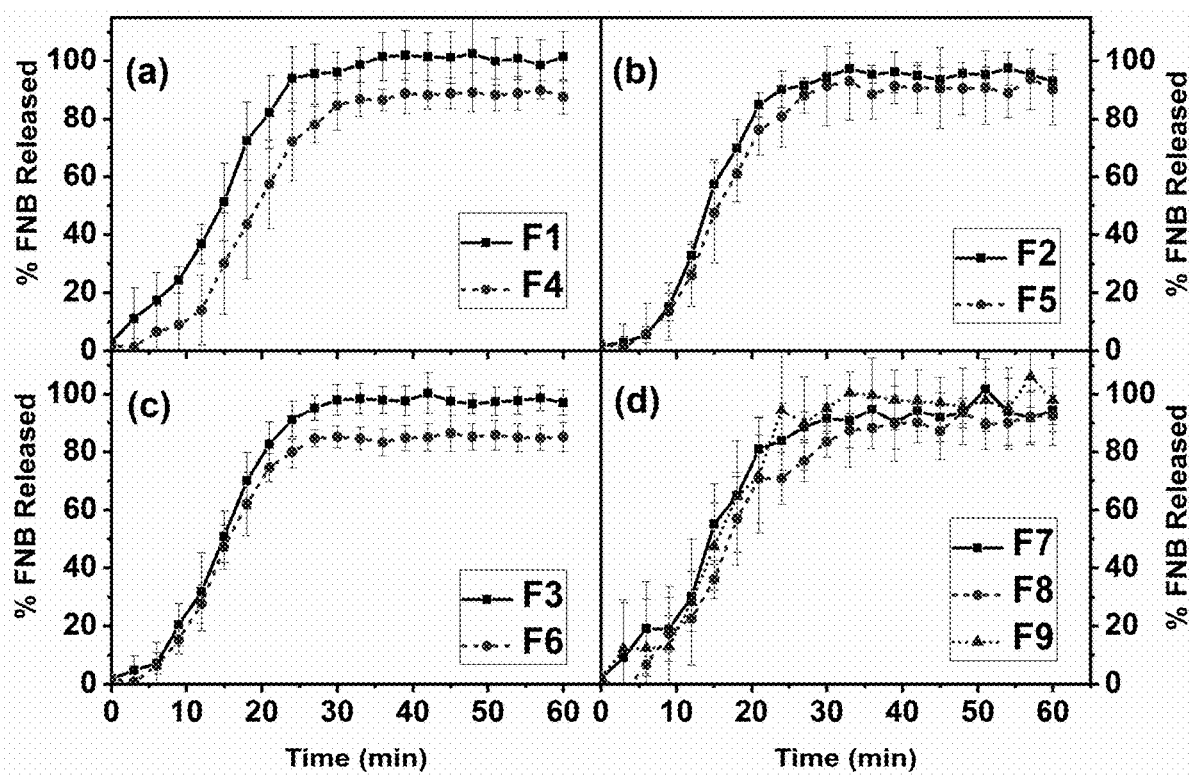
FIGS. 41A-41D show the comparison between continuous mixing with twin screw extruder (TSE) and batch mixing with Impeller mixer.
Figures 44A, 44B, 44C, 44D:
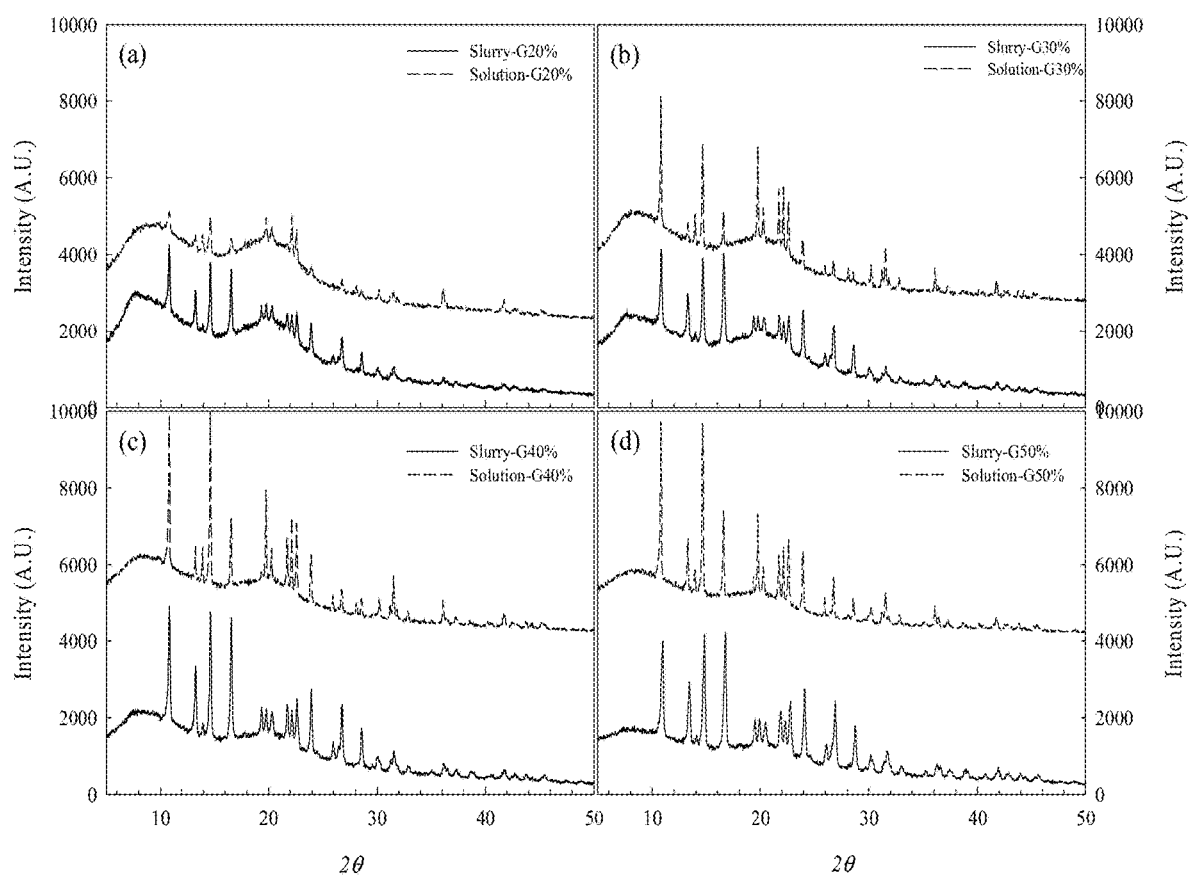
FIGS. 44A-44D show XRD of solution and slurry films laden with GF.

The feedstock showed relatively larger RSD % results than the content uniformity of end product (FIG. 40). It should be pointed out that, to mimic the dosage amount of end product in uniformity test, smaller sample sizes (50 mg) were used in the homogeneity test. Better results may be obtained with feasible sample size.

The dissolution profile of the dry films loaded with MC-FNB including hydrophilic and hydrophobic silica were examined. In addition, the comparison between continuous mixing with TSE and batch mixing with Impeller mixer was shown in FIGS. 41A-41D. The dry film loaded with MC-FNB containing hydrophilic silica showed slightly better drug release.

It is important to mention that TSE demonstrated a good performance for polymer films compared to the impeller mixer although the residence time in TSE was around 30 s while impeller mixer took 3h.

These results are promising for the continuous manufacture process within aqueous polymer solution to produce uniform films with varying processing parameter.

Example 11: Investigation of Continuous Film Manufacturing with Drug Particles Dispersed in Molten Polymer Matrix Via Twin Screw Extruder The system of Example 10 was used in this example (Example 11), but without using aqueous polymer solutions.

TABLE 15

Composition of dry film including processing conditions:

| Formulation | API sample | Glidant | SAC % | Target FNB loading in dry film (wt %) | Mixer Type | Mixing Speed (rpm) | Residence Time |
| --- | --- | --- | --- | --- | --- | --- | --- |
| F1 | MC-FNB | A200 | | | TSE | 300 | 31 s |
| F2 | MC-FNB | A200 | | | TSE | 400 | 30 s |
| F3 | MC-FNB | A200 | | | TSE | 500 | 29 s |
| F4 | MC-FNB | R972P | 30% | | TSE | 300 | 31 s |
| F5 | MC-FNB | R972P | | 18.00% | TSE | 400 | 30 s |
| F6 | MC-FNB | R972P | | | TSE | 500 | 29 s |
| F7 | MC-FNB | A200 | | | IM | 120 | 3 h |
| F8 | MC-FNB | R972P | | | IM | 120 | 3 h |
| F9 | MUC-FNB | N/A | N/A | | IM | 120 | 3 h |

Molten polymer was used instead through use of higher processing temperatures such that the process was below the melting point of the API, but above the melting point of polymer and plasticizer.

Aside from using the rod die, a sheet die was also used for the continuous production of strip films, where drug particles (with or without surface modification) together with polymer and plasticizer were fed as a physical mixture into the co-rotating twin-screw extruder (Leistritz Extrusionstechnik GmbH, Nürnberg, Germany).

Here, different from the method where aqueous polymer solution was used, the drug particles are dispersed into a continuous molten polymeric matrix inside the extruder at high operating temperature, and then pushed through a sheet die. In this example, griseofulvin (GF) was used as a model BCS Class II drug, hydroxypropyl cellulose (HPC, L grade) was used as the polymeric matrix, and poly(ethylene glycol) (PEG 3350) was used as the plasticizer.

The produced film was found to have excellent RSD and mechanical properties. In addition to those used, other plasticizers such as glycerin, poly(ethylene oxide) (PEO N10) were also found to be acceptable. Use of surface modified and micronized GF and other APIs were found to help provide desirable film or feedstock properties. When produced as filaments, these materials were found usable in 3D printing using a fused deposition modeling printer.

Example 12: Comparison Between Slurry Casting and Solution Casting Techniques of Film Loaded with Poorly Water Soluble Drug Griseofulvin Solution casting films were prepared by dissolving HPMC-E15 LV in the water and acetone binary solution (1:4 w/w) at 50° C. and then mixing with GF drug particles in the THINKY mixer for 3 minutes. The resulting film precursor was cast and dried at room temperature.

Images of film solutions and the surface of dry films of GF are shown in FIGS. 42A-42H. The images are typical cases selected from many observations. FIGS. 42A-42D were film solutions before being cast into films and the amount of recrystallized drug particles increased with increased drug loading. Substantially no drug crystals can be observed in 20 wt % and 30 wt % film solutions and few drug crystals in the 40 wt % and 50 wt % film solutions.

Subsequently, FIGS. 42E-42H are surface images of GF dry films. Drug crystals can be found in GF loaded dry films indicating the drug recrystallized as the solvent evaporated during the drying process, and the amount of drug crystals increased with the increased drug loading.

In addition, the shape of recrystallized GF particles changed from needle shape to round shape when drug loading increased from 20 wt % to 50 wt %, revealing that the shape of the single recrystallized drug particle may be hindered in higher drug loads formulations.

The solution and slurry films laden with GF, the same intensity endothermic peaks around 175-190° C. were observed in FIGS. 43A-43D, showing the recrystallization of GF was clear and significant. As evident from the DSC profiles (FIGS. 44A-44D), the pure amorphous state of APIs cannot be preserved after film drying process, especially for GF.

Oppositely, the crystallinity of APIs in slurry films was maintained throughout the film manufacturing process.

It is noted that XRD analysis was also performed to study the physicochemical state of drugs incorporated in solution and slurry films. Regarding the films loaded with GF, only the 20 wt % film contained low-intensity peaks compared to the equivalent drug loaded slurry film. The other three solution films of 30 wt %, 40 wt %, and 50 wt % show the similar intensity of peaks in the range of 10-30° compared to slurry films, confirming the complete recrystallization of GF in the films.

Table 17 presents the content uniformity of films from the formulations including the average and relative standard deviation (RSD) values for thickness, drug amount per unit area, weight percentage of drug, and mean percentages of label claim (mean % LC). Most of the RSD values of GF films in terms of thickness, drug dose per unit area, and drug loading are below 6%, as well as mean % LC ranged from 90 to 110% with a large amount of recrystallized GF particles in the films after drying. These may be attributed to the high shear rate provided by the Thinky mixer which can distribute recrystallized GF particles uniformly in the film solutions.

TABLE 17

| Sample | Thickness (μm) | | Dose (mg/cm$^2$) | | Drug loading (wt %) | | Mean LC % |
|---|---|---|---|---|---|---|---|
| | AVG | RSD | AVG | RSD | AVG | RSD | |
| Slurry-20% | 94.3 | 5.4 | 2.3 | 5.2 | 17.4 | 3.1 | 87% |
| Slurry-30% | 102.0 | 5.7 | 3.4 | 4.3 | 27.8 | 6.3 | 93% |
| Slurry-40% | 93.4 | 3.8 | 4.5 | 1.4 | 37.5 | 3.3 | 94% |
| Slurry-50% | 90.0 | 5.4 | 6.0 | 5.8 | 50.4 | 2.1 | 101% |
| Solution-20% | 114.0 | 5.0 | 1.5 | 3.6 | 16.0 | 1.5 | 80% |
| Solution-30% | 109.0 | 6.0 | 3.4 | 5.4 | 29.0 | 4.0 | 97% |
| Solution-40% | 98.0 | 6.0 | 3.7 | 8.0 | 43.0 | 2.6 | 108% |
| Solution-50% | 97.0 | 4.6 | 4.0 | 5.8 | 45.0 | 6.9 | 90% |

Figures 45A, 45B, 45C:
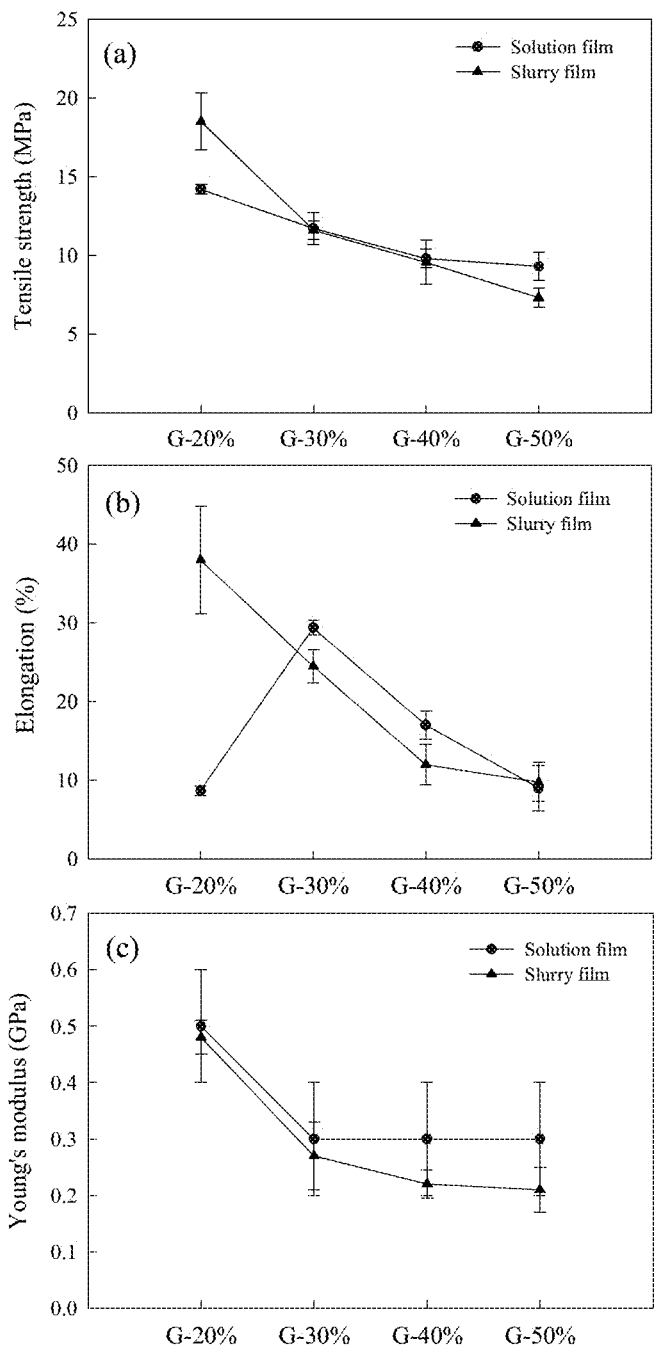
FIGS. 45A-45C show mechanical properties of slurry and solution films laden with GF.

The mechanical properties of tensile strength (TS), Young's modulus (YM) and elongation percentage (E %) of the films loaded with GF are shown in FIGS. 45A-45C. Solution films and slurry films containing GF exhibited similar TS, E %, and YM, except E % of 20 wt % GF loaded solution film, demonstrating the recrystallization of GF in the solution films was utter of high drug loaded films which is in line with DSC and XRD results. The low E % of 20 wt % solution film may be caused by the needle shape of recrystallized GF particles within film. Regarding the effect of drug loading, the TS, E %, and YM decreased as the drug loading increased for both solution and slurry films.

The impact of casting technique and drug loading on drug dissolution rate from a film matrix was examined. The results using 7.2 mg/ml SDS as the dissolution media are shown in FIGS. 46A-46D. Slurry films loaded with GF release faster than solution films, demonstrating the big recrystallized GF particles in the solution films greatly delay the drug release rate. With respect to the effect of drug loading on dissolution, slurry films release faster as drug loading increased which is attributed to the less polymer/drug ratio of high drug loading formulations.

In summary, solution films with dissolved drug inside have the advantage of faster release, but as a major disadvantage, stability of the drug form can be poor. Further, the recrystallized drug particles hinder the dissolution rate and the full dissolved of drug from higher drug loading films.

In contrast, for slurry cast films, the drug form is preserved and those films maintained the immediate release of drug particles from 20 wt % to 50 wt % drug loaded slurry films.

Figures 47A, 47B, 47C:
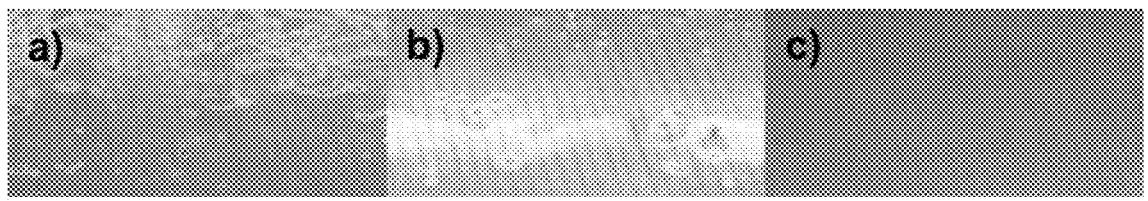

Example 13: Solution Casting Techniques of Film Loaded with Poorly Water-Soluble Drug Via Different Solvents When the films prepared with organic solvents are dried at relatively high temperatures (40 to 50° C.), irregularities may appear on the film surface due to the fast evaporation of the solvent. Pictures of the solution cast films dried at different temperatures are shown in FIGS. 47A-47C. FIG. 47A shows the film dried at 50° C. while FIG. 47B is at 40° C. and FIG. 47C is at 30° C. These irregularities cause non-uniformity of the thickness along the film and potentially non-uniformity of the drug content. Therefore, drying of the films at room temperature may be needed, which in turn increases the drying time up to 4 hours. However, in slurry casting, films can be dried at 50° C. leading to about one hour or less drying time for a 100 μm thick film.

Figure 48:
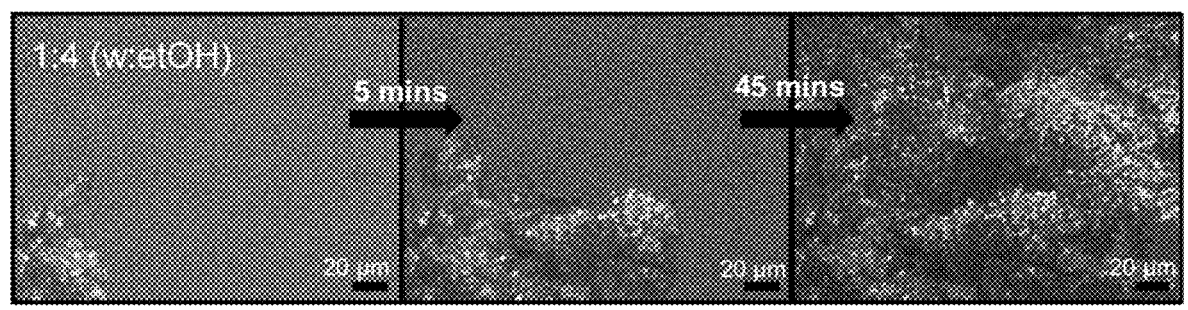
FIG. 48 shows optical images of films loaded with 10% fenofibrate; prepared with 1:4 (water:etOH) as solvent (images were taken during drying)

Optical microscope images of solution cast films during drying are presented in FIG. 48. FIG. 48 shows the recrystallization of the drug materials on the surface during the drying of the film made of 1:4 (water:etOH) with 10% FNB.

Figure 49:
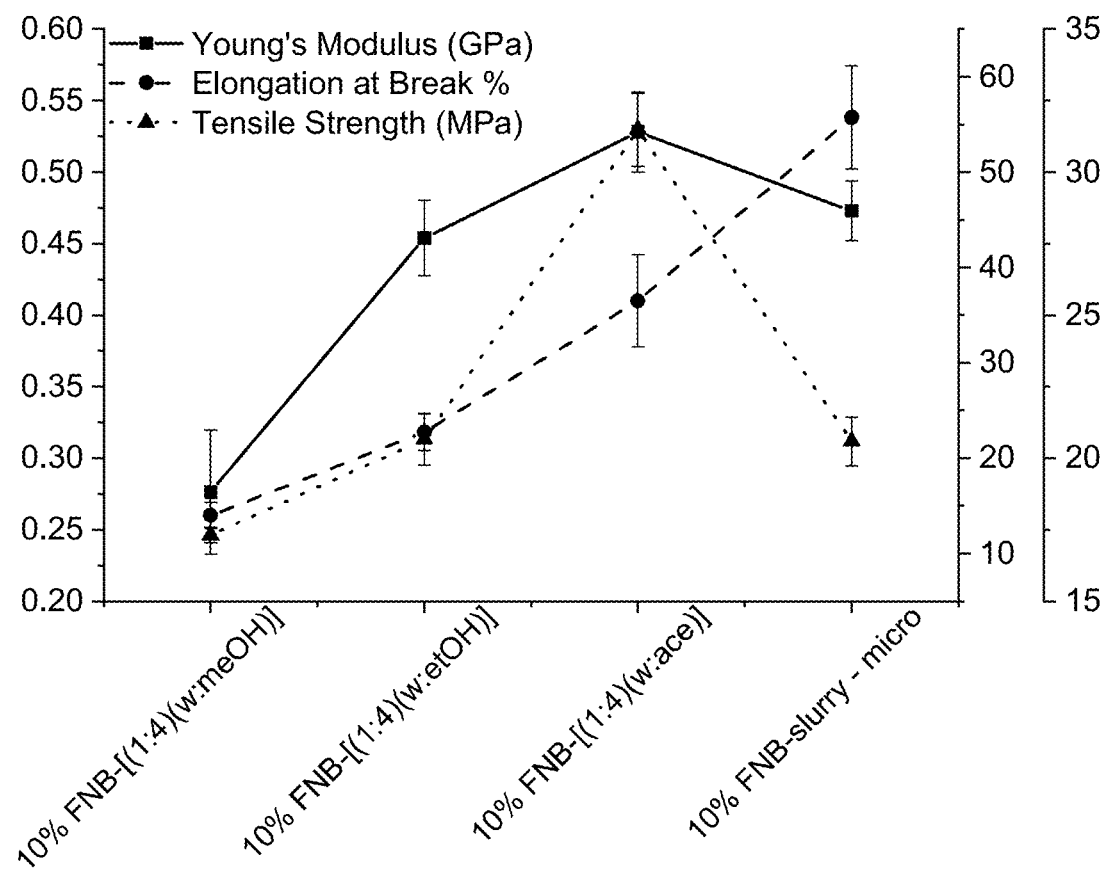
FIG. 49 shows mechanical properties of 10% FNB loaded solution casting films made of different solvents, slurry casting films loaded with 10% AR-FNB.

In FIG. 49, the solution cast films containing the same amount of polymer, plasticizer, and drug powder are compared in terms of mechanical properties. Despite the same composition, there are still some differences in the mechanical properties of the dried films prepared with different solvents (FIG. 49). A change of the solvent from the least solubilizing one in terms of drug to most solubilizing one, led to an increment in the mechanical properties of the film, e.g., young's modulus, elongation at break %, tensile strength.

Figure 50:
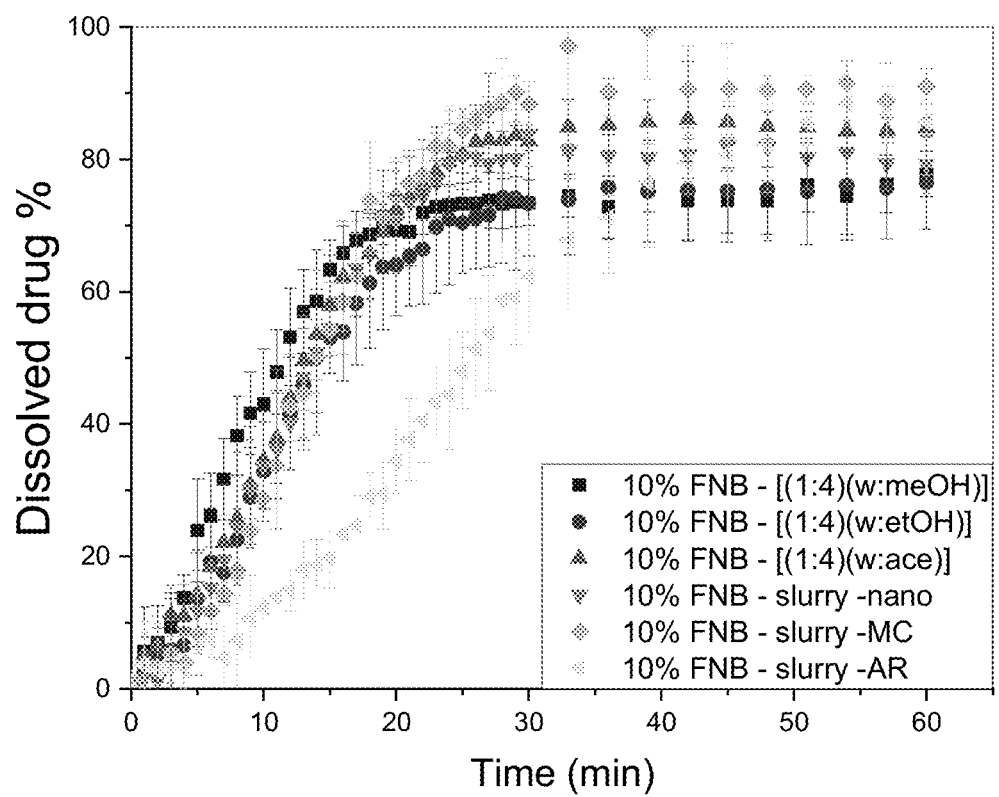
FIG. 50 shows dissolution profiles of 10% FNB loaded solution casting films made of different solvents and slurry casting films loaded with 10% as-received FNB, micronized-coated FNB, nano-sized FNB.

FIG. 50 compares dissolution profiles of different solution cast and slurry cast films. Except for the film loaded with as-received FNB, the other studied formulations exhibited statistically similar dissolution rates. It should be noted that the solid state of the drug and mechanical properties of the dried film may affect the dissolution profiles in general. The films prepared with a modification of the drug to enhance the dissolution rate had different mechanical properties and crystallinities yet showed quite similar dissolution profiles. The recrystallization and non-uniformity issues observed with solution cast films did not adversely affect the dissolution of the films.

Figure 51:
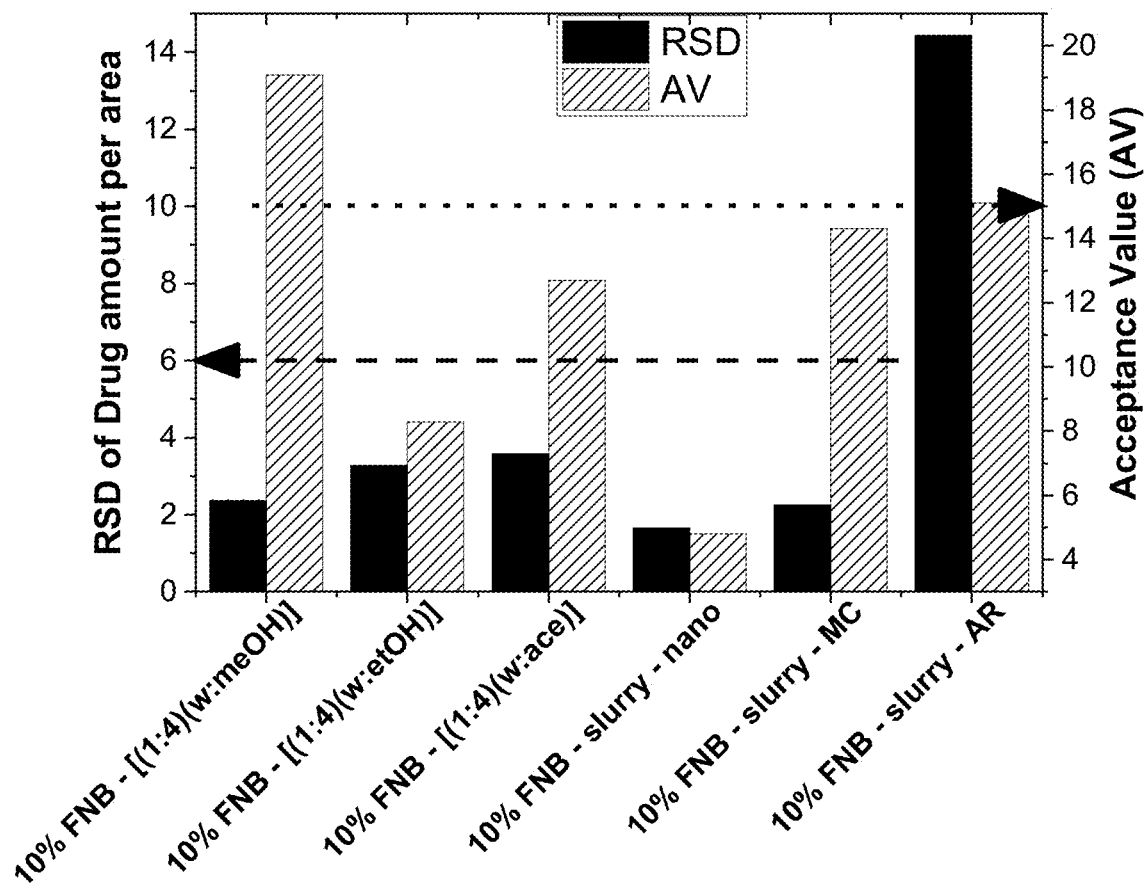
FIG. 51 shows Relative Standard Deviation (RSD) values of drug per area and acceptance values (AV) of 10% FNB loaded solution casting films made of different solvents, slurry casting films loaded with 10% as-received FNB, micronized-coated FNB, nano-sized FNB.

In FIG. 51, RSD values of drug per area and acceptance values (AV) for a comparison of drug content uniformity for 10% FNB loaded solution and slurry cast films are presented. RSD values explains to what degree the drug amount per area varies along the film. Except for the film loaded with 10% AR-FNB, the films showed relatively good content uniformity (RSD less than 6%). The acceptance value is defined by the United States Pharmacopedia as an indicator that takes the closeness to the label claim into account, as well as the drug content uniformity. While the film made as 10%-FNB—1:4 (water:meOH) met the conditions in terms of RSD (RSD less than 6%), it failed the acceptance value (AV greater than 15) criterion because of the low drug loading compared to label claim.

Figures 52A, 52B, 52C:
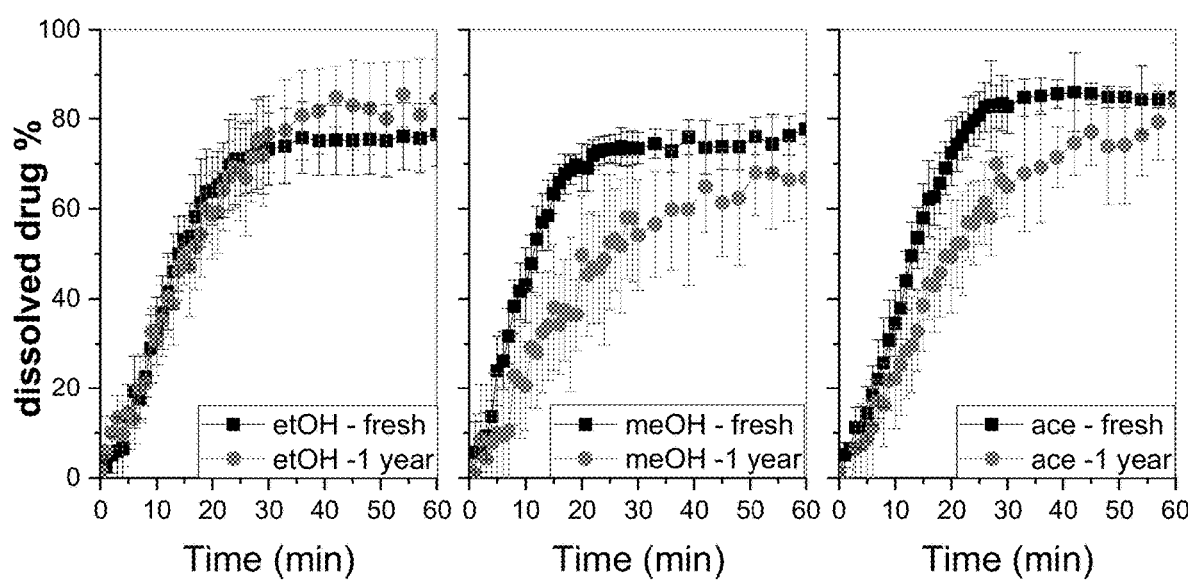
FIGS. 52A-52C show dissolution profiles of fresh and 1 year old 10% FNB loaded solution casting films made of different solvents.

The 10% FNB—1:4 (water:ace) film was stored in plastic bags at room temperature and humidity for 5 months and tested after 1 week, 2 weeks, 1 month and 5 months to study the impact of aging on the dry film product. Even though recrystallization was observed after a month (2.5% crystal was detected from DSC measurements) and 5 months (28.1 and 58.1% crystal was detected from 2 different DSC measurements), it did not affect the dissolution profiles of the films. The reason that the dissolution was not affected might be that the amorphous particles may be dominated in the film and recrystallites do not affect the rate as much regardless of their sizes. To analyze the stability further, the films made with solution casting were stored for a year and tested. While the dissolution rates of the 10% FNB—1:4 (water:meOH) and 10% FNB—1:4 (water:ace) films were decreased, 10% FNB—1:4 (water:etOH) was not substantially affected (FIGS. 52A-52C).

Figure 53:
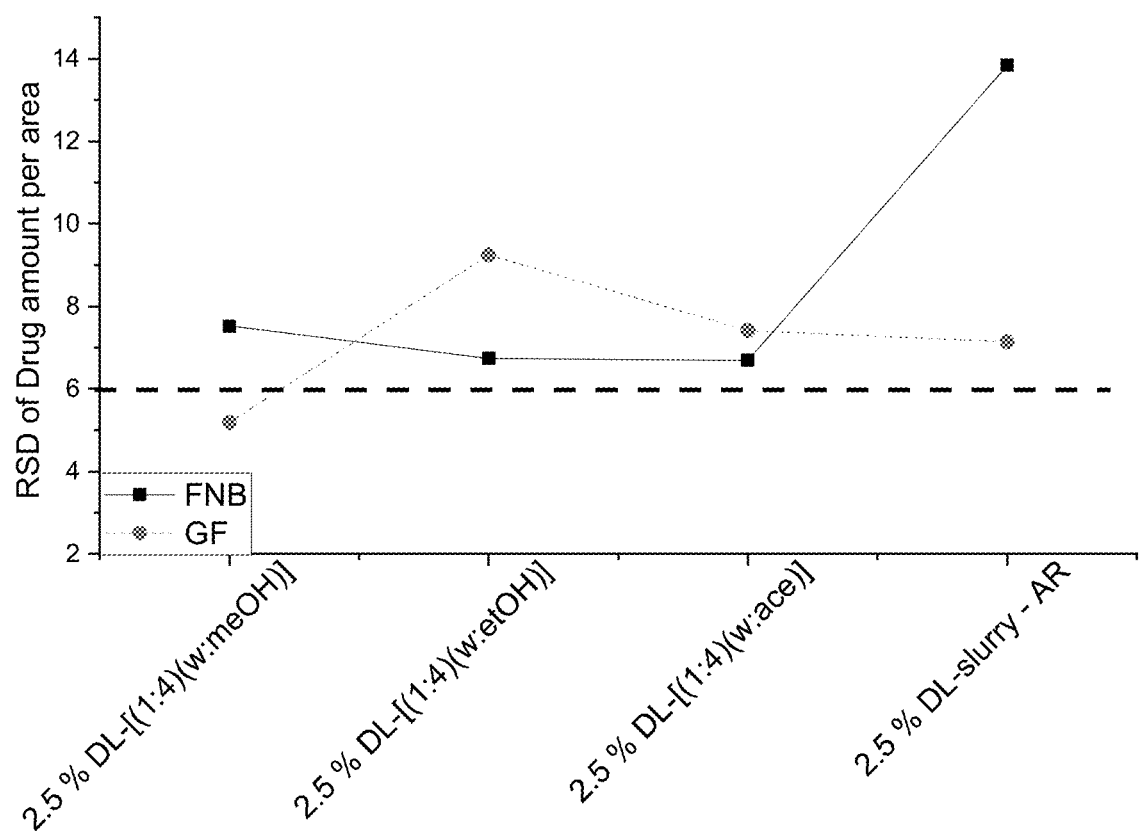
FIG. 53 shows Relative Standard Deviation (RSD) values of drug per area for solution casting films made of different solvents, slurry casting films loaded with 2.5% as-received FNB or GF.

The 2.5% FNB and GF loaded films were prepared with the same three solvents previously studied. At this lower drug loading, except for 2.5% GF—1:4 (water:meOH), the films prepared via solution casting and the slurry cast films loaded with AR drug exhibited poor drug content uniformity (RSD greater than 6%) for both drugs (FNB and GF) (FIG. 53). This was contrary to what was observed with the 10% DL films.

Figure 54A:
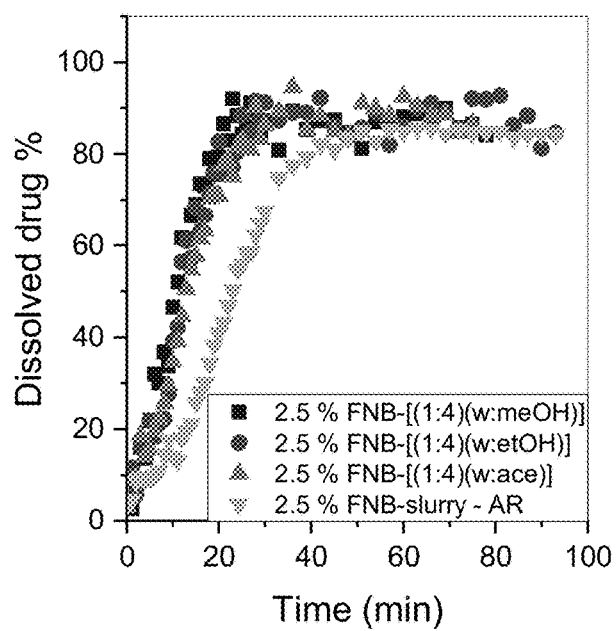
FIGS. 54A-54B shows dissolution profiles of 2.5% drug loaded solution casting films made of different solvents and slurry casting films loaded with 2.5% as-received drug FNB and GF.
Figure 54B:
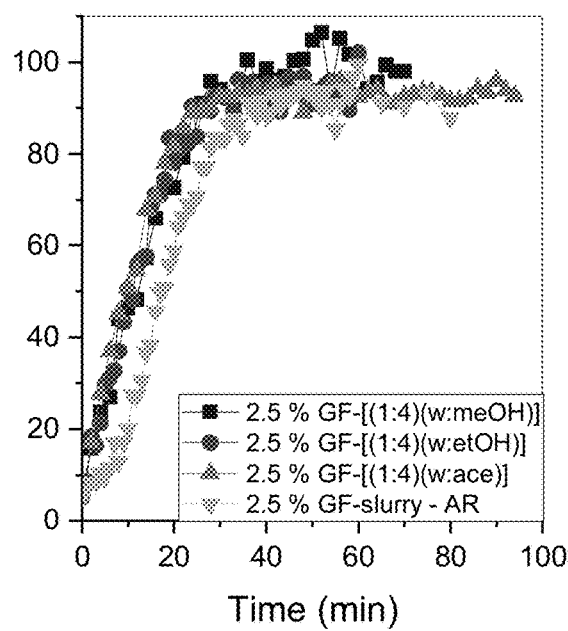

The solution cast films fabricated from different solvents showed similar dissolution rates, which was enhanced compared to the films loaded with as received drug for both FNB and GF (FIGS. 54A-54B).

Figure 55:
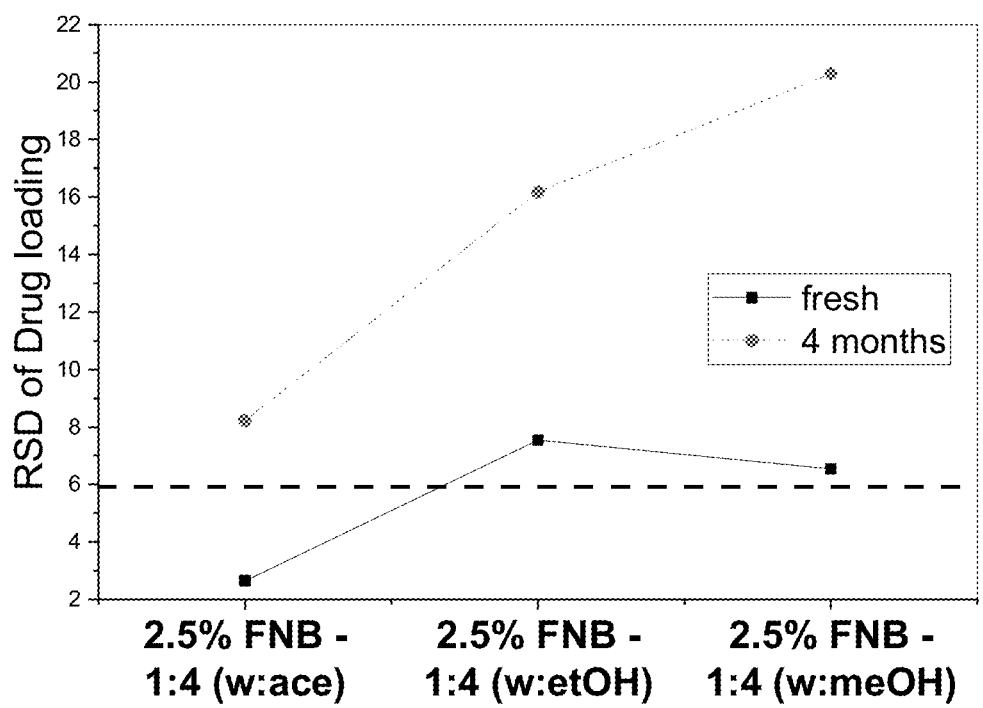
FIG. 55 shows RSD of drug loading of fresh and four months old 2.5 FNB loaded solution casting films made of different solvents.
Figure 56A:
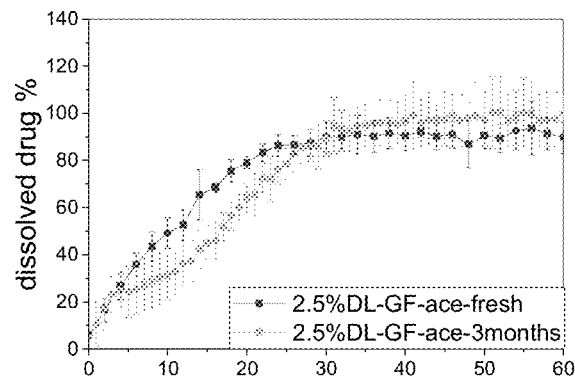
Figure 56B:
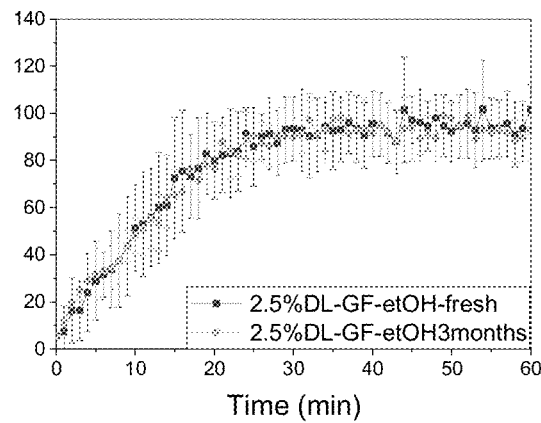
Figure 56C:
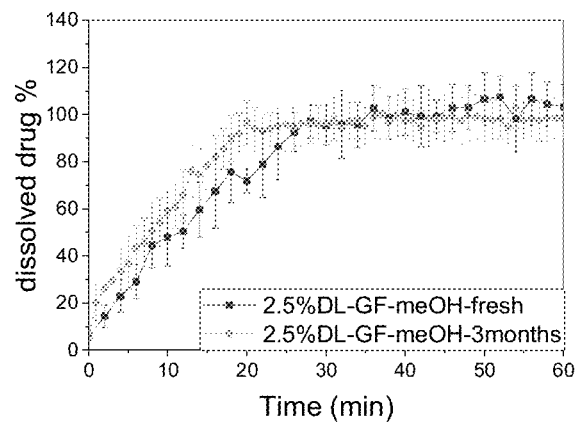

FNB was crystallized out of the films and those particles that were on the film surface could be lost, resulting in loss of drug content during handling and may have stuck to the bag. Drug loading was decreased in all cases, as was content uniformity (RSD greater than 6%) (FIG. 55).

Similar to 10% DL, solution cast films loaded with 2.5% FNB and GF were analyzed after four months or three months of storage in plastic bags at room temperature and humidity (FIGS. 56A-56C and FIGS. 57A-57C). Except for films made using 1:4 (w:ace) as solvent, the dissolution profiles did not show significant difference when % dissolved drug was used.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A method for fabricating a film based pharmaceutical product, the method comprising:
providing dry active agent poorly water-soluble particles;
micronizing the dry active agent poorly water-soluble particles and surface modifying the dry active agent poorly water-soluble particles with a dry coating agent via dry milling without addition of a surfactant to obtain micronized active agent particles surface coated with the coating agent, the micronized active agent particles surface coated with the coating agent in dry powder form;
mixing the micronized active agent particles surface coated with the coating agent in dry powder form with at least one film forming precursor to form a mixture; and
drying and fabricating the mixture to form a film;
wherein the mixing and drying steps are performed without addition of the surfactant such that the resulting film is fabricated without the surfactant.

2. The method of claim 1, wherein the step of micronizing the dry active agent poorly water-soluble particles and surface modifying the dry active agent poorly water-soluble particles with a dry coating agent via dry milling without addition of the surfactant to obtain micronized active agent particles surface coated with the coating agent includes simultaneously micronizing the dry active agent poorly water-soluble particles and surface modifying the dry active agent poorly water-soluble particles with a dry coating agent via dry milling without addition of the surfactant to obtain micronized active agent particles surface coated with the coating agent.

3. The method of claim 2, wherein the dry active agent poorly water-soluble particles are simultaneously micronized and surface modified with the dry coating agent via a fluid energy mill.

4. The method of claim 1, wherein the dry active agent poorly water-soluble particles include BCS Class II poorly water-soluble drug particles or BCS Class IV poorly water-soluble drug particles.

5. The method of claim 1, wherein the micronized active agent particles surface coated with the coating agent are directly mixed with the at least one film forming precursor to form the mixture.

6. The method of claim 1, wherein the micronized active agent particles surface coated with the coating agent are directly mixed with the at least one film forming precursor via a mixer to form the mixture, the mixer selected from the group consisting of a planetary mixer, an impeller mixer, a high intensity vibratory mixer and a twin screw extruder.

7. The method of claim 1, wherein the dry coating agent is selected from the group consisting of hydrophilic silica, silica, a lipid, lecithin, a wetting agent, and combinations thereof.

8. The method of claim 1, wherein the dry coating agent is dry coated to the micronized active agent particles.

9. The method of claim 1, wherein the mixture has a viscosity of from about 5,000 cP to about 18,500 cP.

10. The method of claim 1, wherein the at least one film forming precursor is a polymer solution.

11. The method of claim 1, wherein the micronized active agent particles include one or more particles having a particle size of about 3 µm or greater.

12. The method of claim 1, wherein the film has a tensile strength of from about 21.7 MPa to about 35.8 MPa.

13. The method of claim 1, wherein the dry active agent poorly water-soluble particles include pharmaceutical active agent particles; and
wherein the film is formed by solution casting or slurry casting the mixture.

14. The method of claim 1 further comprising the step of re-dispersing the fabricated film in a medium to form a re-dispersion;
wherein the micronized active agent particles, prior to mixing with the at least one film forming precursor, have a first D50 particle size distribution value and the re-dispersion of the fabricated film in the medium has a second D50 particle size distribution value, the first and second D50 particle size distribution values varying from one another by about 10% or less.

15. The method of claim 1, wherein a thickness of the film formed from the mixture is 500-2,000 µm.

16. The method of claim 1, wherein a thickness of the film formed from the mixture is 1,000-2,000 µm.

17. A method for fabricating a film based pharmaceutical product, the method comprising:
providing dry active agent poorly water-soluble particles;
micronizing the dry active agent poorly water-soluble particles and surface modifying the dry active agent poorly water-soluble particles with a dry coating agent via dry milling without addition of a surfactant to obtain micronized active agent particles surface coated with the coating agent, the micronized active agent particles surface coated with the coating agent in dry powder form;
mixing the micronized active agent particles surface coated with the coating agent in dry powder form with at least one film forming precursor to form a mixture; and
drying and fabricating the mixture to form a film;
wherein the mixing and drying steps are performed without addition of the surfactant such that the resulting film is fabricated without the surfactant;
wherein the dry active agent particles are simultaneously micronized and surface modified with the dry coating agent via a fluid energy mill;
wherein the dry active agent particles include poorly water-soluble drug particles;
wherein the micronized active agent particles surface coated with the coating agent are directly mixed with the at least one film forming precursor to form the mixture;
wherein the dry coating agent is dry coated to the micronized active agent particles; and
wherein the at least one film forming precursor is a polymer solution.

18. The method of claim 17, wherein the step of micronizing the dry active agent poorly water-soluble particles and surface modifying the dry active agent poorly water-soluble particles with a dry coating agent via dry milling without addition of the surfactant to obtain micronized active agent particles surface coated with the coating agent includes simultaneously micronizing the dry active agent poorly water-soluble particles and surface modifying the dry active agent poorly water-soluble particles with a dry coating agent via dry milling without addition of the surfactant to obtain micronized active agent particles surface coated with the coating agent.

19. A method for fabricating a film based pharmaceutical product, the method comprising:
providing dry active agent poorly water-soluble particles;
simultaneously micronizing the dry active agent poorly water-soluble particles and surface modifying the dry active agent poorly water-soluble particles with a dry coating agent via dry milling without addition of a surfactant to obtain micronized active agent particles surface coated with the coating agent, the micronized active agent particles surface coated with the coating agent in dry powder form;
mixing the micronized active agent particles surface coated with the coating agent in dry powder form with at least one film forming precursor to form a mixture; and
drying and fabricating the mixture to form a film;
wherein the mixing and drying steps are performed without addition of the surfactant such that the resulting film is fabricated without the surfactant;
wherein the dry active agent poorly water-soluble particles are simultaneously micronized and surface modified with the dry coating agent;
wherein the dry active agent poorly water-soluble particles include poorly water-soluble drug particles;
wherein the micronized active agent particles surface coated with the coating agent are directly mixed with the at least one film forming precursor via a planetary mixer or an impeller mixer to form the mixture;

wherein the dry coating agent is dry coated to the micronized active agent particles;
wherein the at least one film forming precursor is a polymer solution;
wherein the dry coating agent includes hydrophilic silica;
wherein the mixture has a viscosity of from about 5,000 cP to about 18,500 cP; and
wherein the micronized active agent particles include one or more particles having a particle size of about 4.2 μm.

* * * * *